(12) United States Patent
Duchateau et al.

(10) Patent No.: US 10,526,406 B2
(45) Date of Patent: Jan. 7, 2020

(54) CHIMERIC ANTIGEN RECEPTOR USING ANTIGEN RECOGNITION DOMAINS DERIVED FROM CARTILAGINOUS FISH

(71) Applicant: CELLECTIS, Paris (FR)

(72) Inventors: Philippe Duchateau, Draveil (FR); Julien Valton, New York, NY (US)

(73) Assignee: CELLECTIS, Paris (FR)

( * ) Notice: Subject to any disclaimer, the term of this patent is extended or adjusted under 35 U.S.C. 154(b) by 0 days.

(21) Appl. No.: 15/111,441

(22) PCT Filed: Jan. 14, 2015

(86) PCT No.: PCT/EP2015/050581
§ 371 (c)(1),
(2) Date: Jul. 13, 2016

(87) PCT Pub. No.: WO2015/107075
PCT Pub. Date: Jul. 23, 2015

(65) Prior Publication Data
US 2016/0333094 A1    Nov. 17, 2016

(30) Foreign Application Priority Data

Jan. 14, 2014   (DK) .................................. 2014 70016

(51) Int. Cl.
| | |
|---|---|
| *A61K 35/17* | (2015.01) |
| *C07K 16/28* | (2006.01) |
| *C07K 14/725* | (2006.01) |
| *C12N 5/0783* | (2010.01) |
| *C07K 14/705* | (2006.01) |
| *A61K 38/00* | (2006.01) |

(52) U.S. Cl.
CPC .......... *C07K 16/2803* (2013.01); *A61K 35/17* (2013.01); *C07K 14/7051* (2013.01); *C07K 14/70517* (2013.01); *C07K 14/70578* (2013.01); *C12N 5/0636* (2013.01); *A61K 38/00* (2013.01); *C07K 2317/24* (2013.01); *C07K 2317/53* (2013.01); *C07K 2317/565* (2013.01); *C07K 2317/569* (2013.01); *C07K 2319/03* (2013.01); *C07K 2319/74* (2013.01); *C12N 2510/00* (2013.01)

(58) Field of Classification Search
CPC ...................................................... A61K 35/17
USPC ...................................................... 424/184.1
See application file for complete search history.

(56) References Cited

U.S. PATENT DOCUMENTS

2006/0121005 A1* 6/2006 Berenson ............. C12N 5/0636
424/93.7
2013/0302250 A1   11/2013 Barelle et al.

FOREIGN PATENT DOCUMENTS

| WO | WO 2013/038203 A1 | 3/2013 |
| WO | 2013126712 A1 | 8/2013 |
| WO | 2013176915 A1 | 11/2013 |
| WO | WO 2013/167883 A1 | 11/2013 |
| WO | 2014127261 A1 | 8/2014 |
| WO | WO 2014/127261 A1 * | 8/2014 |

OTHER PUBLICATIONS

Wesolowski et al (Med Microbiol Immunol, 2009, 198: 157-174).*
Streltsov et al (PNAS, 2004, 101(34): 12444-12449).*
Jena et al (Blood, 2010, 116(7): 1035-1044).*
Kovalenko et al (JBC, 2013, 288: 17408-17419).*
Bridgeman et al (J Immunol, 2010, 184: 6938-6949).*
Flajnik et al., "A Case of Convergence: Why Did a Simple Alternative to Canonical Antibodies Arise in Sharks and Camels?" PLoS Biology, vol. 9, Aug. 2011, pp. 1-5.
International Search Report and Written Opinion issued in International Patent Application No. PCT/EP2015/050581 dated Apr. 23, 2015.
Jamnani et al., "T cells expressing VHH-directed oligoclonal chimeric HER2 antigen receptors: Towards tumor-directed oligoclonal T cell therapy," Biochimica et Biophysica Acta, vol. 1840, 2014, pp. 378-386.
Sharifzadeh et al., "Genetically engineered T cells bearing chimeric nanoconstructed receptors harboring TAG-72-specific camelid single domain antibodies as targeting agents," Cancer Letters, vol. 334, 2013, pp. 237-244.
Camacho-Villegas et al., "Human TNF cytokine neutralization with a vNAR from *Heterodontus francisci* shark," mAbs vol. 5(1), Jan./Feb. 2013, pp. 80-85.
Feige et al., "The structural analysis of shark IgNAR antibodies reveals evolutionary principles of immunoglobulins," PNAS, vol. 111 (2), Jun. 2014, pp. 8155-8160.
Kovalenko et al., "Atypical Antigen Recognition Mode of a Shark Immunoglobulin New Antigen Receptor (IgNAR) Variable Domain Characterized by Humanization and Structural Analysis," The Journal of Bio Chem., vol. 288(24), Jun. 2013, pp. 17408-17419.
Zielonka et al., "Structural insights and biomedical potential of IgNAR scaffolds from sharks," mAbs, vol. 7(1), Jan./Feb. 2015, pp. 15-25.

(Continued)

*Primary Examiner* — Sean A Aeder
(74) *Attorney, Agent, or Firm* — Arrigo, Lee, Guttman & Mouta-Bellum LLP

(57) ABSTRACT

The present invention relates to a new generation of chimeric antigen receptors (CAR), under single-chain or multi-chain forms, the specificity of which, to a desired antigen, is conferred by a VNAR polypeptide derived from monomeric antibodies from cartilaginous fish. Such CARs, which aim to redirect immune cell specificity toward selected undesired malignant cells, are compact and thus particularly adapted to target hollow antigens such as ions channels of efflux pumps present at the surface of drug-resistant cells. The invention encompasses the polynucleotides, vectors encoding said multi-chain CAR and the isolated cells expressing them at their surface, in particularly for their use in immunotherapy.

6 Claims, 5 Drawing Sheets
Specification includes a Sequence Listing.

(56) References Cited

OTHER PUBLICATIONS

Wesolowski et al., "Single domain antibodies: promising experimental and therapeutic tools in infection and Immunity," Med Microbiol Immunol, 2009, vol. 198, pp. 157-174.

Sharifzadeh et al., "Genetically engineered T calls bearing chimeric nanoconstructed receptors harboring TAG-72-specific camelid single domain antibodies as targeting agents," Cancer Letters, 2013, vol. 334, pp. 237-244.

Jamnani et al., "T cells expressing VHH-directed oligoclonal chimeric HER2 antigen receptors: Towards tumor-directed oligoclonal T cell therapy," Biochimica et Biophysica, Sep. 27, vol. 1840, No. 378-386, 2014.

* cited by examiner

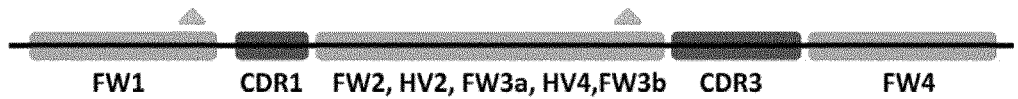

Fig. 1

```
                      10         20         30         40         50         60
                       |          |          |          |          |          |
7e80xx2      -MNIFLLSVLLALLPNVFTARVDQTPRTATKETGESLTINCVLRDTSCAFSSTGWYRTKL
12A9xx3      ------------------ARVDQTPRIATKETGESLTINCVLRDTACALDSTNWYRTKL
5A7xxx1      ------------------ARVDQTPRSVTKETGESLTINCVLRDASYALGSTCWYRKKS
E06xxx0      MGWSCIILFLVATATGAHSTRVDQTPRTATRETGESLTINCVLTDTSYPLYSTYWYRKNP
                                :******* .*:************ *:: .:  ** ***.:
Prim.cons.   M22222222L2A2222222ARVDQTPRTATKETGESLTINCVLRDTS2AL4ST4WYR2KL 70         80         90        100        110        120
                       |          |          |          |          |          |
7e80xx2      GSTNEQSISIGGRYVETVNKGSKSFSLRISDLRVEDSGTYKCQAYVIATMAPLCYASYSW
12A9xx3      GSTKEQTISIGGRYSETVDEGSNSASLTIRDLRVEDSGTYKCKAYRRCAFN----TGVGY
5A7xxx1      GEGNEESISKGGRYVETVNSGSKSFSLRINDLTVEDGGTYRCGLGVAGGYCDYALCSSRY
E06xxx0      GSSNKEQISISGRYVESVNKGTKSFSLRIKDLTVADSATYICRAMGTNIWT---------
             *. ::: ** .*** *:*:.*::* ** * ** * *.. ** *
Prim.cons.   GSTNE2SISIGGRYVETVNKGSKSFSLRI4DL2VEDSGTYKC4AYV4444422223S33Y 130        140        150        160
                       |          |          |          |
7e80xx2      NEKGAGTVLTVKPGVQPSPPVISLLYSATEEQRGNGFVQLICLISGYY
12A9xx3      KE-GAGTVLTVK------------------------------------
5A7xxx1      AECGDGTAVIVN------------------------------------
E06xxx0      GD-GAGTVLTVNHHHHHH------------------------------
              : * **.:**:
Prim.cons.   4E2GAGTVLTV2222222PPVISLLYSATEEQRGNGFVQLICLISGYY
```

7e80:   SEQ ID NO. 102 (type IV)
12A9:   SEQ ID NO. 115 (type II)
5A7:    SEQ ID NO. 101 (type I)
E06:    SEQ ID NO. 1

VNAR

CD8

CD3ζ

CD3R

VNAR

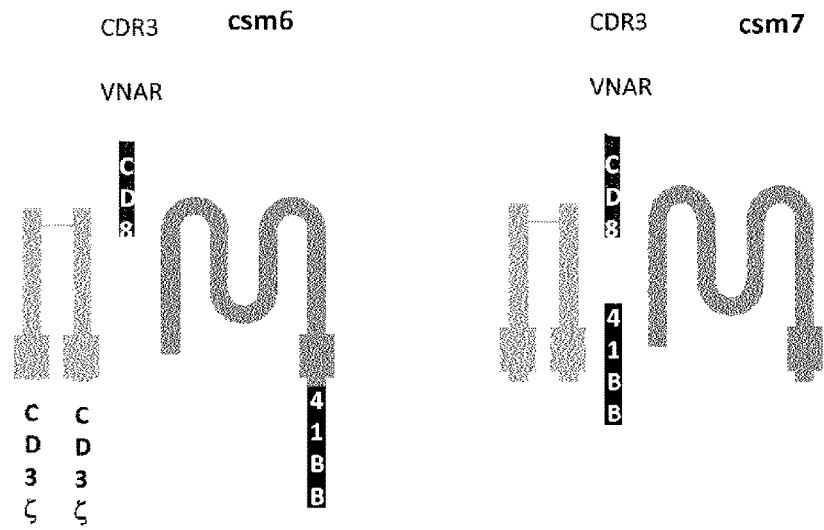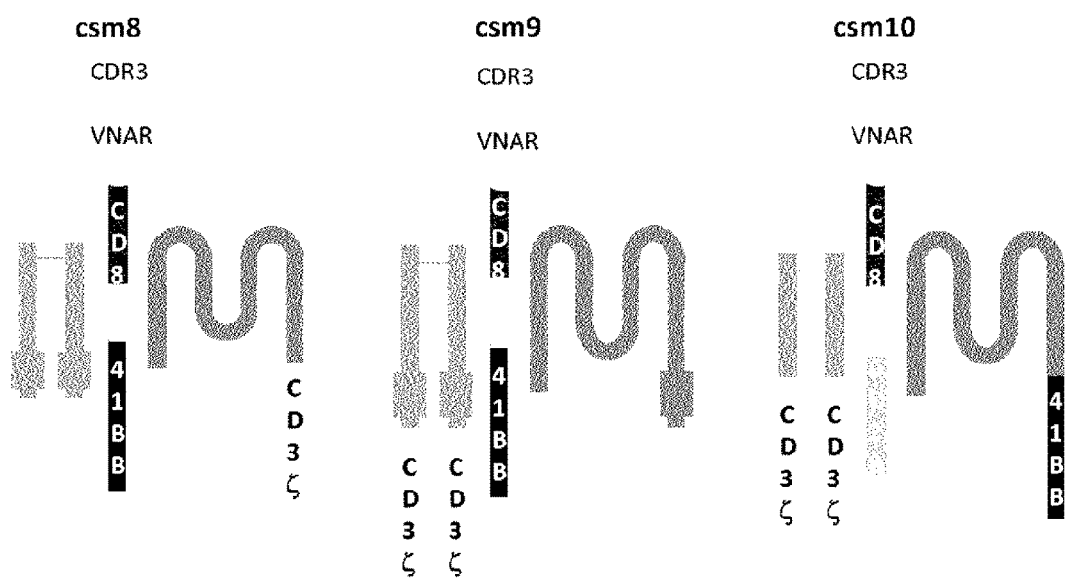
Fig. 6

SEQUENCE LISTING

```
<160> NUMBER OF SEQ ID NOS: 115

<210> SEQ ID NO 1
<211> LENGTH: 128
<212> TYPE: PRT
<213> ORGANISM: artificial sequence
<220> FEATURE:
<223> OTHER INFORMATION: >gi| 491668396| pdb| 4HGK| D Chain D,
      Shark Ignar Variable Domain (E06)

<400> SEQUENCE: 1

Met Gly Trp Ser Cys Ile Ile Leu Phe Leu Val Ala Thr Ala Thr Gly
1               5                   10                  15

Ala His Ser Thr Arg Val Asp Gln Thr Pro Arg Thr Ala Thr Arg Glu
            20                  25                  30
```

Thr Gly Glu Ser Leu Thr Ile Asn Cys Val Leu Thr Asp Thr Ser Tyr
            35                  40                  45

Pro Leu Tyr Ser Thr Tyr Trp Tyr Arg Lys Asn Pro Gly Ser Ser Asn
    50                  55                  60

Lys Glu Gln Ile Ser Ile Ser Gly Arg Tyr Val Glu Ser Val Asn Lys
65                  70                  75                  80

Gly Thr Lys Ser Phe Ser Leu Arg Ile Lys Asp Leu Thr Val Ala Asp
                85                  90                  95

Ser Ala Thr Tyr Ile Cys Arg Ala Met Gly Thr Asn Ile Trp Thr Gly
            100                 105                 110

Asp Gly Ala Gly Thr Val Leu Thr Val Asn His His His His His His
        115                 120                 125

<210> SEQ ID NO 2
<211> LENGTH: 112
<212> TYPE: PRT
<213> ORGANISM: artificial sequence
<220> FEATURE:
<223> OTHER INFORMATION: >gi| 491668397| pdb| 4HGM| A Chain A,
      Shark Ignar Variable Domain

<400> SEQUENCE: 2

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Gln Gln Lys Pro Gly Ser Ser Asn Lys Glu Gln
            35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys Ala Ala Ala His His His His His His
            100                 105                 110

<210> SEQ ID NO 3
<211> LENGTH: 109
<212> TYPE: PRT
<213> ORGANISM: Heterodontus francisci
<220> FEATURE:
<223> OTHER INFORMATION: >gi| 59892033| gb| AAX10148.1+51
      immunoglobulin NAR variable region, partial [Heterodontus
      francisci]

<400> SEQUENCE: 3

Ala Arg Val Asp Gln Thr Pro Arg Met Ala Thr Arg Glu Thr Gly Glu
1               5                   10                  15

Ser Leu Thr Ile Asn Cys Val Leu Val Asp Ala Ser Cys Asp Leu Ser
            20                  25                  30

Asp Thr Phe Trp Phe Arg Asn Asn Pro Gly Ser Thr His Arg Glu Arg
            35                  40                  45

Ile Thr Ile Gly Gly Arg Tyr Val Gln Ser Val Asn Lys Gly Ala Lys
    50                  55                  60

Ser Phe Ser Leu Gln Ile Lys Asp Leu Thr Val Glu Asp Ser Gly Thr
65                  70                  75                  80

Tyr Tyr Cys Lys Ala Gln Thr Leu Tyr Ser Leu Phe Cys Asp Asp Asp
                85                  90                  95

Tyr Tyr Tyr Asp Gly Ala Gly Thr Val Leu Thr Val Asn
            100                 105

<210> SEQ ID NO 4
<211> LENGTH: 106
<212> TYPE: PRT
<213> ORGANISM: Heterodontus francisci
<220> FEATURE:
<223> OTHER INFORMATION: >gi| 59892031| gb| AAX10147.1+51
      immunoglobulin NAR variable region, partial [Heterodontus
      francisci]

<400> SEQUENCE: 4

Ala Arg Val Asp Gln Thr Pro Arg Thr Ser Thr Arg Glu Thr Gly Glu
1               5                   10                  15

Phe Leu Thr Ile Asn Cys Val Leu Val Asp Thr Asn Tyr Ala Leu Ala
            20                  25                  30

Thr Thr Ser Trp Tyr Arg Asp Ala Pro Phe Pro Thr Asp Arg Glu Gln
        35                  40                  45

Ile Thr Ile Gly Gly Arg Tyr Leu Glu Ser Val Asn Lys Gly Thr Lys
    50                  55                  60

Ser Phe Ser Leu Gln Ile Lys Asp Met Thr Val Glu Asp Ser Gly Thr
65                  70                  75                  80

Tyr Tyr Cys Glu Ala Gly Glu Lys Arg Tyr Met Gly Ile His Val Tyr
                85                  90                  95

Ala Gly Ala Gly Thr Val Leu Thr Val Asp
            100                 105

<210> SEQ ID NO 5
<211> LENGTH: 637
<212> TYPE: PRT
<213> ORGANISM: Squalus acanthias
<220> FEATURE:
<223> OTHER INFORMATION: >gi| 355525308| gb| AES92986.1+51 IgNAR
      immunoglobulin heavy chain secretory form, partial [Squalus
      acanthias]

<400> SEQUENCE: 5

Gly Ile Arg Leu Thr Ile Asn Cys Val Leu Thr Asp Thr Ser Tyr Ala
1               5                   10                  15

Phe Tyr Ser Thr Tyr Trp Tyr Arg Lys Asn Pro Gly Ser Ser Asn Lys
            20                  25                  30

Glu Gln Ile Ser Ile Ser Gly Arg Tyr Val Glu Ser Val Asn Lys Arg
        35                  40                  45

Thr Lys Ser Phe Ser Leu Arg Ile Lys Asp Leu Thr Val Ala Asp Ser
    50                  55                  60

Ala Thr Tyr Ile Cys Lys Ala Tyr Ser Ser Val Trp Ser Thr Gly Ser
65                  70                  75                  80

Asn Tyr Tyr Asp Gly Ala Gly Thr Val Leu Thr Val Asn Ser Ala Pro
                85                  90                  95

Gln Pro Thr Pro Pro Ile Ile Ser Leu Leu Tyr Ser Ala Thr Asp Glu
            100                 105                 110

Leu Arg Glu Lys Gly Phe Val Gln Leu Val Cys Leu Ile Ser Glu Tyr
            115                 120                 125

Gln Pro Glu Ser Ile Gly Val Ser Trp Glu Lys Asn Gly Asn Ala Ile
        130                 135                 140

Gln Ser Gly Phe Thr Thr Ser Ser Ala Ala Lys Asn Ser Asn Gly Asp
145                 150                 155                 160

```
Phe Ser Ser Thr Ser Leu Leu Gln Val Pro Leu Gln Glu Trp Ala Ser
            165                 170                 175
Gly Ser Val Tyr Thr Cys Gln Val Ser His Ser Pro Thr Ser Ser Asn
        180                 185                 190
Gln Arg Lys Glu Ile Arg Ser Thr Ser Glu Leu Ala Val Phe Leu Arg
    195                 200                 205
Asp Pro Ser Val Glu Glu Ile Arg Ile Asn Lys Thr Ala Thr Leu Val
210                 215                 220
Cys Glu Val Val Ser Thr Val Pro Thr Glu Val Ala Ile Ser Trp Thr
225                 230                 235                 240
Val Asp Gly Lys Met Arg Thr Lys Gly Val Leu Thr Glu Pro Ala Thr
                245                 250                 255
Lys Tyr Gly Asp Gln Tyr Leu Thr Ile Gly Arg Leu Thr Ser Ser Val
            260                 265                 270
Glu Glu Trp Glu Ser Gly Ile Glu Tyr Ser Cys Ser Ala Gln Glu Gly
        275                 280                 285
Gln Ser Ser Thr Ala Val Ser Gln Arg Thr Gly Lys Ala Lys Val Glu
    290                 295                 300
Pro Val Lys Pro Lys Leu Arg Leu Leu Pro Pro Ser Pro Glu Glu Ile
305                 310                 315                 320
Gln Ser Thr Ser Ala Ala Thr Leu Thr Cys Leu Ile Arg Gly Phe Tyr
                325                 330                 335
Pro Asp Asn Ile Ile Val Ser Trp Glu Lys Asp Gly Ala Ala Leu Ser
            340                 345                 350
Ala Asn Val Thr Ser Phe Pro Thr Ala Leu Glu Gln Asp Leu Thr Phe
        355                 360                 365
Ser Thr Arg Ser Leu Leu Thr Leu Pro Ser Ala Glu Trp Lys Arg Gly
    370                 375                 380
Ser Thr Tyr Thr Cys Ala Ala Ser His Pro Pro Ser Gln Ser Thr Val
385                 390                 395                 400
Lys Gly Ser Ile Ser Ser Pro Lys Gly Asp Arg His Glu Ala Asp Ile
                405                 410                 415
Ser Val Lys Ile Leu Asn Pro Pro Phe Glu Glu Ile Trp Thr Gln Arg
            420                 425                 430
Thr Ala Thr Ile Val Cys Glu Val Val Tyr Ser Asp Leu Glu Asn Val
        435                 440                 445
Ser Val Ser Trp Gln Val Asp Gly Ser Arg Arg Thr Glu Gly Val Glu
    450                 455                 460
Thr Arg Thr Pro Glu Trp Ser Gly Ser Lys Ser Ala Val Val Ser Glu
465                 470                 475                 480
Leu Lys Val Thr Arg Ala Glu Trp Glu Ser Gly Val Glu Tyr Leu Cys
                485                 490                 495
Phe Val Glu Asp Ser Ala Leu Pro Thr Pro Val Lys Ile Ser Thr Arg
            500                 505                 510
Lys Val Lys Val Gly Glu Met Tyr Pro Pro Lys Val Tyr Val Leu Pro
        515                 520                 525
Pro Ser Ala Asp Glu Ile Asp Thr Glu Asn Thr Ala Thr Leu Val Cys
    530                 535                 540
Leu Ala Thr Gly Phe Tyr Pro Ala Glu Ile Tyr Ile Ala Trp Met Ala
545                 550                 555                 560
Asn Asp Thr Leu Leu Asp Ser Ala Tyr Pro Ser Gln Pro Asp Thr Glu
                565                 570                 575
Lys Thr Asn Gly Ser Ser Ser Ile Gly Ser Arg Leu Arg Leu Thr Ala
```

```
                   580                 585                 590
Ala Glu Trp Asn Ser Gly Thr Thr Tyr Ser Cys Leu Val Gly His Pro
            595                 600                 605

Ser Leu Lys Met Asn Leu Ile Arg Ser Ile Asn Lys Ser His Gly Lys
            610                 615                 620

Pro Thr Leu Val Asn Ile Ser Leu Val Leu Thr Asp Arg
625                 630                 635

<210> SEQ ID NO 6
<211> LENGTH: 628
<212> TYPE: PRT
<213> ORGANISM: Squalus acanthias
<220> FEATURE:
<223> OTHER INFORMATION: >gi| 355525312| gb| AES92988.1+51 IgNAR
      immunoglobulin heavy chain secretory form, partial [Squalus
      acanthias]

<400> SEQUENCE: 6

Gly Glu Ser Leu Thr Ile Asn Cys Val Leu Thr Asp Thr Ser His Ser
1               5                   10                  15

Leu Tyr Ser Thr Tyr Trp Tyr Arg Lys Asn Pro Gly Ser Ser Thr Thr
                20                  25                  30

Glu Gln Ile Ser Ile Ser Gly Arg Tyr Val Glu Ser Val Asn Lys Arg
            35                  40                  45

Thr Lys Ser Phe Ser Leu Arg Ile Lys Asp Leu Thr Val Ala Asp Ser
        50                  55                  60

Gly Thr Tyr Ile Cys Lys Gly Tyr Gly His Asp Gly Ala Gly Thr Val
65                  70                  75                  80

Leu Thr Val Asn Ser Ala Pro Gln Pro Thr Pro Pro Ile Ile Ser Leu
                85                  90                  95

Leu Tyr Ser Thr Thr Asp Glu Leu Arg Glu Lys Gly Phe Val Gln Leu
                100                 105                 110

Val Cys Leu Ile Ser Glu Tyr Gln Pro Glu Ser Ile Gly Val Ser Trp
            115                 120                 125

Glu Lys Asn Gly Asn Ala Ile Gln Ser Gly Phe Thr Ala Ser Ser Ala
        130                 135                 140

Ala Lys Asn Ser Asn Gly Asp Phe Ser Ser Thr Ser Leu Leu Gln Val
145                 150                 155                 160

Pro Leu Gln Glu Trp Ala Ser Gly Ser Val Tyr Thr Cys Gln Val Ser
                165                 170                 175

His Ser Pro Thr Ser Ser Asn Gln Arg Lys Glu Ile Arg Ser Thr Ser
                180                 185                 190

Glu Leu Ala Val Phe Leu Arg Asp Pro Ser Val Glu Glu Ile Trp Ile
            195                 200                 205

Asn Lys Thr Ala Thr Leu Val Cys Glu Val Val Ser Thr Val Pro Thr
        210                 215                 220

Glu Val Ala Ile Ser Trp Thr Val Asp Gly Lys Met Arg Thr Lys Gly
225                 230                 235                 240

Val Leu Thr Glu Pro Ala Thr Lys Tyr Gly Asp Gln Tyr Leu Thr Ile
                245                 250                 255

Gly Arg Leu Thr Ser Ser Val Glu Glu Trp Glu Ser Gly Ile Glu Tyr
                260                 265                 270

Ser Cys Ser Ala Gln Glu Gly Gln Ser Thr Ala Val Ser Gln Arg
            275                 280                 285

Thr Gly Lys Ala Lys Val Glu Pro Val Lys Pro Lys Leu Arg Leu Leu
        290                 295                 300
```

```
Pro Pro Ser Pro Glu Glu Ile Gln Ser Thr Ser Ala Ala Thr Leu Thr
305                 310                 315                 320

Cys Leu Ile Arg Gly Phe Tyr Pro Asp Asn Ile Ile Val Ser Trp Glu
            325                 330                 335

Lys Asp Gly Ala Ala Leu Ser Ala Asn Val Thr Ser Phe Pro Thr Ala
        340                 345                 350

Leu Glu Gln Asp Leu Thr Phe Ser Thr Arg Ser Leu Leu Thr Leu Pro
        355                 360                 365

Ser Ala Glu Trp Lys Lys Gly Ser Thr Tyr Thr Cys Ala Ala Ser His
370                 375                 380

Pro Pro Ser Gln Ser Thr Val Lys Gly Ser Ile Ser Pro Lys Gly
385                 390                 395                 400

Asp Cys His Glu Ala Asp Ile Ser Val Lys Ile Leu Asn Pro Pro Phe
            405                 410                 415

Glu Glu Ile Trp Thr Gln Arg Thr Ala Thr Ile Val Cys Glu Val Val
            420                 425                 430

Tyr Ser Asp Leu Glu Asn Val Ser Val Ser Trp Gln Val Asp Gly Ser
        435                 440                 445

Arg Arg Thr Glu Gly Val Glu Thr Arg Thr Pro Glu Trp Ser Gly Ser
450                 455                 460

Lys Ser Ala Ile Val Ser Lys Leu Lys Val Thr Arg Ala Glu Trp Glu
465                 470                 475                 480

Ser Gly Val Glu Tyr Leu Cys Phe Val Glu Asp Ser Ala Leu Pro Thr
            485                 490                 495

Pro Val Lys Ile Ser Thr Arg Lys Val Lys Val Gly Glu Met Tyr Pro
            500                 505                 510

Pro Lys Val Tyr Val Leu Pro Pro Ser Ala Asp Glu Ile Asp Thr Glu
        515                 520                 525

Asn Thr Ala Thr Leu Val Cys Leu Ala Thr Gly Phe Tyr Pro Ala Glu
530                 535                 540

Ile Tyr Ile Ala Trp Met Ala Asn Asp Thr Leu Leu Asp Ser Ala Tyr
545                 550                 555                 560

Pro Ser Gln Pro Asp Thr Glu Lys Thr Asn Gly Ser Ser Ile Gly
            565                 570                 575

Ser Arg Leu Arg Leu Thr Ala Ala Glu Trp Asn Ser Gly Thr Thr Tyr
            580                 585                 590

Ser Cys Leu Val Gly His Pro Ser Leu Lys Met Asn Leu Ile Arg Ser
        595                 600                 605

Ile Asn Lys Ser His Gly Lys Pro Thr Leu Val Asn Ile Ser Leu Val
610                 615                 620

Leu Thr Asp Arg
625

<210> SEQ ID NO 7
<211> LENGTH: 635
<212> TYPE: PRT
<213> ORGANISM: Squalus acanthias
<220> FEATURE:
<223> OTHER INFORMATION: >gi| 355525306| gb| AES92985.1+51 IgNAR
      immunoglobulin heavy chain secretory form, partial [Squalus
      acanthias]

<400> SEQUENCE: 7

Gly Glu Ser Leu Thr Ile Asn Cys Val Leu Ile Asp Thr Ser Tyr Val
1               5                   10                  15
```

```
Leu Tyr Ser Thr Tyr Trp Tyr Arg Arg Thr Pro Gly Ser Ser Asn Glu
            20                  25                  30

Glu Gln Ile Ser Ile Ser Gly Arg Tyr Val Glu Ser Val Asn Lys Arg
            35                  40                  45

Thr Lys Ser Phe Ser Leu Arg Ile Lys Asp Leu Thr Val Ala Asp Ser
        50                  55                  60

Ala Thr Tyr Ile Cys Lys Ala Tyr Arg Ser Thr Leu Pro Gly Ser Asp
65                  70                  75                  80

Tyr Asp Gly Ala Gly Thr Val Leu Thr Val Asn Ser Ala Pro Gln Pro
                85                  90                  95

Thr Pro Pro Ile Ile Ser Leu Leu Tyr Ser Ala Thr Asp Glu Leu Arg
            100                 105                 110

Glu Lys Gly Phe Val Gln Leu Val Cys Leu Ile Ser Glu Tyr Gln Pro
            115                 120                 125

Glu Ser Ile Gly Val Ser Trp Glu Lys Asn Gly Asn Ala Ile Gln Ser
            130                 135                 140

Gly Phe Thr Thr Ser Ala Ala Lys Asn Ser Asn Gly Asp Phe Ser
145                 150                 155                 160

Ser Thr Ser Leu Leu Gln Val Pro Leu Gln Glu Trp Ala Ser Gly Ser
                165                 170                 175

Val Tyr Thr Cys Gln Val Ser His Ser Pro Thr Ser Ser Asn Gln Arg
            180                 185                 190

Lys Glu Ile Arg Ser Thr Ser Glu Leu Ala Val Phe Leu Arg Asp Pro
            195                 200                 205

Ser Val Glu Glu Ile Trp Ile Asn Lys Thr Ala Thr Leu Val Cys Glu
210                 215                 220

Val Val Ser Thr Val Pro Thr Glu Val Ala Ile Ser Trp Thr Val Asp
225                 230                 235                 240

Gly Lys Met Arg Thr Lys Gly Val Leu Thr Glu Pro Ala Thr Lys Tyr
                245                 250                 255

Gly Asp Gln Tyr Leu Thr Ile Gly Arg Leu Thr Ser Ser Val Glu Glu
            260                 265                 270

Trp Glu Ser Gly Ile Glu Tyr Ser Cys Ser Ala Gln Glu Gly Gln Ser
            275                 280                 285

Ser Thr Ala Val Ser Gln Arg Thr Gly Lys Ala Lys Val Glu Pro Val
290                 295                 300

Lys Pro Lys Leu Arg Leu Leu Pro Pro Ser Pro Glu Glu Ile Gln Ser
305                 310                 315                 320

Thr Ser Ala Ala Thr Leu Thr Cys Leu Ile Arg Gly Phe Tyr Pro Asp
                325                 330                 335

Asn Ile Ile Val Ser Trp Glu Lys Asp Gly Ala Ala Leu Ser Ala Asn
            340                 345                 350

Val Thr Ser Phe Pro Thr Ala Leu Glu Gln Asp Leu Thr Phe Ser Thr
                355                 360                 365

Arg Ser Leu Leu Thr Leu Pro Ser Ala Glu Trp Lys Arg Gly Ser Thr
370                 375                 380

Tyr Thr Cys Ala Ala Ser His Pro Pro Ser Gln Ser Thr Val Lys Gly
385                 390                 395                 400

Ser Ile Ser Ser Pro Lys Gly Asp Cys His Glu Ala Asp Ile Ser Val
                405                 410                 415

Lys Ile Leu Asn Pro Pro Phe Glu Glu Ile Trp Thr Gln Arg Thr Ala
            420                 425                 430

Thr Ile Val Cys Glu Val Val Tyr Ser Asp Leu Glu Asn Val Ser Val
```

```
                435                 440                 445
Ser Trp Gln Val Asp Gly Ser Arg Arg Thr Glu Gly Val Glu Thr Arg
    450                 455                 460

Thr Pro Glu Trp Ser Gly Ser Lys Ser Ala Ile Val Ser Lys Leu Lys
465                 470                 475                 480

Val Thr Arg Ala Glu Trp Glu Ser Gly Val Glu Tyr Leu Cys Phe Val
                485                 490                 495

Glu Asp Ser Ala Leu Pro Thr Pro Val Lys Ile Ser Thr Arg Lys Val
            500                 505                 510

Lys Val Gly Glu Met Tyr Pro Pro Lys Val Tyr Val Leu Pro Pro Ser
        515                 520                 525

Ala Asp Glu Ile Asp Thr Glu Asn Thr Ala Thr Leu Val Cys Leu Ala
    530                 535                 540

Thr Gly Phe Tyr Pro Ala Glu Ile Tyr Ile Ala Trp Met Ala Asn Asp
545                 550                 555                 560

Thr Leu Leu Asp Ser Ala Tyr Pro Ser Gln Pro Asp Thr Glu Lys Thr
                565                 570                 575

Asn Gly Ser Asn Ser Ile Gly Ser Arg Leu Arg Leu Thr Ala Ala Glu
            580                 585                 590

Trp Asn Ser Gly Thr Thr Tyr Ser Cys Leu Val Gly His Pro Ser Leu
        595                 600                 605

Lys Met Asn Leu Ile Arg Ser Ile Asn Lys Ser His Gly Lys Pro Thr
    610                 615                 620

Leu Val Asn Ile Ser Leu Val Leu Thr Asp Arg
625                 630                 635

<210> SEQ ID NO 8
<211> LENGTH: 111
<212> TYPE: PRT
<213> ORGANISM: Heterodontus francisci
<220> FEATURE:
<223> OTHER INFORMATION: >gi| 59892021| gb| AAX10142.1+51
      immunoglobulin NAR variable region, partial [Heterodontus
      francisci]

<400> SEQUENCE: 8

Ala Arg Val Tyr Gln Thr Pro Arg Thr Ala Thr Arg Glu Thr Gly Glu
1               5                   10                  15

Ser Leu Ser Ile Asn Cys Val Phe Thr Asp Ser Ser Cys Gly Leu His
            20                  25                  30

Gly Thr Ser Trp Phe Arg Asn Asn Pro Gly Ser Thr Asp Trp Glu Arg
        35                  40                  45

Ile Thr Ile Gly Arg Arg Tyr Val Glu Ser Val Asn Lys Gly Ala Lys
    50                  55                  60

Ser Phe Ser Leu Gln Ile Lys Asp Leu Thr Val Glu Asp Ser Val Thr
65                  70                  75                  80

Tyr Tyr Cys Lys Ala Gln Thr Pro Thr Lys Ser Ser Tyr Leu Gly Cys
                85                  90                  95

Ser Ser Tyr Tyr Tyr Asp Gly Ala Gly Thr Val Leu Thr Val Asn
            100                 105                 110

<210> SEQ ID NO 9
<211> LENGTH: 108
<212> TYPE: PRT
<213> ORGANISM: Heterodontus francisci
<220> FEATURE:
<223> OTHER INFORMATION: >gi| 59892019| gb| AAX10141.1+51
      immunoglobulin NAR variable region, partial [Heterodontus
```

-continued francisci]

<400> SEQUENCE: 9

Ala Ser Leu Asp Gln Thr Pro Arg Thr Ala Thr Arg Glu Thr Gly Glu
1               5                   10                  15

Ser Leu Thr Ile Asn Cys Ile Leu Thr Asp Thr Val Cys Gly Leu Tyr
            20                  25                  30

Gly Thr Ser Trp Phe Arg Asn Asn Pro Gly Ser Thr Asp Trp Glu Arg
        35                  40                  45

Ile Thr Ile Gly Arg Arg Tyr Val Glu Ser Val Asn Lys Gly Ala Lys
    50                  55                  60

Ser Phe Ser Leu Gln Ile Lys Asp Leu Thr Val Glu Ser Val Thr
65                  70                  75                  80

Tyr Tyr Cys Lys Ala Gln Thr Pro Thr Gly Ser Ser Tyr Leu Gly Cys
                85                  90                  95

Ser Ser Tyr Tyr Tyr Asp Gly Ala Gly Thr Val Leu
            100                 105

<210> SEQ ID NO 10
<211> LENGTH: 115
<212> TYPE: PRT
<213> ORGANISM: Heterodontus francisci
<220> FEATURE:
<223> OTHER INFORMATION: >gi| 59892017| gb| AAX10140.1+51
    immunoglobulin NAR variable region, partial [Heterodontus
    francisci]

<400> SEQUENCE: 10

Ala Thr Arg Val Asp Gln Thr Pro Arg Thr Ala Arg Glu Thr Gly
1               5                   10                  15

Glu Ser Leu Asn Ile Asn Cys Val Leu Thr Asp Thr Ser His Ile Ser
            20                  25                  30

Phe Gly Thr Lys Trp Phe Trp Asn Asn Pro Gly Ser Thr Asp Trp Glu
        35                  40                  45

Ser Ile Thr Ile Gly Gly Arg Tyr Val Glu Ser Val Asn Asn Gln Ala
    50                  55                  60

Lys Ser Phe Ser Leu Gln Ile Lys Asp Leu Thr Val Glu Asp Ser Gly
65                  70                  75                  80

Thr Tyr Tyr Cys Lys Ala Gln Thr Arg Tyr Phe Ser Asn Thr Arg Leu
                85                  90                  95

Gly Glu Pro Leu Arg Ser Ser Asp Tyr Asp Gly Ala Gly Thr Val Leu
            100                 105                 110

Thr Val Asn
    115

<210> SEQ ID NO 11
<211> LENGTH: 114
<212> TYPE: PRT
<213> ORGANISM: Ginglymostoma cirratum
<220> FEATURE:
<223> OTHER INFORMATION: >gi| 21539972| gb| AAM52970.1+51
    antigen receptor [Ginglymostoma cirratum]

<400> SEQUENCE: 11

Leu Leu Ala Leu Leu Pro Tyr Val Phe Thr Ala Arg Val Asp Gln Thr
1               5                   10                  15

Pro Gln Thr Ile Thr Lys Glu Thr Gly Glu Ser Leu Thr Ile Asn Cys
            20                  25                  30

Val Leu Arg Asp Ser Asn Cys Ala Leu Ser Ser Thr Tyr Trp Tyr Arg

```
                    35                  40                  45
Lys Lys Ser Gly Ser Thr Asn Glu Glu Ser Ile Ser Lys Gly Gly Arg
    50                  55                  60

Tyr Val Glu Thr Val Asn Ser Gly Ser Lys Ser Phe Ser Leu Arg Ile
65                  70                  75                  80

Asn Asp Leu Thr Phe Glu Asp Ser Gly Thr Tyr Arg Cys Asn Pro Leu
                85                  90                  95

Cys Ile Gly Asn Trp Arg Val Tyr Gly Gly Thr Val Thr Val
                100                 105                 110

Asn Pro
```

<210> SEQ ID NO 12
<211> LENGTH: 635
<212> TYPE: PRT
<213> ORGANISM: Squalus acanthias
<220> FEATURE:
<223> OTHER INFORMATION: >gi| 355525310| gb| AES92987.1+51 IgNAR
      immunoglobulin heavy chain secretory form, partial [Squalus
      acanthias]

<400> SEQUENCE: 12

```
Gly Glu Ser Leu Thr Ile Asn Cys Val Leu Thr Asp Thr Asn Tyr Gly
1               5                   10                  15

Leu Ser Ser Thr Tyr Trp Tyr Arg Lys Asn Pro Gly Ser Ser Asn Lys
                20                  25                  30

Glu Gln Ile Ser Ile Ser Gly Arg Tyr Val Glu Ser Val Asn Lys Arg
                35                  40                  45

Thr Lys Ser Phe Ser Leu Arg Ile Lys Asp Leu Thr Val Ala Asp Ser
    50                  55                  60

Ala Thr Tyr Ile Cys Ser Glu Ala His Arg Ala Gly Asp Ser Tyr Asp
65                  70                  75                  80

Val Tyr Gly Ala Gly Thr Val Leu Thr Val Asn Ser Ala Pro Gln Asn
                85                  90                  95

Asn Pro Pro Ile Ile Ser Leu Leu Tyr Thr Ala Thr Asp Glu Leu Arg
                100                 105                 110

Glu Lys Gly Phe Val Gln Leu Val Cys Leu Ile Ser Glu Tyr Gln Pro
                115                 120                 125

Glu Ser Ile Gly Val Ser Trp Glu Lys Asn Gly Asn Ala Ile Gln Ser
    130                 135                 140

Gly Phe Thr Thr Ser Ser Ala Ala Lys Asn Ser Asn Gly Asp Phe Ser
145                 150                 155                 160

Ser Thr Ser Leu Leu Gln Val Pro Leu Gln Glu Trp Ala Ser Gly Ser
                165                 170                 175

Val Tyr Ser Cys Gln Val Ser His Ser Pro Thr Ser Ser Asn Gln Arg
                180                 185                 190

Lys Glu Ile Arg Ser Thr Ser Glu Leu Ala Val Phe Leu Arg Asp Pro
                195                 200                 205

Ser Val Glu Glu Ile Trp Ile Asn Lys Thr Ala Thr Leu Val Cys Glu
    210                 215                 220

Val Ile Ser Thr Val Pro Thr Glu Val Ala Ile Ser Trp Thr Val Asp
225                 230                 235                 240

Gly Lys Met Arg Thr Glu Gly Val Leu Thr Glu Pro Ala Thr Lys Tyr
                245                 250                 255

Gly Asp Gln Tyr Leu Thr Ile Gly Arg Leu Thr Ser Ser Val Glu Glu
                260                 265                 270
```

```
Trp Glu Ser Gly Val Glu Tyr Ser Cys Ser Ala Gln Gln Gly Gln Ser
            275                 280                 285
Ser Thr Ala Val Ser Gln Arg Thr Gly Lys Ala Lys Val Glu Pro Met
290                 295                 300
Lys Pro Lys Leu Arg Leu Leu Pro Pro Ser Pro Glu Glu Ile Gln Ser
305                 310                 315                 320
Thr Ser Ala Ala Thr Leu Thr Cys Leu Ile Arg Gly Phe Tyr Pro Asp
                325                 330                 335
Asn Ile Thr Val Ser Trp Glu Lys Asp Gly Ala Ala Leu Ser Ala Asn
            340                 345                 350
Val Thr Ser Ser Pro Thr Ala Leu Glu Gln Asp Gln Thr Phe Ser Thr
        355                 360                 365
Arg Ser Leu Leu Thr Leu Pro Ser Ala Glu Trp Lys Arg Glu Ser Thr
370                 375                 380
Tyr Thr Cys Ala Ala Ser His Pro Pro Ser Gln Ser Thr Val Lys Gly
385                 390                 395                 400
Ala Ile Ser Ser Pro Lys Gly Asp Cys His Glu Ala Asp Ile Ser Val
                405                 410                 415
Lys Ile Leu Asn Pro Pro Phe Glu Glu Ile Trp Thr Gln Arg Thr Ala
            420                 425                 430
Thr Ile Val Cys Glu Val Val Tyr Ser Asp Leu Glu Asn Val Ser Val
        435                 440                 445
Ser Trp Gln Val Asp Gly Ser Arg Arg Thr Glu Gly Val Glu Thr Arg
450                 455                 460
Thr Pro Glu Trp Ser Gly Ser Lys Ser Ala Ile Val Ser Lys Leu Lys
465                 470                 475                 480
Val Thr Arg Ala Glu Trp Glu Ser Gly Val Glu Tyr Leu Cys Phe Val
                485                 490                 495
Glu Asp Ser Ala Leu Pro Thr Pro Val Lys Ile Ser Thr Arg Lys Val
            500                 505                 510
Lys Val Gly Glu Met Tyr Pro Pro Lys Val Tyr Val Leu Pro Pro Ser
        515                 520                 525
Ala Asp Glu Ile Asp Thr Glu Asn Thr Ala Thr Leu Val Cys Leu Ala
530                 535                 540
Thr Gly Phe Tyr Pro Ala Glu Ile Tyr Ile Ala Trp Met Ala Asn Asp
545                 550                 555                 560
Thr Leu Leu Asp Ser Ala Tyr Pro Ser Gln Pro Asp Thr Glu Lys Ala
                565                 570                 575
Asn Gly Ser Ser Ser Ile Gly Ser Arg Leu Arg Leu Thr Ala Ala Glu
            580                 585                 590
Trp Asn Ser Gly Thr Thr Tyr Ser Cys Leu Val Gly His Pro Ser Leu
        595                 600                 605
Lys Arg Asn Leu Ile Arg Ser Ile Asn Lys Ser His Gly Lys Pro Thr
610                 615                 620
Leu Val Asn Ile Ser Leu Val Leu Thr Asp Arg
625                 630                 635

<210> SEQ ID NO 13
<211> LENGTH: 108
<212> TYPE: PRT
<213> ORGANISM: Ginglymostoma cirratum
<220> FEATURE:
<223> OTHER INFORMATION: >gi| 25987499| gb| AAN75876.1+51
      AF447120_1 novel antigen receptor [Ginglymostoma cirratum]

<400> SEQUENCE: 13
```

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Ala Cys Lys Ala Glu Gly Met Asp Arg Gly Ile Arg Leu Asn Cys
                85                  90                  95

Val Ile Tyr Gly Gly Gly Thr Val Thr Val Asn
                100                 105

<210> SEQ ID NO 14
<211> LENGTH: 124
<212> TYPE: PRT
<213> ORGANISM: Ginglymostoma cirratum
<220> FEATURE:
<223> OTHER INFORMATION: >gi| 21805812| gb| AAM76812.1+51 antigen
      receptor [Ginglymostoma cirratum]

<400> SEQUENCE: 14

Val Leu Leu Ala Leu Leu Pro Tyr Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Thr Asn Cys Pro Leu Ser Ser Thr Asp Trp Tyr
        35                  40                  45

Arg Lys Lys Ser Gly Ser Thr Asn Glu Glu Ser Ile Ser Ile Ala Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Ser Gly Thr Tyr Arg Cys Asn Val
                85                  90                  95

Tyr Asn Trp Asn Asp Asp Ser Ser Asp Cys Glu Leu Pro Arg Tyr Asp
                100                 105                 110

Val Tyr Gly Gly Gly Thr Val Thr Val Asn Pro
            115                 120

<210> SEQ ID NO 15
<211> LENGTH: 104
<212> TYPE: PRT
<213> ORGANISM: Ginglymostoma cirratum
<220> FEATURE:
<223> OTHER INFORMATION: >gi| 25987497| gb| AAN75875.1+51
      AF447119_1 novel antigen receptor [Ginglymostoma cirratum]

<400> SEQUENCE: 15

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

```
Ser Phe Ser Leu Arg Ile Asn Asp Leu Thr Val Glu Asp Ser Gly Thr
 65                  70                  75                  80

Tyr Arg Cys Lys Val Ser Arg Cys Ser Thr Asn Leu Ile Gly Tyr Gly
                 85                  90                  95

Gly Gly Thr Val Val Thr Val Asn
            100

<210> SEQ ID NO 16
<211> LENGTH: 678
<212> TYPE: PRT
<213> ORGANISM: Triakis scyllium
<220> FEATURE:
<223> OTHER INFORMATION: >gi| 307685087| dbj| BAJ20185.1+
      51 immunoglobulin NAR [Triakis scyllium]

<400> SEQUENCE: 16

Met His Ile Phe Trp Ala Ala Leu Leu Thr Trp Leu Ser Asn Ala
 1               5                  10                  15

Phe Ser Ala His Val Asp Gln Thr Pro Arg Val Ala Thr Lys Glu Thr
                 20                  25                  30

Gly Glu Ser Leu Thr Ile Asn Cys Val Leu Arg Gly Ala Ser Cys Gly
             35                  40                  45

Leu Tyr Ala Thr Ser Trp Phe Arg Gln Asn Pro Gly Ser Thr Gly Trp
 50                  55                  60

Glu Arg Ile Thr Ile Gly Gly Arg Tyr Val Glu Ser Val Asn Lys Gly
 65                  70                  75                  80

Ser Lys Ser Phe Ser Leu Gln Ile Lys Asp Leu Thr Val Glu Asp Ser
                 85                  90                  95

Val Thr Phe Tyr Cys Lys Ala Gln Asp His Arg Tyr Tyr Val Ala Arg
                100                 105                 110

Cys Leu Lys Ser Pro Ala Ala Asn Tyr Tyr Asp Gly Ala Gly Thr Val
            115                 120                 125

Leu Thr Val Asn Pro Gly Pro Thr Pro Pro Ile Ile Asn Leu Phe Ser
130                 135                 140

Glu Thr Asp Glu Leu Arg Ala Lys Gly Phe Val Gln Leu Ile Cys Leu
145                 150                 155                 160

Ile Ser Glu Tyr Lys Pro Glu Ser Ile Arg Val Ser Trp Glu Lys Asn
                165                 170                 175

Gly Asn Ala Arg Gln Ser Gly Phe Thr Thr Thr Ser Pro Cys Lys Thr
            180                 185                 190

Ala Lys Gly Glu Phe Gln Ser Arg Ser Ile Leu Thr Leu Pro Leu Gln
        195                 200                 205

Glu Trp Asn Ser Gly Ser Thr Tyr Ser Cys Gln Val Thr His Ser Ala
    210                 215                 220

Thr Asn Ser Asn Lys Arg Lys Glu Ile Arg Ser Thr Ser Glu Ile Thr
225                 230                 235                 240

Val Phe Leu Arg Asp Pro Ser Leu Glu Glu Ile Trp Ile Lys Lys Thr
                245                 250                 255

Val Thr Leu Ile Cys Glu Val Val Ser Thr Val Pro Ser Val Val Gly
            260                 265                 270

Ile Ser Trp Thr Val Asp Gly Lys Lys Arg Thr Glu Gly Val Gln Ile
        275                 280                 285

Glu Gly Arg Gln Gln Gly Gln Asn Gln Tyr Leu Thr Ile Ser Arg Leu
    290                 295                 300

Thr Ser Ser Val Glu Glu Trp Asp Arg Gly Ala Glu Tyr Asn Cys Ser
```

```
305                 310                 315                 320
Ala Gln Gln Ser Glu Ser Ser Thr Pro Val Ser Lys His Thr Gln Lys
                325                 330                 335

Leu Lys Val Lys Pro Ser Lys Pro Asn Leu Arg Leu Pro Pro Ser
                340                 345                 350

Ala Glu Glu Leu Gln Ser Ser Val Ala Thr Leu Thr Cys Leu Ile
                355                 360                 365

Arg Gly Phe Tyr Pro Asp Lys Ile Ser Ile Ser Trp Glu Lys Asp Gly
370                 375                 380

Ala Val Leu Ser Ser Asn Ile Thr Arg Phe Pro Thr Ala Leu Glu Gln
385                 390                 395                 400

Asp Gln Thr Phe Ser Thr Ser Ser Leu Leu Ile Leu Pro Ala Gly Glu
                405                 410                 415

Trp Lys Thr Gly Ala Arg Tyr Thr Cys Thr Ala Ser His Pro Ala Thr
                420                 425                 430

Lys Phe Thr Gly Lys Arg Thr Ile Asn Ser Pro Lys Ala Asp Cys Tyr
                435                 440                 445

Glu Glu Asp Ile Ser Val Asn Ile Leu Asn Pro Ser Phe Glu Glu Ile
                450                 455                 460

Trp Val Gln Lys Thr Ala Thr Ile Val Cys Glu Ile Arg Tyr Thr Val
465                 470                 475                 480

Leu Glu Asn Val Ser Val Ser Trp Gln Val Asp Gly Arg Met Arg Thr
                485                 490                 495

Glu Gly Val Glu Thr Gln Thr Pro Glu Trp Ser Gly Ser Lys Thr Thr
                500                 505                 510

Ile Met Ser Lys Leu Lys Val Thr Ala Ala Glu Trp Asp Thr Gly Val
                515                 520                 525

Glu Tyr Val Cys Leu Ala Glu Gly Ser Glu Leu Pro Thr Pro Lys Lys
                530                 535                 540

Arg Ser Thr Arg Lys Ile Lys Val Gly Ala Met Asn Ser Pro Lys Val
545                 550                 555                 560

Tyr Ile Leu Pro Pro Ser Val Ala Glu Ile Asp Ser Glu Lys Thr Ala
                565                 570                 575

Thr Leu Met Cys Leu Ala Thr Gly Phe Tyr Pro Ala Glu Ile Tyr Ile
                580                 585                 590

Ala Trp Leu Ala Asn Asp Thr Leu Leu Asp Ser Asp Phe Pro Asn Gln
                595                 600                 605

Pro Val Ser Glu Lys Gly Asn Gly Ser Ser Phe Ile Ala Ser Arg Leu
                610                 615                 620

Arg Leu Thr Ala Ala Glu Trp Asn Thr Gly Thr Thr Tyr Ser Cys Leu
625                 630                 635                 640

Val Gly His Pro Ser Leu Glu Arg Asn Leu Ile Arg Ser Ile Asn Lys
                645                 650                 655

Ser Tyr Gly Lys Pro Thr Leu Val Asn Val Ser Leu Ala Leu Ala Asp
                660                 665                 670

Ser Phe Thr Ser Cys Ala
                675

<210> SEQ ID NO 17
<211> LENGTH: 110
<212> TYPE: PRT
<213> ORGANISM: Heterodontus francisci
<220> FEATURE:
<223> OTHER INFORMATION: >gi| 59892015| gb| AAX10139.1+51
      immunoglobulin NAR variable region, partial [Heterodontus
```

-continued francisci]

<400> SEQUENCE: 17

Ala Ser Leu Asp Gln Thr Pro Arg Thr Ala Thr Arg Glu Thr Gly Lys
1               5                   10                  15

Tyr Leu Asn Ile Asn Cys Val Leu Thr Asp Thr Arg Cys Gly Leu Tyr
            20                  25                  30

Gly Thr Ser Trp Phe Arg Asn Asn Pro Gly Ser Thr Asp Trp Glu Arg
        35                  40                  45

Ile Thr Ile Gly Arg Arg Tyr Val Glu Ser Val Asn Lys Gly Ala Lys
    50                  55                  60

Ser Phe Ser Leu Gln Ile Lys Asp Leu Thr Val Glu Asp Ser Val Thr
65                  70                  75                  80

Tyr Tyr Cys Lys Ala Gln Thr Gly Ser Phe Pro Cys Ser Glu Gly His
                85                  90                  95

Ser Tyr Tyr Tyr Asp Gly Ala Gly Thr Val Leu Thr Val Asn
            100                 105                 110

<210> SEQ ID NO 18
<211> LENGTH: 143
<212> TYPE: PRT
<213> ORGANISM: Ginglymostoma cirratum
<220> FEATURE:
<223> OTHER INFORMATION: >gi| 3982965| gb| AAC83733.1+51
      antigen receptor [Ginglymostoma cirratum]

<400> SEQUENCE: 18

Phe Thr Ala Arg Val Asp Gln Thr Pro Gln Thr Ile Thr Lys Glu Thr
1               5                   10                  15

Gly Glu Ser Leu Thr Ile Asn Cys Val Leu Arg Asp Ser Asn Cys Ala
            20                  25                  30

Leu Ser Ser Thr Tyr Trp Tyr Arg Lys Lys Ser Gly Ala Thr Asn Glu
        35                  40                  45

Glu Ser Ile Ser Lys Gly Gly Arg Tyr Val Glu Thr Val Asn Ser Gly
    50                  55                  60

Ser Lys Ser Phe Ser Leu Arg Ile Asn Asp Leu Thr Val Glu Asp Ser
65                  70                  75                  80

Gly Thr Tyr Arg Cys Lys Val Ala Gly Thr Ala Cys Arg Arg Phe Asn
                85                  90                  95

Val Tyr Gly Gly Gly Thr Val Val Thr Val Asn Pro Gly Ile Pro Leu
            100                 105                 110

Ser Pro Pro Ile Val Ser Leu Leu His Ser Ala Thr Glu Glu Gln Arg
        115                 120                 125

Ala Asn Gly Phe Val Gln Leu Val Cys Leu Ile Ser Gly Tyr Tyr
    130                 135                 140

<210> SEQ ID NO 19
<211> LENGTH: 103
<212> TYPE: PRT
<213> ORGANISM: Ginglymostoma cirratum
<220> FEATURE:
<223> OTHER INFORMATION: >gi| 21747962| gb| AAM76235.1+51
      antigen receptor [Ginglymostoma cirratum]

<400> SEQUENCE: 19

Arg Val Asp Gln Thr Pro Arg Ser Val Thr Lys Glu Thr Gly Glu Ser
1               5                   10                  15

Leu Thr Ile Asn Cys Val Leu Arg Asp Ala Ser Tyr Ala Leu Gly Ser
            20                  25                  30

```
Thr Cys Trp Tyr Arg Lys Lys Ser Gly Ser Thr Asn Glu Glu Ser Ile
            35                  40                  45

Ser Lys Gly Gly Arg Tyr Val Glu Thr Val Asn Ser Gly Ser Lys Ser
 50                  55                  60

Phe Ser Leu Arg Ile Asn Asp Leu Thr Val Glu Asp Gly Gly Thr Tyr
65                  70                  75                  80

Arg Cys Gly Ala Ala Val Gly Gly Leu Asp Ala Ala Cys Gly Asp Gly
                85                  90                  95

Thr Ala Val Thr Val Asn Pro
                100

<210> SEQ ID NO 20
<211> LENGTH: 105
<212> TYPE: PRT
<213> ORGANISM: Ginglymostoma cirratum
<220> FEATURE:
<223> OTHER INFORMATION: >gi| 21898882| gb| AAM77162.1+51
      antigen receptor [Ginglymostoma cirratum]

<400> SEQUENCE: 20

Arg Val Asp Gln Thr Pro Arg Ser Val Thr Lys Glu Thr Gly Glu Ser
1               5                   10                  15

Leu Thr Ile Asn Cys Val Leu Arg Asp Ala Ser Tyr Ala Leu Gly Ser
            20                  25                  30

Thr Cys Trp Tyr Arg Lys Lys Ser Gly Ser Thr Asn Glu Glu Ser Ile
            35                  40                  45

Ser Lys Gly Gly Arg Tyr Val Glu Thr Val Asn Ser Gly Ser Lys Ser
 50                  55                  60

Phe Ser Leu Arg Ile Asn Asp Leu Thr Val Glu Asp Ser Gly Thr Tyr
65                  70                  75                  80

Arg Cys Arg Ala Phe Leu Tyr Cys Gly Ala Glu Leu Asp Ser Phe Asp
                85                  90                  95

Glu Tyr Gly Gly Gly Thr Ile Val Thr
                100                 105

<210> SEQ ID NO 21
<211> LENGTH: 118
<212> TYPE: PRT
<213> ORGANISM: Ginglymostoma cirratum
<220> FEATURE:
<223> OTHER INFORMATION: >gi| 21805800| gb| AAM76806.1+51
      antigen receptor [Ginglymostoma cirratum]

<400> SEQUENCE: 21

Val Leu Leu Ala Leu Leu Pro Tyr Val Thr Val Arg Val Asp Gln Thr
1               5                   10                  15

Pro Gln Thr Ile Thr Lys Glu Thr Gly Glu Ser Leu Thr Ile Asn Cys
            20                  25                  30

Val Leu Arg Asp Thr Asn Cys Ala Leu Glu Gly Thr Tyr Trp Tyr Arg
            35                  40                  45

Lys Lys Ser Gly Ser Thr Asn Glu Glu Ser Ile Ser Lys Thr Gly Arg
 50                  55                  60

Tyr Val Glu Thr Val Asn Ser Gly Ser Lys Ser Phe Ser Leu Arg Ile
65                  70                  75                  80

Asn Asp Leu Thr Val Glu Asp Ser Gly Thr Tyr Arg Cys Lys Gly Arg
                85                  90                  95

Arg Ser Tyr Ser Cys Val Leu Gly Pro Asp Val Glu Gly Gly Gly Thr
                100                 105                 110
```

Val Val Thr Val Asn Pro
        115

<210> SEQ ID NO 22
<211> LENGTH: 120
<212> TYPE: PRT
<213> ORGANISM: Heterodontus francisci
<220> FEATURE:
<223> OTHER INFORMATION: >gi| 59892023| gb| AAX10143.1+51
      immunoglobulin NAR variable region, partial [Heterodontus
      francisci]

<400> SEQUENCE: 22

Ala Ser Leu Asp Gln Thr Pro Arg Thr Ala Thr Arg Glu Thr Gly Glu
1               5                   10                  15

Ser Leu Ser Ile Asn Cys Val Leu Thr Asp Thr Ser His Ile Leu Phe
            20                  25                  30

Gly Thr Lys Trp Phe Trp Asn Asn Pro Gly Ser Thr Asp Trp Glu Ser
        35                  40                  45

Ile Thr Ile Gly Gly Arg Tyr Val Glu Ser Val Asn Asn Gln Ala Lys
    50                  55                  60

Ser Phe Ser Leu Gln Ile Lys Asp Leu Thr Val Glu Asp Ser Gly Thr
65                  70                  75                  80

Tyr Tyr Cys Lys Ala Gln Thr Ile Gly Arg Arg Lys Gly Ala Gly Glu
                85                  90                  95

Leu Gly Glu His Glu Glu Leu Arg Trp Gly Thr Ser Asp Tyr Asp Gly
            100                 105                 110

Ala Gly Thr Val Leu Thr Val Asn
        115                 120

<210> SEQ ID NO 23
<211> LENGTH: 119
<212> TYPE: PRT
<213> ORGANISM: Ginglymostoma cirratum
<220> FEATURE:
<223> OTHER INFORMATION: >gi| 21805822| gb| AAM76817.1+51
      antigen receptor [Ginglymostoma cirratum]

<400> SEQUENCE: 23

Val Leu Leu Ala Leu Leu Pro Tyr Val Phe Ser Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Thr Asn Cys Ala Leu Ser Ser Thr Tyr Trp Tyr
        35                  40                  45

Arg Lys Lys Ser Gly Ser Thr Ser Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Ser Gly Thr Tyr Arg Cys Asn Val
                85                  90                  95

Trp Gly Trp Ser Tyr Asp Cys Gly Ala Ala Asp Val Tyr Gly Gly Gly
            100                 105                 110

Thr Val Val Thr Val Asn Pro
        115

<210> SEQ ID NO 24
<211> LENGTH: 115
<212> TYPE: PRT

-continued

```
<213> ORGANISM: Ginglymostoma cirratum
<220> FEATURE:
<223> OTHER INFORMATION: >gi| 21898926| gb| AAM77183.1+51
      antigen receptor [Ginglymostoma cirratum]

<400> SEQUENCE: 24
```

Ser Val Leu Leu Ala Leu Leu Pro Asn Val Phe Pro Ala Arg Val Asp
1               5                   10                  15

Gln Thr Pro Lys Thr Ile Thr Lys Glu Thr Gly Glu Ser Leu Thr Ile
            20                  25                  30

Asn Cys Val Leu Arg Asp Ser Asn Cys Ala Leu Ser Ser Thr Tyr Trp
        35                  40                  45

Tyr Arg Lys Lys Ser Gly Ser Thr Asn Glu Glu Ser Ile Ser Lys Gly
50                  55                  60

Gly Arg Tyr Val Glu Thr Val Asn Ser Gly Ser Lys Ser Phe Ser Leu
65                  70                  75                  80

Arg Ile Asn Asp Leu Thr Val Glu Asp Ser Gly Thr Tyr Arg Cys Asn
                85                  90                  95

Pro Trp Ser Thr Cys Tyr Asp Val Tyr Gly Gly Gly Thr Val Val Thr
            100                 105                 110

Val Asn Pro
        115

```
<210> SEQ ID NO 25
<211> LENGTH: 103
<212> TYPE: PRT
<213> ORGANISM: Orectolobus maculatus
<220> FEATURE:
<223> OTHER INFORMATION: >gi| 21655108| gb| AAL58520.1+51
      new antigen receptor variable domain [Orectolobus maculatus]

<400> SEQUENCE: 25
```

Thr Arg Val Asp Gln Thr Pro Arg Thr Ala Thr Lys Glu Thr Gly Glu
1               5                   10                  15

Ser Leu Thr Ile Asn Cys Val Leu Arg Asp Thr Ser Phe Pro Leu Asn
            20                  25                  30

Lys Thr Tyr Trp Tyr Arg Arg Phe Ser Ser Thr Asn Glu Gln His Ile
        35                  40                  45

Pro Ile Gly Gly Arg Tyr Val Glu Thr Val Asn Lys Arg Ser Lys Ser
50                  55                  60

Phe Ser Leu Arg Ile Ser Asp Leu Arg Val Glu Asp Ser Gly Thr Tyr
65                  70                  75                  80

Arg Cys Gly Ala Tyr Asn Leu Ser Gly Ile Tyr Tyr Ser Trp Gly Ala
                85                  90                  95

Gly Thr Ala Leu Thr Val Lys
            100

```
<210> SEQ ID NO 26
<211> LENGTH: 111
<212> TYPE: PRT
<213> ORGANISM: Orectolobus maculatus
<220> FEATURE:
<223> OTHER INFORMATION: >gi| 52696108| pdb| 1VER| A Chain A,
      Structure Of New Antigen Receptor Variable Domain From Sharks
      [Orectolobus maculatus]

<400> SEQUENCE: 26
```

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Tyr Gly Leu Glu

```
            20                  25                  30
Ser Thr Gly Trp Tyr Arg Thr Lys Leu Gly Ser Thr Asn Glu Gln Thr
            35                  40                  45

Ile Ser Ile Gly Gly Arg Tyr Val Glu Thr Val Asn Lys Gly Ser Lys
 50                  55                  60

Ser Phe Ser Leu Arg Ile Arg Asp Leu Arg Val Glu Asp Ser Gly Thr
 65                  70                  75                  80

Tyr Lys Cys Gly Ala Phe Arg Phe Trp Leu Pro Tyr Gly Tyr Gly Ser
                85                  90                  95

Leu Pro Leu Ser Glu Lys Gly Ala Gly Thr Val Leu Thr Val Lys
            100                 105                 110

<210> SEQ ID NO 27
<211> LENGTH: 141
<212> TYPE: PRT
<213> ORGANISM: Ginglymostoma cirratum
<220> FEATURE:
<223> OTHER INFORMATION: >gi| 3986584| gb| AAC84086.1+51
      antigen receptor [Ginglymostoma cirratum]

<400> SEQUENCE: 27

Asp Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Lys Val Leu Gly Gly Cys Trp Tyr Gly Pro Ser Ser Arg
                85                  90                  95

Glu Asn Trp Ile Gly Val Tyr Gly Gly Gly Thr Val Val Thr Val Asn
            100                 105                 110

Pro Gly Ile Pro Leu Ser Pro Pro Ile Val Ser Leu Leu His Ser Ala
            115                 120                 125

Thr Glu Glu Gln Arg Ala Asn Gly Phe Val Gln Leu Val
            130                 135                 140

<210> SEQ ID NO 28
<211> LENGTH: 138
<212> TYPE: PRT
<213> ORGANISM: Ginglymostoma cirratum
<220> FEATURE:
<223> OTHER INFORMATION: >gi| 3983003| gb| AAC83752.1+51
      antigen receptor [Ginglymostoma cirratum]

<400> SEQUENCE: 28

Arg Val Asp Gln Thr Pro Gln Thr Ile Thr Lys Glu Thr Gly Glu Ser
 1               5                  10                  15

Leu Thr Ile Asn Cys Val Leu Arg Asp Ser Asn Cys Ala Leu Ser Ser
            20                  25                  30

Thr Tyr Trp Tyr Arg Lys Lys Ser Gly Ser Thr Asn Glu Glu Ser Ile
            35                  40                  45

Ser Lys Gly Gly Arg Tyr Val Glu Thr Val Asn Ser Gly Ser Lys Ser
 50                  55                  60

Phe Ser Leu Arg Ile Asn Asp Leu Thr Val Glu Asp Ser Gly Thr Tyr
```

```
                65                  70                  75                  80
Arg Cys Asn Val Gln Tyr Met Tyr Cys Tyr Asp Val Tyr Gly Gly Gly
                    85                  90                  95

Thr Val Val Thr Val Asn Pro Gly Ile Pro Leu Ser Pro Pro Ile Val
                100                 105                 110

Ser Leu Leu His Ser Ala Thr Glu Glu Gln Arg Ala Asn Gly Phe Val
                115                 120                 125

Gln Leu Val Cys Leu Ile Ser Gly Tyr Tyr
            130                 135

<210> SEQ ID NO 29
<211> LENGTH: 167
<212> TYPE: PRT
<213> ORGANISM: Orectolobus maculatus
<220> FEATURE:
<223> OTHER INFORMATION: >gi| 15420366| gb| AAK97360.1+51
      new antigen receptor [Orectolobus maculatus]

<400> SEQUENCE: 29

Met Asn Ile Phe Leu Leu Ser Val Leu Leu Ala Leu Leu Pro Asn Val
1               5                   10                  15

Phe Thr Ala Arg Val Asp Gln Thr Pro Arg Thr Ala Thr Lys Glu Thr
                20                  25                  30

Gly Glu Ser Leu Thr Ile Asn Cys Val Leu Arg Asp Thr Ser Cys Ala
            35                  40                  45

Phe Ser Ser Thr Gly Trp Tyr Arg Thr Lys Leu Gly Ser Thr Asn Glu
        50                  55                  60

Gln Ser Ile Ser Ile Gly Gly Arg Tyr Val Glu Thr Val Asn Lys Gly
65                  70                  75                  80

Ser Lys Ser Phe Ser Leu Arg Ile Ser Asp Leu Arg Val Glu Asp Ser
                85                  90                  95

Gly Thr Tyr Lys Cys Gln Ala Tyr Val Ile Ala Thr Met Ala Pro Leu
                100                 105                 110

Cys Tyr Ala Ser Tyr Ser Trp Asn Glu Lys Gly Ala Gly Thr Val Leu
            115                 120                 125

Thr Val Lys Pro Gly Val Gln Pro Ser Pro Val Ile Ser Leu Leu
        130                 135                 140

Tyr Ser Ala Thr Glu Glu Gln Arg Gly Asn Gly Phe Val Gln Leu Ile
145                 150                 155                 160

Cys Leu Ile Ser Gly Tyr Tyr
            165

<210> SEQ ID NO 30
<211> LENGTH: 109
<212> TYPE: PRT
<213> ORGANISM: Heterodontus francisci
<220> FEATURE:
<223> OTHER INFORMATION: >gi| 59892029| gb| AAX10146.1+51
      immunoglobulin NAR variable region [Heterodontus francisci]

<400> SEQUENCE: 30

Ala Ser Leu Asp Gln Thr Pro Arg Thr Ala Thr Arg Glu Thr Gly Glu
1               5                   10                  15

Ser Leu Thr Val Ser Cys Ala Pro Val Asp Ala Arg Tyr Gly Ser Tyr
                20                  25                  30

Asn Thr Thr Trp Tyr Arg Asn Lys Pro Gly Ser Thr Asp Arg Glu His
            35                  40                  45

Ile Thr Ile Gly Gly Arg Tyr Val Glu Ser Leu Asn Lys Gly Ala Lys
```

```
                    50                  55                  60

Ala Val Lys Ser Phe Ser Leu Gln Ile Lys Asp Leu Thr Val Glu Asp
 65                  70                  75                  80

Ser Gly Thr Tyr Tyr Cys Lys Thr Ser Leu Ile Asp Ser Thr Ile Leu
                 85                  90                  95

Tyr Ala Leu Asp Gly Ala Gly Thr Val Leu Thr Val Asn
            100                 105
```

<210> SEQ ID NO 31
<211> LENGTH: 113
<212> TYPE: PRT
<213> ORGANISM: Heterodontus francisci
<220> FEATURE:
<223> OTHER INFORMATION: >gi| 59892025| gb| AAX10144.1+51
    immunoglobulin NAR variable region, partial [Heterodontus
    francisci]

<400> SEQUENCE: 31

```
Ala Arg Val Asp Gln Thr Pro Arg Thr Ala Thr Arg Glu Thr Gly Lys
 1               5                  10                  15

Ser Leu Ser Ile Asn Cys Val Leu Val Asp Ala Ser Cys Gly Leu Ser
                20                  25                  30

Gly Thr Ser Trp Phe Arg Asn Asn Pro Gly Ser Thr Asp Trp Glu Arg
             35                  40                  45

Ile Thr Ile Gly Gly Arg Tyr Val Glu Ser Val Asn Lys Gly Ala Lys
 50                  55                  60

Ser Phe Ser Leu Gln Ile Lys Asp Leu Thr Val Glu Asp Ser Val Thr
 65                  70                  75                  80

Tyr Tyr Cys Arg Ala Gln Thr Ser Val Glu Leu Gly Met Gly Pro Arg
                 85                  90                  95

Ala Cys Glu Val Gly Tyr Ser His Tyr Tyr Asp Gly Ala Gly Thr Val
            100                 105                 110

Asp
```

<210> SEQ ID NO 32
<211> LENGTH: 109
<212> TYPE: PRT
<213> ORGANISM: Ginglymostoma cirratum
<220> FEATURE:
<223> OTHER INFORMATION: >gi| 25987461| gb| AAN75857.1+51
    AF447101_1 novel antigen receptor [Ginglymostoma cirratum]

<400> SEQUENCE: 32

```
Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Gly Gly Thr
 65                  70                  75                  80

Tyr Arg Cys Gly Ala Arg Ala Gly Gly Pro Phe Leu Cys Ser Cys Val
                 85                  90                  95

Tyr Ala Ala Cys Gly Asp Gly Thr Ala Val Thr Val Asn
            100                 105
```

<210> SEQ ID NO 33
<211> LENGTH: 121
<212> TYPE: PRT
<213> ORGANISM: Ginglymostoma cirratum
<220> FEATURE:
<223> OTHER INFORMATION: >gi| 21898887| gb| AAM77164.1+51
      antigen receptor [Ginglymostoma cirratum]

<400> SEQUENCE: 33

Val Leu Leu Ala Leu Leu Pro Tyr Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Ser Asn Cys Ala Leu Ser Ser Thr Tyr Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Ser Gly Thr Tyr Arg Cys Lys Val
                85                  90                  95

Gly Gly Gly Tyr Pro Leu Trp Arg Arg Gly Tyr Asp Val Tyr Gly Gly
            100                 105                 110

Gly Thr Val Val Thr Val Asn Pro Gly
        115                 120

<210> SEQ ID NO 34
<211> LENGTH: 114
<212> TYPE: PRT
<213> ORGANISM: Ginglymostoma cirratum
<220> FEATURE:
<223> OTHER INFORMATION: >gi| 21898924| gb| AAM77182.1+51
      antigen receptor [Ginglymostoma cirratum]

<400> SEQUENCE: 34

Val Leu Leu Ala Leu Leu Pro Tyr Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Ser Asn Cys Ala Leu Ser Ser Thr Tyr Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Ser Gly Thr Tyr Arg Cys Asn Pro
                85                  90                  95

Trp Ser Thr Cys Tyr Asp Val Tyr Gly Gly Thr Val Val Thr Val
            100                 105                 110

Asn Pro

<210> SEQ ID NO 35
<211> LENGTH: 143
<212> TYPE: PRT
<213> ORGANISM: Ginglymostoma cirratum
<220> FEATURE:
<223> OTHER INFORMATION: >gi| 3983053| gb| AAC83777.1+51
      antigen receptor [Ginglymostoma cirratum]

<400> SEQUENCE: 35

```
Thr Asn Gln Leu Asp Arg Val Asp Gln Thr Pro Gln Thr Ile Thr Lys
1               5                   10                  15

Glu Thr Gly Glu Ser Leu Thr Ile Asn Cys Val Leu Arg Asp Ser Asn
            20                  25                  30

Cys Ala Leu Ser Ser Thr Tyr Trp Tyr Arg Lys Lys Ser Gly Ser Thr
        35                  40                  45

Asn Glu Glu Ser Ile Ser Lys Gly Gly Arg Tyr Val Glu Thr Val Asn
    50                  55                  60

Ser Gly Ser Lys Ser Phe Ser Leu Arg Ile Asn Asp Leu Thr Val Glu
65                  70                  75                  80

Asp Ser Gly Thr Tyr Arg Cys Lys Val Tyr Arg His Ser Ala Gly Met
                85                  90                  95

Ser Leu Cys Leu Gly Gly Phe Leu Tyr Gly Gly Gly Thr Val Val Thr
            100                 105                 110

Val Asn Pro Gly Ile Pro Leu Ser Pro Pro Ile Val Ser Leu Leu His
            115                 120                 125

Ser Ala Thr Glu Glu Gln Arg Ala Asn Gly Phe Val Gln Leu Val
            130                 135                 140

<210> SEQ ID NO 36
<211> LENGTH: 109
<212> TYPE: PRT
<213> ORGANISM: Ginglymostoma cirratum
<220> FEATURE:
<223> OTHER INFORMATION: >gi| 21539902| gb| AAM52938.1+51
      antigen receptor [Ginglymostoma cirratum]

<400> SEQUENCE: 36

Val Phe Thr Ala Arg Val Asp Gln Thr Pro Gln Thr Ile Thr Lys Glu
1               5                   10                  15

Thr Gly Glu Ser Leu Thr Ile Asn Cys Val Leu Arg Asp Ser Asn Cys
            20                  25                  30

Ala Leu Ser Ser Thr Tyr Trp Tyr Arg Lys Lys Ser Gly Ser Thr Asn
        35                  40                  45

Glu Glu Ser Ile Ser Lys Gly Gly Arg Tyr Val Glu Thr Val Asn Ser
    50                  55                  60

Gly Ser Lys Ser Phe Ser Leu Arg Ile Asn Asp Leu Thr Val Glu Asp
65                  70                  75                  80

Ser Gly Thr Tyr Arg Cys Lys Val Asp Arg Ile Gly Ser Trp Tyr Gly
                85                  90                  95

Asp Cys His Trp Asp Val Tyr Gly Gly Gly Thr Val Val
            100                 105

<210> SEQ ID NO 37
<211> LENGTH: 673
<212> TYPE: PRT
<213> ORGANISM: Triakis scyllium
<220> FEATURE:
<223> OTHER INFORMATION: >gi| 307685089| dbj| BAJ20186.1+
      51 immunoglobulin NAR [Triakis scyllium]

<400> SEQUENCE: 37

Met His Ile Phe Trp Ala Ala Leu Leu Leu Thr Trp Leu Ser Asn Ala
1               5                   10                  15

Phe Ser Ala His Val Asp Gln Thr Pro Arg Val Ala Thr Lys Gly Thr
            20                  25                  30

Gly Glu Ser Leu Thr Ile Asn Cys Val Leu Arg Gly Ala Arg Asn Gly
            35                  40                  45
```

```
Leu Tyr Ala Thr Ser Trp Phe Arg Gln Asn Pro Gly Ser Thr Gly Trp
 50              55                  60

Glu Arg Met Thr Ile Gly Gly Arg Tyr Ile Glu Ser Val Thr Lys Gly
 65              70                  75                  80

Asn Lys Ser Phe Ser Leu Gln Ile Lys Asp Leu Thr Val Glu Asp Ser
                 85                  90                  95

Val Thr Phe Tyr Cys Lys Ala Gln Gly Asp Thr Thr Trp Gly Leu Ala
                100                 105                 110

Ser Asp Asp Tyr Tyr Asp Gly Ala Gly Thr Val Leu Thr Val Asn Pro
            115                 120                 125

Gly Pro Thr Pro Pro Ile Ile Asn Leu Phe Ser Glu Thr Asp Glu Leu
130                 135                 140

Arg Ala Lys Gly Phe Val Gln Leu Ile Cys Leu Ile Ser Glu Tyr Lys
145                 150                 155                 160

Pro Glu Ser Ile Arg Val Ser Trp Glu Lys Asn Gly Asn Ala Arg Gln
                165                 170                 175

Ser Gly Phe Thr Thr Thr Ser Pro Cys Lys Thr Ala Lys Gly Glu Phe
            180                 185                 190

Gln Ser Arg Ser Ile Leu Thr Leu Pro Leu Gln Glu Trp Asn Ser Gly
            195                 200                 205

Ser Thr Tyr Ser Cys Gln Val Thr His Ser Ala Thr Asn Ser Asn Lys
210                 215                 220

Arg Lys Glu Ile Arg Ser Thr Ser Glu Ile Thr Val Phe Leu Arg Asp
225                 230                 235                 240

Pro Ser Leu Glu Glu Ile Trp Ile Lys Lys Thr Val Thr Leu Ile Cys
                245                 250                 255

Glu Val Val Ser Thr Val Pro Ser Val Val Gly Ile Ser Trp Thr Val
            260                 265                 270

Asp Gly Lys Lys Arg Thr Glu Gly Val Gln Ile Glu Gly Arg Gln Gln
            275                 280                 285

Gly Gln Asn Gln Tyr Leu Thr Ile Ser Arg Leu Thr Ser Gly Val Glu
290                 295                 300

Glu Trp Asp Arg Gly Ala Glu Tyr Asn Cys Ser Ala Gln Gln Ser Glu
305                 310                 315                 320

Ser Ser Thr Pro Val Ser Lys His Thr Gln Lys Leu Lys Val Lys Pro
                325                 330                 335

Ser Lys Pro Asn Leu Arg Leu Leu Pro Ser Ala Glu Glu Leu Gln
                340                 345                 350

Ser Ser Ser Val Ala Thr Leu Thr Cys Leu Ile Arg Gly Phe Tyr Pro
            355                 360                 365

Asp Lys Ile Ser Ile Ser Trp Glu Lys Asp Gly Ala Val Leu Ser Ser
370                 375                 380

Asn Ile Thr Arg Phe Pro Thr Ala Leu Glu Gln Asp Gln Thr Phe Ser
385                 390                 395                 400

Thr Ser Ser Leu Leu Ile Leu Pro Ala Gly Glu Trp Lys Thr Gly Ala
                405                 410                 415

Arg Tyr Thr Cys Thr Ala Ser His Pro Ala Thr Lys Phe Thr Gly Lys
            420                 425                 430

Arg Thr Ile Asn Ser Pro Lys Ala Asp Cys Tyr Glu Glu Asp Ile Ser
                435                 440                 445

Val Asn Ile Leu Asn Pro Ser Phe Glu Glu Ile Trp Ile Gln Lys Thr
450                 455                 460

Ala Thr Ile Val Cys Glu Ile Arg Tyr Thr Val Leu Glu Asn Val Ser
```

```
                465                 470                 475                 480
Val Ser Trp Gln Val Asp Gly Arg Met Arg Thr Glu Gly Val Glu Thr
                    485                 490                 495

Gln Thr Pro Glu Trp Ser Gly Ser Lys Thr Thr Ile Met Ser Lys Leu
                500                 505                 510

Lys Ala Thr Ala Ala Glu Trp Asp Thr Gly Val Glu Tyr Val Cys Leu
                515                 520                 525

Ala Glu Gly Ser Glu Leu Pro Thr Pro Lys Lys Arg Ser Thr Arg Lys
            530                 535                 540

Ile Lys Val Gly Ala Met Asn Ser Pro Lys Val Tyr Ile Leu Pro Pro
545                 550                 555                 560

Ser Val Ala Glu Ile Asp Ser Glu Lys Thr Ala Thr Leu Met Cys Leu
                    565                 570                 575

Ala Thr Gly Phe Tyr Pro Ala Glu Ile Tyr Ile Ala Trp Leu Ala Asn
                580                 585                 590

Asp Thr Leu Leu Asp Ser Asp Phe Pro Asn Gln Pro Val Ser Glu Lys
            595                 600                 605

Gly Asn Gly Ser Ser Phe Ile Ala Ser Arg Leu Arg Leu Thr Ala Ala
        610                 615                 620

Glu Trp Asn Thr Gly Thr Thr Tyr Ser Cys Leu Val Gly His Pro Ser
625                 630                 635                 640

Leu Glu Arg Asn Leu Ile Arg Ser Ile Asn Lys Ser Tyr Gly Lys Pro
                    645                 650                 655

Thr Leu Val Asn Val Ser Leu Ala Leu Ala Asp Ser Phe Thr Ser Cys
                660                 665                 670

Ala

<210> SEQ ID NO 38
<211> LENGTH: 142
<212> TYPE: PRT
<213> ORGANISM: Ginglymostoma cirratum
<220> FEATURE:
<223> OTHER INFORMATION: >gi| 3986580| gb| AAC84084.1+51
      antigen receptor [Ginglymostoma cirratum]

<400> SEQUENCE: 38

Tyr Val Phe Thr Ala Arg Val Asp Gln Thr Pro Gln Thr Ile Thr Lys
1               5                   10                  15

Glu Thr Gly Glu Ser Leu Thr Ile Asn Cys Val Leu Arg Asp Ser Asn
                20                  25                  30

Cys Ala Leu Ser Ser Thr Tyr Trp Tyr Arg Lys Lys Ser Gly Ser Thr
            35                  40                  45

Asn Glu Glu Ser Ile Ser Lys Gly Gly Arg Tyr Val Glu Thr Val Asn
        50                  55                  60

Ser Gly Ser Lys Ser Phe Ser Leu Arg Ile Asn Asp Leu Thr Val Glu
65                  70                  75                  80

Asp Ser Gly Thr Tyr Arg Cys Lys Val Ala Gly Thr Val Tyr Asp Cys
                85                  90                  95

Lys Pro Pro Asn Trp Thr His Tyr Asn Val Tyr Gly Gly Thr Val
                100                 105                 110

Val Thr Val Asn Pro Gly Ile Pro Leu Ser Pro Ile Val Ser Leu
            115                 120                 125

Leu His Ser Ala Thr Glu Glu Gln Arg Ala Asn Gly Phe Val
        130                 135                 140
```

```
<210> SEQ ID NO 39
<211> LENGTH: 111
<212> TYPE: PRT
<213> ORGANISM: Orectolobus maculatus
<220> FEATURE:
<223> OTHER INFORMATION: >gi| 126009471| gb| ABN64030.1+51
      antigen receptor variable domain [Orectolobus maculatus]

<400> SEQUENCE: 39

Ala Arg Val Asp Gln Thr Pro Arg Thr Ala Thr Lys Glu Thr Gly Glu
1               5                   10                  15

Ser Leu Thr Ile Asn Cys Val Leu Arg Asp Thr Ser Tyr Gly Leu Glu
            20                  25                  30

Ser Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Arg Gly Thr
65                  70                  75                  80

Tyr Lys Cys Gly Ala Ser Ala Leu Ser Pro Asn Ser Tyr Tyr Cys
                85                  90                  95

Pro Ser Cys Leu Glu Lys Gly Ala Gly Thr Ala Leu Thr Val Lys
            100                 105                 110

<210> SEQ ID NO 40
<211> LENGTH: 111
<212> TYPE: PRT
<213> ORGANISM: Ginglymostoma cirratum
<220> FEATURE:
<223> OTHER INFORMATION: >gi| 25987459| gb| AAN75856.1+51
      AF447100_1 novel antigen receptor [Ginglymostoma cirratum]

<400> SEQUENCE: 40

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Cys Pro His Phe Ser Trp Cys Arg Leu His Glu
                85                  90                  95

Gln Cys Ala Leu Ala Gly Gly Asp Gly Thr Ala Val Thr Val Asn
            100                 105                 110

<210> SEQ ID NO 41
<211> LENGTH: 679
<212> TYPE: PRT
<213> ORGANISM: Triakis scyllium
<220> FEATURE:
<223> OTHER INFORMATION: >gi| 307685093| dbj| BAJ20188.1+
      51  immunoglobulin NAR [Triakis scyllium]

<400> SEQUENCE: 41

Met His Ile Phe Trp Ala Ala Leu Leu Leu Thr Trp Leu Ser Asn Ala
1               5                   10                  15

Phe Ser Ala His Val Asp Gln Thr Pro Arg Val Ala Thr Lys Glu Thr
            20                  25                  30
```

```
Gly Glu Ser Leu Thr Ile Asn Cys Val Leu Arg Gly Val Ser Cys Gly
            35                  40                  45

Leu Tyr Ala Thr Arg Trp Phe Arg Gln Asn Pro Gly Ser Thr Ser Trp
        50                  55                  60

Glu Arg Ile Thr Ile Gly Gly Arg Tyr Val Glu Ser Val Asn Lys Gly
65                  70                  75                  80

Ser Lys Ser Phe Ser Leu Gln Ile Lys Asp Leu Thr Val Glu Asp Ser
                85                  90                  95

Val Thr Phe Tyr Cys Lys Ala Gln Glu Asn Thr Glu Glu Tyr Tyr Val
            100                 105                 110

Gly Asp Arg Arg Cys Ser Arg Ser Asn Tyr Tyr Asp Gly Thr Gly Thr
            115                 120                 125

Val Met Thr Val Asn Pro Gly Pro Thr Pro Ile Ile Asn Leu Phe
        130                 135                 140

Ser Glu Thr Asp Glu Leu Arg Ala Lys Gly Phe Val Gln Leu Ile Cys
145                 150                 155                 160

Leu Ile Ser Glu Tyr Lys Pro Glu Ser Ile Arg Val Ser Trp Glu Lys
                165                 170                 175

Asn Gly Asn Ala Arg Gln Ser Gly Phe Thr Thr Thr Ser Pro Cys Lys
            180                 185                 190

Thr Ala Lys Gly Glu Phe Gln Ser Arg Ser Ile Leu Thr Leu Pro Leu
            195                 200                 205

Gln Glu Trp Asn Ser Gly Ser Thr Tyr Ser Cys Gln Val Thr His Ser
        210                 215                 220

Ala Thr Asn Ser Asn Lys Arg Lys Glu Ile Arg Ser Ser Glu Ile
225                 230                 235                 240

Thr Val Phe Leu Arg Asp Pro Ser Leu Glu Glu Ile Trp Ile Lys Lys
            245                 250                 255

Thr Val Thr Leu Ile Cys Glu Val Val Ser Thr Val Pro Ser Val Val
            260                 265                 270

Gly Ile Ser Trp Thr Val Asp Gly Lys Lys Arg Thr Glu Gly Val Gln
            275                 280                 285

Ile Glu Gly Arg Gln Gly Gln Asn Gln Tyr Leu Thr Ile Ser Arg
        290                 295                 300

Leu Thr Ser Ser Val Glu Glu Trp Asp Arg Gly Ala Glu Tyr Asn Cys
305                 310                 315                 320

Ser Ala Gln Gln Ser Glu Ser Ser Thr Pro Val Ser Lys His Thr Gln
            325                 330                 335

Lys Leu Lys Val Lys Pro Ser Lys Pro Asn Leu Arg Leu Leu Pro Pro
            340                 345                 350

Ser Ala Glu Glu Leu Gln Ser Ser Val Ala Thr Leu Thr Cys Leu
        355                 360                 365

Ile Arg Gly Phe Tyr Pro Asp Lys Ile Ser Ile Ser Trp Glu Lys Asp
        370                 375                 380

Gly Ala Val Leu Ser Ser Asn Ile Thr Arg Phe Pro Thr Ala Leu Glu
385                 390                 395                 400

Gln Asp Gln Thr Phe Ser Thr Ser Ser Leu Leu Ile Leu Pro Ala Gly
            405                 410                 415

Glu Trp Lys Thr Gly Ala Arg Tyr Thr Cys Thr Ala Ser His Pro Ala
            420                 425                 430

Ser Lys Phe Thr Gly Lys Arg Thr Ile Asn Ser Pro Lys Ala Asp Cys
            435                 440                 445
```

```
Tyr Glu Glu Asp Ile Ser Val Asn Ile Leu Asn Pro Ser Phe Glu Glu
    450                 455                 460

Ile Trp Val Gln Lys Thr Ala Thr Ile Val Cys Glu Ile Arg Tyr Thr
465                 470                 475                 480

Val Leu Glu Asn Val Ser Val Ser Trp Gln Val Asp Gly Arg Met Arg
                485                 490                 495

Thr Glu Gly Val Glu Thr Gln Thr Pro Glu Trp Ser Gly Ser Lys Thr
            500                 505                 510

Thr Ile Met Ser Lys Leu Lys Val Thr Ala Ala Glu Trp Asp Thr Gly
        515                 520                 525

Val Glu Tyr Val Cys Leu Ala Glu Gly Ser Glu Leu Pro Thr Pro Lys
    530                 535                 540

Lys Arg Ser Thr Arg Lys Ile Lys Val Gly Ala Met Asn Ser Pro Lys
545                 550                 555                 560

Val Tyr Ile Leu Pro Pro Ser Val Ala Glu Ile Asp Ser Glu Lys Thr
                565                 570                 575

Ala Thr Leu Met Cys Leu Ala Thr Gly Phe Tyr Pro Ala Glu Ile Tyr
            580                 585                 590

Ile Ala Trp Leu Ala Asn Asp Thr Leu Leu Asp Ser Asp Phe Pro Asn
        595                 600                 605

Gln Pro Val Ser Glu Lys Gly Asn Gly Ser Ser Phe Ile Ala Ser Arg
    610                 615                 620

Leu Arg Leu Thr Ala Ala Glu Trp Asn Thr Gly Thr Thr Tyr Ser Cys
625                 630                 635                 640

Leu Val Gly His Pro Ser Leu Glu Arg Asn Leu Ile Arg Ser Ile Asn
                645                 650                 655

Lys Ser Tyr Gly Lys Pro Thr Leu Val Asn Val Ser Leu Ala Leu Ala
            660                 665                 670

Asp Ser Phe Thr Ser Cys Ala
            675

<210> SEQ ID NO 42
<211> LENGTH: 123
<212> TYPE: PRT
<213> ORGANISM: Ginglymostoma cirratum
<220> FEATURE:
<223> OTHER INFORMATION: >gi| 21748031| gb| AAM76269.1+51
      antigen receptor [Ginglymostoma cirratum]

<400> SEQUENCE: 42

Val Leu Leu Ala Leu Leu Pro Tyr Val Phe Thr Ala Arg Val Asp Gln
1               5                   10                  15

Thr Pro Arg Ser Val Thr Lys Glu Thr Gly Glu Ser Leu Thr Ile Asn
                20                  25                  30

Cys Val Leu Arg Asp Ala Ser Tyr Ala Leu Gly Ser Thr Cys Trp Tyr
            35                  40                  45

Arg Lys Lys Ser Gly Ser Thr Asn Glu Glu Ser Ile Ser Lys Gly Gly
        50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Thr Tyr Arg Cys Gly Val
                85                  90                  95

Ala Gly Gly Arg Phe Cys Glu Gly Arg Cys Ser Gly Pro Tyr Ala Ala
            100                 105                 110

Cys Gly Asp Gly Thr Ala Val Thr Val Asn Pro
            115                 120
```

<210> SEQ ID NO 43
<211> LENGTH: 98
<212> TYPE: PRT
<213> ORGANISM: Ginglymostoma cirratum
<220> FEATURE:
<223> OTHER INFORMATION: >gi| 3986664| gb| AAC84126.1+51
      antigen receptor [Ginglymostoma cirratum]

<400> SEQUENCE: 43

Arg Val Asp Gln Thr Pro Gln Thr Ile Thr Lys Glu Thr Gly Glu Ser
1               5                   10                  15

Leu Thr Ile Asn Cys Val Leu Arg Asp Ser Asn Cys Ala Leu Ser Ser
            20                  25                  30

Thr Tyr Trp Tyr Arg Lys Lys Ser Gly Ser Thr Asn Glu Glu Ser Ile
        35                  40                  45

Ser Lys Gly Gly Arg Tyr Val Glu Thr Val Asn Ser Gly Ser Lys Ser
    50                  55                  60

Phe Ser Leu Arg Ile Asn Asp Leu Thr Val Glu Asp Ser Gly Thr Tyr
65                  70                  75                  80

Arg Cys Lys Val Ala Gly Thr Ala Cys Arg Arg Ser Asn Val Tyr Gly
                85                  90                  95

Gly Gly

<210> SEQ ID NO 44
<211> LENGTH: 143
<212> TYPE: PRT
<213> ORGANISM: Ginglymostoma cirratum
<220> FEATURE:
<223> OTHER INFORMATION: >gi| 3982949| gb| AAC83725.1+51
      antigen receptor [Ginglymostoma cirratum]

<400> SEQUENCE: 44

Ala Arg Val Asp Gln Thr Pro Gln Thr Ile Thr Lys Glu Thr Gly Glu
1               5                   10                  15

Ser Leu Thr Met Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Ala Ser Thr Gly Leu Asp Cys Arg Leu Tyr Tyr Asn
                85                  90                  95

Val Tyr Gly Gly Gly Thr Val Val Thr Val Asn Pro Gly Ile Pro Leu
                100                 105                 110

Ser Pro Pro Ile Val Ser Leu Leu His Ser Ala Thr Glu Glu Gln Arg
            115                 120                 125

Ala Asn Gly Phe Val Gln Leu Val Cys Leu Ile Ser Gly Tyr Tyr
        130                 135                 140

<210> SEQ ID NO 45
<211> LENGTH: 119
<212> TYPE: PRT
<213> ORGANISM: Ginglymostoma cirratum
<220> FEATURE:
<223> OTHER INFORMATION: >gi| 21885446| gb| AAM76964.1+51
      antigen receptor [Ginglymostoma cirratum]

<400> SEQUENCE: 45

```
Val Leu Leu Ala Leu Leu Pro Tyr Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Ala Ser Tyr Ala Leu Gly Ser Thr Cys Trp Tyr
        35                  40                  45

Arg Lys Lys Ser Gly Ser Thr Asn Glu Glu Ser Ile Ser Lys Gly Gly
    50                  55                  60

Arg Tyr Val Glu Ala Val Asn Ser Gly Ser Lys Ser Phe Ser Met Arg
65                  70                  75                  80

Ile Asn Asp Leu Thr Val Glu Asp Ser Gly Thr Phe Arg Cys Gly Val
                85                  90                  95

Cys Trp Ser Arg Cys Asp Arg Ala Pro Val Ala Ala Cys Gly Gly Gly
            100                 105                 110

Thr Val Val Thr Val Asn Pro
        115
```

<210> SEQ ID NO 46
<211> LENGTH: 108
<212> TYPE: PRT
<213> ORGANISM: Orectolobus maculatus
<220> FEATURE:
<223> OTHER INFORMATION: >gi| 21069163| gb| AAM33846.1+51
    AF466396_1 new antigen receptor variable domain [Orectolobus
    maculatus]

<400> SEQUENCE: 46

```
Ala Trp Val Asp Gln Thr Pro Arg Thr Val Thr Lys Glu Thr Gly Glu
1               5                   10                  15

Ser Leu Thr Ile Asn Cys Val Leu Arg Asp Thr Ala Cys Pro Leu Asp
            20                  25                  30

Ser Thr Asn Trp Tyr Arg Thr Lys Leu Gly Ser Thr Asn Glu Gln Thr
        35                  40                  45

Ile Ser Ile Gly Gly Arg Tyr Val Glu Thr Val Ser Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Lys Ala Tyr Arg Gly Cys Gly Phe Thr Arg Gly Val Glu
                85                  90                  95

Tyr Leu Lys Gly Ala Gly Thr Val Leu Thr Val Lys
            100                 105
```

<210> SEQ ID NO 47
<211> LENGTH: 114
<212> TYPE: PRT
<213> ORGANISM: Ginglymostoma cirratum
<220> FEATURE:
<223> OTHER INFORMATION: >gi| 21898928| gb| AAM77184.1+51
    antigen receptor [Ginglymostoma cirratum]

<400> SEQUENCE: 47

```
Val Leu Leu Ala Leu Leu Pro Tyr Val Phe Thr Ala Arg Val Asp Gln
1               5                   10                  15

Thr Pro Gln Thr Ile Thr Lys Glu Ala Gly Glu Ser Leu Thr Ile Asn
            20                  25                  30

Cys Val Leu Arg Asp Ser Asn Cys Ala Leu Ser Ser Thr Tyr Trp Tyr
        35                  40                  45
```

Arg Lys Lys Ser Gly Ser Thr Asn Glu Glu Ser Ile Ser Glu Gly Gly
 50                  55                  60

Arg Tyr Val Glu Thr Val Asn Ser Gly Ser Lys Ser Phe Ser Leu Arg
 65                  70                  75                  80

Ile Asn Asp Leu Thr Val Glu Asp Ser Gly Tyr Arg Cys Asn Pro
                 85                  90                  95

Trp Ser Thr Cys Tyr Asp Val Tyr Gly Gly Thr Val Val Thr Val
                100                 105                 110

Asn Pro

<210> SEQ ID NO 48
<211> LENGTH: 121
<212> TYPE: PRT
<213> ORGANISM: Ginglymostoma cirratum
<220> FEATURE:
<223> OTHER INFORMATION: >gi| 21885420| gb| AAM76954.1+51
      antigen receptor [Ginglymostoma cirratum]

<400> SEQUENCE: 48

Ala Ser Val Leu Leu Ala Leu Leu Pro Tyr Val Phe Thr Ala Arg Val
 1               5                  10                  15

Asp Gln Thr Pro Gln Thr Ile Thr Lys Glu Thr Gly Glu Ser Leu Thr
                 20                  25                  30

Ile Asn Cys Val Leu Arg Asp Ser Asn Cys Ala Leu Ser Ser Thr Tyr
             35                  40                  45

Trp Tyr Arg Lys Lys Ser Gly Ser Thr Asn Glu Glu Ser Ile Ser Lys
 50                  55                  60

Gly Gly Arg Tyr Val Glu Thr Val Asn Ser Gly Ser Lys Ser Phe Ser
 65                  70                  75                  80

Leu Arg Ile Asn Asp Leu Thr Val Glu Asp Ser Gly Tyr Arg Cys
                 85                  90                  95

Lys Val Pro Leu Val Ile Glu Leu Glu Ile Pro Tyr Asp Val Tyr Gly
                100                 105                 110

Gly Gly Thr Val Val Thr Val Asn Pro
            115                 120

<210> SEQ ID NO 49
<211> LENGTH: 127
<212> TYPE: PRT
<213> ORGANISM: Ginglymostoma cirratum
<220> FEATURE:
<223> OTHER INFORMATION: >gi| 21748025| gb| AAM76266.1+51
      antigen receptor [Ginglymostoma cirratum]

<400> SEQUENCE: 49

Val Leu Leu Ala Leu Leu Pro Tyr Val Phe Thr Ala Arg Val Asp Gln
 1               5                  10                  15

Thr Pro Arg Ser Val Thr Lys Glu Thr Gly Glu Ser Leu Thr Ile Asn
                 20                  25                  30

Cys Val Leu Arg Asp Ala Ser Tyr Ala Leu Gly Ser Thr Cys Trp Tyr
             35                  40                  45

Arg Lys Lys Ser Gly Ser Thr Asn Glu Glu Asn Ile Ser Lys Gly Gly
 50                  55                  60

Arg Tyr Val Glu Thr Val Asn Ser Gly Ser Lys Ser Phe Ser Leu Arg
 65                  70                  75                  80

Ile Asn Asp Leu Thr Val Glu Asp Gly Gly Thr Tyr Arg Cys Gly Val
                 85                  90                  95

Cys Ala Gly Asn Ser Cys Asp Tyr Gln Leu Cys Ser Cys Leu Tyr Ala

```
                100             105             110
Ala Cys Gly Asp Gly Thr Ala Val Thr Val Asn Pro Gly Ile Pro
            115                 120                 125

<210> SEQ ID NO 50
<211> LENGTH: 120
<212> TYPE: PRT
<213> ORGANISM: Ginglymostoma cirratum
<220> FEATURE:
<223> OTHER INFORMATION: >gi| 21748015| gb| AAM76261.1+51
      antigen receptor [Ginglymostoma cirratum]

<400> SEQUENCE: 50

Val Leu Leu Ala Leu Leu Pro Tyr Val Phe Thr Ala Arg Val Asp Gln
1               5                   10                  15

Thr Pro Arg Ser Val Thr Lys Glu Thr Gly Glu Ser Leu Thr Ile Asn
            20                  25                  30

Cys Val Leu Arg Asp Ala Ser Tyr Ala Leu Gly Ser Thr Cys Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Gly Thr Tyr Arg Cys Gly Val
                85                  90                  95

Asp Leu Gly Ser Cys Gly Gly Cys Ser Arg Tyr Ala Ala Cys Gly Asp
            100                 105                 110

Gly Thr Ala Val Thr Val Asn Pro
            115                 120

<210> SEQ ID NO 51
<211> LENGTH: 119
<212> TYPE: PRT
<213> ORGANISM: Ginglymostoma cirratum
<220> FEATURE:
<223> OTHER INFORMATION: >gi| 21539976| gb| AAM52972.1+51
      antigen receptor [Ginglymostoma cirratum]

<400> SEQUENCE: 51

Val Leu Leu Ala Leu Leu Pro Tyr Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Ser Asn Cys Ala Leu Ser Ser Thr Tyr Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Ser Gly Thr Tyr Arg Cys Asn Val
                85                  90                  95

Tyr Ser Trp Tyr Gly Tyr Asp Cys Ala Glu Leu Asp Val Tyr Gly Gly
            100                 105                 110

Gly Thr Val Val Thr Val Asn
            115

<210> SEQ ID NO 52
<211> LENGTH: 122
<212> TYPE: PRT
```

<213> ORGANISM: Ginglymostoma cirratum
<220> FEATURE:
<223> OTHER INFORMATION: >gi| 21747995| gb| AAM76251.1+51
     antigen receptor [Ginglymostoma cirratum]

<400> SEQUENCE: 52

Val Leu Leu Ala Leu Leu Pro Tyr Val Phe Thr Ala Arg Val Asp Gln
1               5                   10                  15

Thr Pro Arg Ser Val Thr Lys Glu Thr Gly Glu Ser Leu Thr Ile Asn
            20                  25                  30

Cys Val Leu Arg Asp Ala Ser Tyr Ala Leu Gly Arg Thr Cys Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Gly Thr Tyr Arg Cys Gly Ala
                85                  90                  95

Ala Gly Arg Tyr Ser Cys Asp Tyr Glu Leu Cys Leu Tyr Ala Ala Cys
            100                 105                 110

Gly Asp Gly Thr Ala Val Thr Val Asn Pro
        115                 120

<210> SEQ ID NO 53
<211> LENGTH: 125
<212> TYPE: PRT
<213> ORGANISM: Ginglymostoma cirratum
<220> FEATURE:
<223> OTHER INFORMATION: >gi| 21805816| gb| AAM76814.1+51
     antigen receptor [Ginglymostoma cirratum]

<400> SEQUENCE: 53

Val Leu Leu Ala Leu Leu Pro Tyr Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Ser Asn Cys Ala Leu Ser Ser Thr Tyr Trp Tyr
        35                  40                  45

Arg Lys Lys Ser Gly Ser Thr Asn Glu Glu Asn Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Ser Gly Thr Tyr Arg Cys Asn Val
                85                  90                  95

Tyr Ala Ala Gly Ile Pro His Ser Tyr Asp Cys Ala Asn Arg Phe Tyr
            100                 105                 110

Asp Val Tyr Gly Gly Gly Thr Val Val Thr Val Asn Pro
        115                 120                 125

<210> SEQ ID NO 54
<211> LENGTH: 118
<212> TYPE: PRT
<213> ORGANISM: Ginglymostoma cirratum
<220> FEATURE:
<223> OTHER INFORMATION: >gi| 21747977| gb| AAM76242.1+51
     antigen receptor [Ginglymostoma cirratum]

<400> SEQUENCE: 54

Val Leu Leu Ala Leu Leu Pro Tyr Val Phe Thr Ala Arg Val Asp Gln
1               5                   10                  15

-continued

Thr Pro Arg Ser Val Thr Lys Glu Thr Gly Glu Ser Leu Thr Ile Asn
            20                  25                  30

Cys Val Leu Arg Asp Ala Ser Tyr Ala Leu Gly Ser Thr Cys Trp Tyr
            35                  40                  45

Arg Lys Lys Ser Gly Ser Thr Asn Glu Glu Ser Ile Ser Lys Gly Gly
        50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Gly Thr Tyr Arg Cys Gly Val
                85                  90                  95

Ser Asn Trp Cys Gly Asp Tyr Cys Ala Leu Gly Thr Tyr Ala Ala Cys
            100                 105                 110

Gly Asp Gly Thr Ala Val
        115

<210> SEQ ID NO 55
<211> LENGTH: 123
<212> TYPE: PRT
<213> ORGANISM: Ginglymostoma cirratum
<220> FEATURE:
<223> OTHER INFORMATION: >gi| 21539983| gb| AAM52975.1+51
      antigen receptor [Ginglymostoma cirratum]

<400> SEQUENCE: 55

Val Leu Leu Ala Leu Leu Pro Tyr Val Phe Thr Ala Arg Val Asp Gln
1               5                   10                  15

Thr Pro Arg Ser Val Thr Lys Leu Thr Gly Glu Ser Leu Thr Ile Asn
            20                  25                  30

Cys Val Leu Arg Asp Ala Ser Tyr Ala Leu Gly Ser Thr Cys Trp Tyr
            35                  40                  45

Arg Lys Lys Ser Gly Ser Thr Asn Glu Glu Ser Ile Ser Lys Gly Gly
        50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Gly Thr Tyr Arg Cys Gly Thr
                85                  90                  95

Ala Gly Ala Val Thr Arg Asp Val Leu Phe Tyr Ala Ala Cys Gly Asp
            100                 105                 110

Gly Thr Ala Val Thr Val Asn Pro Gly Ile Pro
        115                 120

<210> SEQ ID NO 56
<211> LENGTH: 121
<212> TYPE: PRT
<213> ORGANISM: Ginglymostoma cirratum
<220> FEATURE:
<223> OTHER INFORMATION: >gi| 21885436| gb| AAM76960.1+51
      antigen receptor [Ginglymostoma cirratum]

<400> SEQUENCE: 56

Ser Val Leu Leu Ala Leu Leu Pro Asn Val Phe Thr Ala Arg Val Asp
1               5                   10                  15

Gln Thr Pro Arg Ser Val Thr Lys Glu Thr Gly Glu Ser Leu Thr Ile
            20                  25                  30

Asn Cys Val Leu Arg Asp Ala Ser Tyr Ala Leu Gly Ser Thr Cys Trp
            35                  40                  45

Tyr Arg Lys Lys Ser Gly Ser Thr Asn Glu Glu Ser Ile Ser Lys Gly
        50                  55                  60

```
Gly Arg Tyr Val Glu Thr Val Asn Ser Gly Ser Lys Ser Phe Ser Leu
 65                  70                  75                  80

Arg Ile Asn Asp Leu Thr Val Glu Asp Gly Thr Tyr Arg Cys Gly
                 85                  90                  95

Val Leu Val Arg Tyr Val Thr Arg Ala Leu Pro Tyr Ala Ala Cys Gly
                100                 105                 110

Asp Gly Thr Ala Val Thr Val Asn Pro
            115                 120

<210> SEQ ID NO 57
<211> LENGTH: 109
<212> TYPE: PRT
<213> ORGANISM: Ginglymostoma cirratum
<220> FEATURE:
<223> OTHER INFORMATION: >gi| 25987495| gb| AAN75874.1+51
      AF447118_1 novel antigen receptor [Ginglymostoma cirratum]

<400> SEQUENCE: 57

Ala Arg Val Asp Gln Thr Pro Arg Ser Val Thr Lys Glu Thr Gly Glu
  1               5                  10                  15

Ser Leu Thr Ile Asn Cys Val Leu Arg Asp Ala Ser Tyr Ala Leu Gly
                 20                  25                  30

Ser Thr Cys Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
         50                  55                  60

Ser Phe Ser Leu Arg Ile Asn Asp Leu Thr Val Glu Asp Gly Gly Thr
 65                  70                  75                  80

Tyr Arg Cys Gly Val Trp Gly Gln Leu His Val Arg Cys Ala Leu Gly
                 85                  90                  95

Asp Ala Ala Cys Gly Asp Gly Thr Ala Val Thr Val Asn
                100                 105

<210> SEQ ID NO 58
<211> LENGTH: 119
<212> TYPE: PRT
<213> ORGANISM: Ginglymostoma cirratum
<220> FEATURE:
<223> OTHER INFORMATION: >gi| 21885442| gb| AAM76962.1+51
      antigen receptor [Ginglymostoma cirratum]

<400> SEQUENCE: 58

Leu Leu Ala Leu Leu Pro Asn Val Phe Thr Ala Arg Val Asp Gln Thr
  1               5                  10                  15

Pro Arg Ser Val Thr Lys Glu Thr Gly Glu Ser Leu Thr Ile Asn Cys
                 20                  25                  30

Val Leu Arg Asp Ala Ser Tyr Ala Leu Gly Ser Thr Cys Trp Tyr Arg
             35                  40                  45

Lys Lys Ser Gly Ser Thr Asn Glu Glu Ser Ile Ser Lys Gly Gly Arg
         50                  55                  60

Tyr Val Glu Thr Val Asn Ser Gly Ser Lys Ser Phe Ser Leu Arg Ile
 65                  70                  75                  80

Asn Asp Leu Thr Val Glu Asp Gly Gly Thr Tyr Arg Cys Gly Val Leu
                 85                  90                  95

Val Arg Tyr Val Thr Arg Ala Leu Pro Tyr Ala Ala Cys Gly Asp Gly
                100                 105                 110

Thr Ala Val Thr Val Asn Pro
            115
```

<210> SEQ ID NO 59
<211> LENGTH: 120
<212> TYPE: PRT
<213> ORGANISM: Ginglymostoma cirratum
<220> FEATURE:
<223> OTHER INFORMATION: >gi| 21885444| gb| AAM76963.1+51
      antigen receptor [Ginglymostoma cirratum]

<400> SEQUENCE: 59

Val Leu Leu Ala Leu Leu Pro Asn Val Phe Thr Ala Arg Val Asp Gln
1               5                   10                  15

Thr Pro Arg Ser Val Thr Lys Glu Thr Gly Glu Ser Leu Thr Ile Asn
            20                  25                  30

Cys Val Leu Arg Asp Ala Ser Tyr Ala Leu Gly Ser Thr Cys Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Gly Thr Tyr Arg Cys Gly Val
                85                  90                  95

Leu Val Arg Tyr Val Thr Arg Ala Leu Pro Tyr Ala Ala Cys Gly Asp
            100                 105                 110

Gly Thr Ala Val Thr Val Asn Pro
        115                 120

<210> SEQ ID NO 60
<211> LENGTH: 124
<212> TYPE: PRT
<213> ORGANISM: Ginglymostoma cirratum
<220> FEATURE:
<223> OTHER INFORMATION: >gi| 21748009| gb| AAM76258.1+51
      antigen receptor [Ginglymostoma cirratum]

<400> SEQUENCE: 60

Val Leu Leu Ala Leu Leu Pro Tyr Val Phe Thr Ala Arg Val Asp Gln
1               5                   10                  15

Thr Pro Arg Ser Val Thr Lys Glu Thr Gly Glu Ser Leu Thr Ile Asn
            20                  25                  30

Cys Val Leu Arg Asp Ala Ser Tyr Ala Leu Gly Ser Thr Cys Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Gly Thr Tyr Arg Cys Gly Ile
                85                  90                  95

Ala Gly Val Gly Asp Ser Cys Asp Arg Ala Val Leu Cys Phe Tyr Ala
            100                 105                 110

Ala Cys Gly Asp Gly Thr Ala Val Thr Val Asn Pro
        115                 120

<210> SEQ ID NO 61
<211> LENGTH: 123
<212> TYPE: PRT
<213> ORGANISM: Ginglymostoma cirratum
<220> FEATURE:
<223> OTHER INFORMATION: >gi| 21539988| gb| AAM52977.1+51
      antigen receptor [Ginglymostoma cirratum]

<400> SEQUENCE: 61

Val Leu Leu Ala Leu Leu Pro Tyr Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Ser Asn Cys Ala Leu Ser Ser Thr Tyr Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Ser Gly Thr Tyr Arg Cys Asn Val
                85                  90                  95

Tyr His Tyr Ser Trp Tyr Gly Pro Ile Ala Ile Glu Leu Glu Asp Val
            100                 105                 110

Tyr Gly Gly Gly Thr Val Val Thr Val Asn Pro
        115                 120

<210> SEQ ID NO 62
<211> LENGTH: 119
<212> TYPE: PRT
<213> ORGANISM: Ginglymostoma cirratum
<220> FEATURE:
<223> OTHER INFORMATION: >gi| 21748029| gb| AAM76268.1+51
      antigen receptor [Ginglymostoma cirratum]

<400> SEQUENCE: 62

Val Leu Leu Ala Leu Leu Pro Tyr Val Phe Thr Val Arg Val Asp Gln
1               5                   10                  15

Thr Pro Arg Thr Val Thr Lys Glu Thr Gly Glu Ser Leu Thr Ile Asn
            20                  25                  30

Cys Val Leu Arg Asp Ala Asn Tyr Ala Leu Gly Ser Thr Cys Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Gly Thr Tyr Arg Cys Gly Arg
                85                  90                  95

Gly Tyr Gly Cys Ser Lys Leu Cys Ser Tyr Ala Ala Cys Gly Asp Gly
            100                 105                 110

Thr Ala Val Thr Val Asn Pro
        115

<210> SEQ ID NO 63
<211> LENGTH: 143
<212> TYPE: PRT
<213> ORGANISM: Ginglymostoma cirratum
<220> FEATURE:
<223> OTHER INFORMATION: >gi| 3986602| gb| AAC84095.1+51
      antigen receptor [Ginglymostoma cirratum]

<400> SEQUENCE: 63

Val Phe Thr Val Arg Val Asp Gln Thr Pro Gln Thr Ile Thr Lys Glu
1               5                   10                  15

Thr Gly Glu Ser Leu Thr Ile Asn Cys Val Leu Arg Asp Ser Asn Cys
            20                  25                  30

```
Gly Phe Ser Ser Thr Tyr Trp Tyr Arg Lys Lys Ser Ala Ser Thr Asn
             35                  40                  45

Glu Glu Ser Ile Ser Lys Gly Gly Arg Tyr Val Glu Thr Val Asn Ser
 50                  55                  60

Gly Ser Lys Ser Phe Ser Leu Arg Ile Asn Asp Leu Thr Val Glu Asp
 65                  70                  75                  80

Ser Gly Thr Tyr Arg Cys Lys Gly Leu Arg Leu Ala Ser Leu Ile Val
                 85                  90                  95

Gly Ser Trp Thr Ala Asn Trp Arg Gly Asp Leu Tyr Gly Gly Gly Thr
                100                 105                 110

Val Val Thr Val Asn Pro Gly Ile Pro Leu Ser Pro Pro Ile Val Ser
            115                 120                 125

Leu Leu His Ser Ala Thr Glu Glu Gln Arg Ala Asn Gly Phe Val
        130                 135                 140

<210> SEQ ID NO 64
<211> LENGTH: 145
<212> TYPE: PRT
<213> ORGANISM: Ginglymostoma cirratum
<220> FEATURE:
<223> OTHER INFORMATION: >gi| 699465| gb| AAB48206.1|
      novel antigen receptor, partial [Ginglymostoma cirratum]

<400> SEQUENCE: 64

Met Asn Ile Phe Leu Leu Ser Val Leu Leu Ala Leu Leu Pro Tyr Val
 1               5                  10                  15

Phe Thr Ala Arg Val Asp Gln Thr Pro Arg Ser Val Thr Lys Glu Thr
             20                  25                  30

Gly Glu Ser Leu Thr Ile Asn Cys Val Leu Arg Asp Ala Ser Tyr Ala
             35                  40                  45

Leu Gly Ser Thr Cys Trp Tyr Arg Lys Lys Pro Gly Ser Thr Asn Glu
 50                  55                  60

Glu Ser Ile Ser Lys Gly Gly Arg Tyr Val Glu Thr Val Asn Ser Gly
 65                  70                  75                  80

Ser Lys Ser Phe Ser Leu Arg Ile Asn Asp Leu Thr Leu Glu Asp Gly
                 85                  90                  95

Gly Thr Tyr Arg Cys Gly Val Tyr Ala Met Arg Phe Phe Gly Pro Thr
                100                 105                 110

Pro Cys Ser Cys Asp Gly Tyr Ala Ala Cys Gly Asp Gly Thr Ala Val
            115                 120                 125

Thr Val Asn Pro Gly Ile Pro Pro Ser Pro Pro Ile Val Ser Leu Leu
        130                 135                 140

His
145

<210> SEQ ID NO 65
<211> LENGTH: 122
<212> TYPE: PRT
<213> ORGANISM: Ginglymostoma cirratum
<220> FEATURE:
<223> OTHER INFORMATION: >gi| 21539974| gb| AAM52971.1+51
      antigen receptor [Ginglymostoma cirratum]

<400> SEQUENCE: 65

Val Leu Leu Ala Leu Leu Pro Tyr Val Phe Thr Ala Arg Val Asp Gln
 1               5                  10                  15

Ala Pro Gln Thr Ile Thr Lys Glu Thr Gly Glu Ser Leu Thr Ile Asn
             20                  25                  30
```

```
Cys Val Leu Arg Asp Ser Asn Cys Ala Leu Ser Ser Thr Tyr Trp Tyr
            35                  40                  45

Arg Lys Lys Ser Gly Ser Thr Asn Glu Glu Ser Ile Ser Lys Gly Gly
 50                  55                  60

Arg Tyr Val Glu Thr Val Asn Ser Gly Ser Lys Ser Phe Ser Leu Arg
 65                  70                  75                  80

Ile Asn Asp Leu Thr Val Glu Asp Ser Gly Thr Tyr Arg Cys Asn Val
                85                  90                  95

Tyr Gly Val Val Arg Trp Glu Leu Asn Trp Arg Cys Gly Asn Tyr Asp
            100                 105                 110

Val Tyr Gly Gly Gly Thr Val Val Thr Val
            115                 120

<210> SEQ ID NO 66
<211> LENGTH: 116
<212> TYPE: PRT
<213> ORGANISM: artificial sequence
<220> FEATURE:
<223> OTHER INFORMATION: >gi| 161172318| pdb| 2Z8W| C Chain C,
      Structure Of An Ignar-Ama1 Complex

<400> SEQUENCE: 66

Ala Trp Val Asp Gln Thr Pro Arg Thr Ala Thr Lys Glu Thr Gly Glu
 1               5                  10                  15

Ser Leu Thr Ile Asn Cys Val Leu Arg Asp Ala Ser Phe Glu Leu Lys
                20                  25                  30

Asp Thr Gly Trp Tyr Arg Thr Lys Leu Gly Ser Thr Asn Glu Gln Ser
            35                  40                  45

Ile Ser Ile Gly Gly Arg Tyr Val Glu Thr Val Asn Lys Gly Ser Lys
 50                  55                  60

Ser Phe Ser Leu Arg Ile Ser Asp Leu Arg Val Glu Asp Ser Gly Thr
 65                  70                  75                  80

Tyr Lys Cys Gln Ala Phe Tyr Ser Leu Leu Leu Arg Asp Tyr Asn Tyr
                85                  90                  95

Ser Leu Leu Phe Arg Gly Glu Lys Gly Ala Gly Thr Ala Leu Thr Val
            100                 105                 110

Lys Ala Ala Ala
            115

<210> SEQ ID NO 67
<211> LENGTH: 128
<212> TYPE: PRT
<213> ORGANISM: Ginglymostoma cirratum
<220> FEATURE:
<223> OTHER INFORMATION: >gi| 21747979| gb| AAM76243.1+51
      antigen receptor [Ginglymostoma cirratum]

<400> SEQUENCE: 67

Val Leu Leu Ala Leu Leu Pro Tyr Val Phe Thr Ala Arg Val Asp Gln
 1               5                  10                  15

Thr Pro Arg Ser Val Thr Lys Glu Thr Gly Glu Ser Leu Thr Ile Asn
                20                  25                  30

Cys Val Leu Arg Asp Ala Ser Tyr Ala Leu Gly Ser Thr Cys Trp Tyr
            35                  40                  45

Arg Lys Lys Ser Gly Ser Thr Asn Glu Glu Ser Ile Ser Lys Gly Gly
 50                  55                  60

Arg Tyr Val Glu Thr Val Asn Ser Gly Ser Lys Ser Phe Ser Leu Arg
 65                  70                  75                  80
```

```
Ile Asn Asp Leu Thr Val Glu Asp Ser Gly Thr Tyr Arg Cys Gly Val
                85                  90                  95

Asn Arg Val Ala Gly Val Thr Cys Ala Pro Gly Thr Leu Cys Ala Leu
            100                 105                 110

Ile Gly Tyr Ala Ala Cys Gly Asp Gly Thr Ala Val Thr Val Asn Pro
        115                 120                 125

<210> SEQ ID NO 68
<211> LENGTH: 123
<212> TYPE: PRT
<213> ORGANISM: Ginglymostoma cirratum
<220> FEATURE:
<223> OTHER INFORMATION: >gi| 21747983| gb| AAM76245.1+51  antigen
      receptor [Ginglymostoma cirratum]

<400> SEQUENCE: 68

Val Leu Leu Ala Leu Leu Pro Tyr Val Phe Thr Ala Arg Val Asp Gln
1               5                   10                  15

Thr Pro Arg Ser Val Thr Lys Glu Thr Gly Glu Ser Leu Thr Ile Asn
            20                  25                  30

Cys Val Leu Arg Asp Ala Asn Tyr Ala Leu Gly Ser Thr Cys Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Gly Thr Tyr Arg Cys Gly Val
                85                  90                  95

Ala Gly Val Asp Leu Cys Asp Tyr Ile Cys Ala Leu Glu Gly Ala Ala
            100                 105                 110

Cys Gly Asp Gly Thr Ala Val Thr Val Asn Pro
        115                 120

<210> SEQ ID NO 69
<211> LENGTH: 114
<212> TYPE: PRT
<213> ORGANISM: Ginglymostoma cirratum
<220> FEATURE:
<223> OTHER INFORMATION: >gi| 21898862| gb| AAM77152.1+51  antigen
      receptor [Ginglymostoma cirratum]

<400> SEQUENCE: 69

Val Leu Leu Ala Leu Leu Pro Asn Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Ser Asn Cys Ala Leu Ser Ser Thr Tyr Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Ser Gly Thr Tyr Arg Cys Lys Val
                85                  90                  95

Ile Ala Gly Arg Arg Tyr Asp Cys Arg Val Thr His Asp Val Tyr Gly
            100                 105                 110

Gly Gly
```

```
<210> SEQ ID NO 70
<211> LENGTH: 114
<212> TYPE: PRT
<213> ORGANISM: Ginglymostoma cirratum
<220> FEATURE:
<223> OTHER INFORMATION: >gi| 25987501| gb| AAN75877.1+51
      AF447121_1 novel antigen receptor [Ginglymostoma cirratum]

<400> SEQUENCE: 70

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Ser Val Tyr Ser Trp Cys Pro Thr Val Thr Gly
                85                  90                  95

Met Val Cys Ser Pro Tyr Ala Ala Cys Gly Gly Gly Val Val Val Thr
            100                 105                 110

Val Asn

<210> SEQ ID NO 71
<211> LENGTH: 113
<212> TYPE: PRT
<213> ORGANISM: Orectolobus maculatus
<220> FEATURE:
<223> OTHER INFORMATION: >gi| 52696109| pdb| 1VES| A Chain A,
      Structure Of New Antigen Receptor Variable Domain From Sharks
      variable domain [Orectolobus maculatus]

<400> SEQUENCE: 71

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Ser Leu Pro Leu Gly Asp Tyr Asn Tyr
                85                  90                  95

Ser Leu Leu Phe Arg Gly Glu Lys Gly Ala Gly Thr Ala Leu Thr Val
            100                 105                 110

Lys

<210> SEQ ID NO 72
<211> LENGTH: 108
<212> TYPE: PRT
<213> ORGANISM: Ginglymostoma cirratum
<220> FEATURE:
<223> OTHER INFORMATION: >gi| 21898858| gb| AAM77150.1+51  antigen
      receptor [Ginglymostoma cirratum]

<400> SEQUENCE: 72
```

Val Leu Leu Ala Leu Leu Pro Tyr Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Ser Asn Cys Ala Leu Ser Ser Thr Tyr Trp Tyr
            35                  40                  45

Arg Lys Lys Ser Gly Ser Thr Asn Glu Glu Ser Ile Ser Lys Gly Gly
50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Ser Gly Thr Tyr Arg Cys Lys Val
            85                  90                  95

Leu Ala Gly Met Glu Glu Asp Phe Ile Arg Arg Trp
            100                 105

<210> SEQ ID NO 73
<211> LENGTH: 100
<212> TYPE: PRT
<213> ORGANISM: Ginglymostoma cirratum
<220> FEATURE:
<223> OTHER INFORMATION: >gi| 3986668| gb| AAC84128.1+51 antigen
      receptor [Ginglymostoma cirratum]

<400> SEQUENCE: 73

Arg Val Asp Gln Thr Pro Gln Thr Ile Thr Lys Glu Thr Gly Glu Ser
1               5                   10                  15

Leu Thr Met Asn Cys Val Leu Arg Asp Thr Asn Cys Ala Leu Ser Ser
            20                  25                  30

Thr Tyr Trp Tyr Arg Lys Lys Ser Gly Ser Thr Asn Glu Glu Ser Ile
            35                  40                  45

Ser Lys Gly Gly Arg Tyr Val Glu Thr Val Asn Ser Gly Ser Lys Ser
50                  55                  60

Phe Ser Leu Arg Ile Asn Asp Leu Thr Val Glu Asp Ser Gly Thr Tyr
65                  70                  75                  80

Arg Cys Lys Ala Ser Ala Gly Leu Asp Cys Arg Leu Tyr Tyr Asn Val
            85                  90                  95

Tyr Gly Gly Gly
            100

<210> SEQ ID NO 74
<211> LENGTH: 121
<212> TYPE: PRT
<213> ORGANISM: Ginglymostoma cirratum
<220> FEATURE:
<223> OTHER INFORMATION: >gi| 21747989| gb| AAM76248.1+51 antigen
      receptor [Ginglymostoma cirratum]

<400> SEQUENCE: 74

Val Leu Leu Ala Leu Leu Pro Tyr Val Phe Thr Ala Arg Val Asp Gln
1               5                   10                  15

Thr Pro Arg Ser Val Thr Lys Glu Thr Gly Glu Ser Leu Thr Ile Asn
            20                  25                  30

Cys Val Leu Arg Asp Ala Ser Tyr Ala Leu Gly Ser Thr Cys Trp Tyr
            35                  40                  45

Arg Lys Lys Ser Gly Ser Thr Asn Glu Glu Ser Ile Ser Lys Gly Gly
50                  55                  60

Arg Tyr Val Glu Thr Val Asn Ser Gly Ser Lys Ser Phe Ser Leu Arg
65                  70                  75                  80

```
Ile Asn Asp Leu Thr Val Glu Asp Gly Gly Thr Tyr Arg Cys Ala Ile
                85                  90                  95

Trp Cys Gly Ala Val Thr Thr Gly Cys Ala Leu Arg Ala Ala Cys Gly
            100                 105                 110

Asp Gly Thr Ala Val Thr Val Asn Pro
        115                 120

<210> SEQ ID NO 75
<211> LENGTH: 120
<212> TYPE: PRT
<213> ORGANISM: Ginglymostoma cirratum
<220> FEATURE:
<223> OTHER INFORMATION: >gi| 21747970| gb| AAM76239.1+51  antigen
      receptor [Ginglymostoma cirratum]

<400> SEQUENCE: 75

Val Leu Leu Ala Leu Leu Pro Tyr Val Phe Thr Ala Arg Val Asp Gln
1               5                   10                  15

Thr Pro Arg Ser Val Thr Lys Glu Thr Gly Glu Ser Leu Thr Ile Asn
            20                  25                  30

Cys Val Leu Arg Asp Ala Ser Tyr Ala Leu Gly Ser Thr Cys Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Gly Thr Tyr Arg Cys Gly Ala
                85                  90                  95

Pro Val Tyr Ser Cys Arg Thr Cys Ala Leu Asp Ala Ala Cys Gly Asp
            100                 105                 110

Gly Thr Ala Val Thr Val Asn Pro
        115                 120

<210> SEQ ID NO 76
<211> LENGTH: 135
<212> TYPE: PRT
<213> ORGANISM: Ginglymostoma cirratum
<220> FEATURE:
<223> OTHER INFORMATION: >gi| 3982935| gb| AAC83718.1+51  antigen
      receptor [Ginglymostoma cirratum]

<400> SEQUENCE: 76

Arg Val Asp Gln Thr Pro Arg Ser Val Thr Lys Glu Thr Gly Glu Ser
1               5                   10                  15

Leu Thr Ile Asn Cys Val Leu Arg Asp Ala Ser Tyr Ala Leu Gly Ser
            20                  25                  30

Thr Cys Trp Tyr Arg Lys Lys Ser Gly Ser Thr Asn Glu Glu Asn Ile
        35                  40                  45

Ser Lys Gly Gly Arg Tyr Val Glu Thr Val Asn Ser Gly Ser Lys Ser
    50                  55                  60

Phe Ser Leu Arg Asn Asn Asp Leu Thr Val Glu Asp Gly Gly Thr Tyr
65                  70                  75                  80

Arg Cys Gly Glu Arg Leu Val Gly Thr Arg Asp Arg Phe Tyr Ala Ala
                85                  90                  95

Cys Gly Asp Gly Thr Ala Val Thr Val Asn Pro Gly Ile Pro Leu Ser
            100                 105                 110

Pro Pro Ile Val Ser Leu Leu His Ser Ala Thr Glu Glu Gln Arg Ala
        115                 120                 125
```

Asn Arg Phe Val Gln Leu Val
    130             135

<210> SEQ ID NO 77
<211> LENGTH: 121
<212> TYPE: PRT
<213> ORGANISM: artificial sequence
<220> FEATURE:
<223> OTHER INFORMATION: >gi| 134104489| pdb| 2I26| Crystal
      Structure Analysis Of The Nurse Shark New Antigen Receptor
      Ancestral Variable Domain In Complex With Lysozyme

<400> SEQUENCE: 77

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Pro Glu Ser Arg Tyr Gly Ser Tyr Asp Ala Glu Cys
                85                  90                  95

Ala Ala Leu Asn Asp Gln Tyr Gly Gly Gly Thr Val Val Thr Val Asn
            100                 105                 110

Ala Ala Ala His His His His His
        115                 120

<210> SEQ ID NO 78
<211> LENGTH: 135
<212> TYPE: PRT
<213> ORGANISM: Ginglymostoma cirratum
<220> FEATURE:
<223> OTHER INFORMATION: >gi| 3982937| gb| AAC83719.1+51 antigen
      receptor [Ginglymostoma cirratum]

<400> SEQUENCE: 78

Val Asp Gln Thr Pro Gln Thr Ile Thr Lys Glu Thr Gly Glu Ser Leu
1               5                   10                  15

Thr Ile Asn Cys Val Leu Arg Asp Ser Asn Cys Ala Leu Ser Ser Thr
            20                  25                  30

Tyr Trp Tyr Arg Lys Lys Ser Gly Ser Thr Asn Glu Glu Ser Ile Ser
        35                  40                  45

Lys Gly Gly Arg Tyr Val Glu Thr Val Asn Ser Gly Ser Lys Ser Phe
    50                  55                  60

Ser Leu Arg Ile Asn Asp Leu Thr Val Glu Asp Ser Gly Thr Tyr Arg
65                  70                  75                  80

Cys Lys Val Ser Gln Ala Gly His Gly Leu Trp Cys Arg Leu Glu Pro
                85                  90                  95

Pro Asp Val Tyr Gly Gly Thr Val Val Thr Val Asn Pro Gly Ile
            100                 105                 110

Pro Leu Ser Pro Pro Ile Val Ser Leu Leu His Ser Ala Thr Glu Glu
        115                 120                 125

Gln Arg Ala Asn Gly Phe Val
    130             135

<210> SEQ ID NO 79

```
<211> LENGTH: 137
<212> TYPE: PRT
<213> ORGANISM: Ginglymostoma cirratum
<220> FEATURE:
<223> OTHER INFORMATION: >gi| 3982933| gb| AAC83717.1+51  antigen
      receptor [Ginglymostoma cirratum]

<400> SEQUENCE: 79

Arg Val Asp Gln Thr Pro Arg Thr Ile Thr Lys Glu Thr Gly Glu Ser
1               5                   10                  15

Leu Thr Ile Asn Cys Val Leu Arg Asp Ala Asn Tyr Ala Leu Gly Ser
            20                  25                  30

Thr Cys Trp Tyr Arg Lys Lys Ser Gly Ser Thr Asn Glu Glu Ser Ile
        35                  40                  45

Ser Lys Gly Gly Arg Tyr Val Glu Thr Val Asn Ser Gly Ser Lys Ser
    50                  55                  60

Phe Ser Leu Arg Val Asn Asp Leu Thr Val Glu Asp Gly Gly Thr Tyr
65                  70                  75                  80

Arg Cys Val Ser Ala Gly Gly Leu Ser Arg Leu Trp Gly Asn Tyr Ala
                85                  90                  95

Ala Cys Gly Asp Gly Thr Ala Val Thr Val Asn Pro Gly Ile Pro Pro
            100                 105                 110

Ser Pro Pro Ile Val Ser Leu Leu His Ser Ala Thr Glu Glu Gln Arg
        115                 120                 125

Ala Asn Arg Phe Val Gln Leu Val Cys
    130                 135

<210> SEQ ID NO 80
<211> LENGTH: 144
<212> TYPE: PRT
<213> ORGANISM: Ginglymostoma cirratum
<220> FEATURE:
<223> OTHER INFORMATION: >gi| 3982955| gb| AAC83728.1+51  antigen
      receptor [Ginglymostoma cirratum]

<400> SEQUENCE: 80

Ala Arg Val Asp Gln Thr Pro Gln Thr Ile Thr Lys Glu Thr Gly Glu
1               5                   10                  15

Ser Leu Thr Met Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Leu Val Cys Lys Cys Thr Gly Glu Arg Gly Asn Tyr
                85                  90                  95

Asp Val Tyr Gly Gly Gly Thr Val Thr Val Asn Pro Gly Ile Pro
            100                 105                 110

Leu Ser Pro Pro Ile Val Ser Leu Leu His Ser Ala Thr Glu Glu Gln
        115                 120                 125

Arg Ala Asn Gly Phe Val Gln Leu Val Cys Leu Ile Ser Gly Tyr Tyr
    130                 135                 140

<210> SEQ ID NO 81
<211> LENGTH: 673
<212> TYPE: PRT
<213> ORGANISM: Triakis scyllium
```

```
<220> FEATURE:
<223> OTHER INFORMATION: >gi| 307685091| dbj| BAJ20187.1+51
      immunoglobulin NAR [Triakis scyllium]

<400> SEQUENCE: 81

Met His Ile Phe Trp Ala Ala Leu Leu Leu Thr Trp Leu Ser Asn Ala
1               5                   10                  15

Phe Ser Ala His Val Asp Gln Thr Pro Arg Val Ala Thr Lys Glu Thr
            20                  25                  30

Gly Glu Ser Leu Thr Ile Asn Cys Val Leu Arg Gly Ser Cys Leu
            35                  40                  45

Leu Asp Ala Thr Ser Trp Phe Arg Gln Asn Pro Gly Ser Thr Gly Trp
50                      55                  60

Glu Arg Ile Thr Ile Gly Gly Arg Tyr Val Asp Ser Val Asn Lys Gly
65                  70                  75                  80

Ser Lys Ser Phe Ser Leu Gln Ile Lys Asp Leu Thr Val Val Asp Ser
                85                  90                  95

Val Thr Phe Tyr Cys Thr Ala Gln Tyr Tyr Val Gly His Gly Cys Tyr
            100                 105                 110

Gly Leu Ala Val Glu Asp Gly Ala Gly Thr Val Leu Thr Val Asn Pro
            115                 120                 125

Gly Pro Thr Pro Pro Ile Ile Asn Leu Phe Ser Glu Thr Asp Glu Leu
            130                 135                 140

Arg Ala Lys Gly Phe Val Gln Leu Ile Cys Leu Ile Ser Glu Tyr Lys
145                 150                 155                 160

Pro Glu Ser Ile Arg Val Ser Trp Glu Lys Asn Gly Asn Ala Arg Gln
                165                 170                 175

Ser Gly Phe Thr Thr Thr Ser Pro Cys Lys Thr Ala Lys Gly Glu Phe
            180                 185                 190

Gln Ser Arg Ser Ile Leu Thr Leu Pro Leu Gln Glu Trp Asn Ser Gly
            195                 200                 205

Ser Thr Tyr Ser Cys Gln Val Thr His Ser Ala Thr Asn Ser Asn Lys
            210                 215                 220

Arg Lys Glu Ile Arg Ser Thr Ser Glu Ile Thr Val Phe Leu Arg Asp
225                 230                 235                 240

Pro Ser Leu Glu Glu Ile Trp Ile Arg Lys Thr Val Thr Leu Ile Cys
                245                 250                 255

Glu Val Val Ser Thr Val Pro Ser Val Val Gly Ile Ser Trp Thr Val
            260                 265                 270

Asp Gly Lys Lys Arg Thr Glu Gly Val Gln Ile Glu Gly Arg Gln Gln
            275                 280                 285

Gly Gln Asn Gln Tyr Leu Thr Ile Ser Arg Leu Thr Ser Ser Val Glu
            290                 295                 300

Glu Trp Asp Arg Gly Ala Glu Tyr Asn Cys Ser Ala Gln Gln Ser Glu
305                 310                 315                 320

Ser Ser Thr Pro Val Ser Lys His Thr Gln Lys Leu Lys Val Lys Pro
                325                 330                 335

Ser Lys Pro Asn Leu Arg Leu Leu Pro Pro Ser Ala Glu Glu Leu Gln
            340                 345                 350

Ser Ser Ser Val Ala Thr Leu Thr Cys Leu Ile Arg Gly Phe Tyr Pro
            355                 360                 365

Asp Lys Ile Ser Ile Ser Trp Glu Lys Asp Gly Ala Val Leu Ser Ser
            370                 375                 380

Asn Ile Thr Arg Phe Pro Thr Ala Leu Glu Gln Asp Gln Thr Phe Ser
```

```
            385                 390                 395                 400
    Thr Ser Ser Leu Leu Ile Leu Pro Ala Gly Glu Trp Lys Thr Gly Ala
                    405                 410                 415

Arg Tyr Thr Cys Thr Ala Ser His Pro Ala Ser Lys Phe Thr Gly Lys
                    420                 425                 430

Arg Thr Ile Asn Ser Pro Lys Ala Asp Cys Tyr Glu Glu Asp Ile Ser
                    435                 440                 445

Val Asn Ile Leu Asn Pro Ser Phe Glu Glu Ile Trp Val Gln Lys Thr
    450                 455                 460

Ala Thr Ile Val Cys Glu Ile Arg Tyr Thr Val Leu Glu Asn Val Ser
    465                 470                 475                 480

Val Ser Trp Gln Val Asp Gly Arg Met Arg Thr Gly Val Glu Thr
                    485                 490                 495

Gln Thr Pro Glu Trp Ser Gly Ser Lys Thr Thr Ile Met Ser Lys Leu
                    500                 505                 510

Lys Val Thr Ala Ala Glu Trp Asp Thr Gly Val Glu Tyr Val Cys Leu
                    515                 520                 525

Ala Glu Gly Ser Glu Leu Pro Thr Pro Lys Lys Arg Ser Thr Arg Lys
                    530                 535                 540

Ile Lys Val Gly Ala Met Asn Ser Pro Lys Val Tyr Ile Leu Pro Pro
    545                 550                 555                 560

Ser Val Ala Glu Ile Asp Ser Glu Lys Thr Ala Thr Leu Met Cys Leu
                    565                 570                 575

Ala Thr Gly Phe Tyr Pro Ala Glu Ile Tyr Ile Ala Trp Leu Ala Asn
                    580                 585                 590

Asp Thr Leu Leu Asp Ser Asp Phe Pro Asn Gln Pro Val Ser Glu Lys
                    595                 600                 605

Gly Asn Gly Ser Ser Phe Ile Ala Ser Arg Leu Arg Leu Thr Ala Ala
                    610                 615                 620

Glu Trp Asn Thr Gly Thr Thr Tyr Ser Cys Leu Val Gly His Pro Ser
    625                 630                 635                 640

Leu Glu Arg Asn Leu Ile Arg Ser Ile Asn Lys Ser Tyr Gly Lys Pro
                    645                 650                 655

Thr Leu Val Asn Val Ser Leu Ala Leu Ala Asp Ser Phe Thr Ser Cys
                    660                 665                 670

Ala

<210> SEQ ID NO 82
<211> LENGTH: 140
<212> TYPE: PRT
<213> ORGANISM: Ginglymostoma cirratum
<220> FEATURE:
<223> OTHER INFORMATION: >gi| 3982959| gb| AAC83730.1+51 antigen
      receptor [Ginglymostoma cirratum]

<400> SEQUENCE: 82

Arg Val Asp Gln Thr Pro Arg Ser Val Thr Lys Glu Thr Gly Glu Ser
    1               5                   10                  15

Leu Thr Ile Asn Cys Val Leu Arg Asp Ala Ser His Ala Leu Gly Ser
                    20                  25                  30

Thr Cys Trp Tyr Arg Lys Lys Ser Gly Ser Thr Asn Glu Glu Ser Ile
                    35                  40                  45

Ser Thr Gly Gly Arg Tyr Val Glu Ser Val Asn Ser Gly Ser Lys Ser
                    50                  55                  60

Phe Ser Leu Arg Ile Asn Asp Leu Thr Val Glu Asp Gly Gly Thr Tyr
```

```
                65                  70                  75                  80
Arg Cys Gly Val Cys Leu Ala Gly Gly Asn Arg Asp Tyr Cys Cys Leu
                            85                  90                  95

Leu Ala Asn Val Ala Ser Gly Asp Gly Thr Ala Val Thr Val Thr Ser
                100                 105                 110

Gly Ile Pro Pro Ser Pro Pro Ile Val Ser Leu Leu His Ser Ala Thr
            115                 120                 125

Glu Glu Gln Arg Ala Asn Arg Phe Val Gln Leu Val
            130                 135                 140

<210> SEQ ID NO 83
<211> LENGTH: 145
<212> TYPE: PRT
<213> ORGANISM: Ginglymostoma cirratum
<220> FEATURE:
<223> OTHER INFORMATION: >gi| 3986596| gb| AAC84092.1+51  antigen
      receptor [Ginglymostoma cirratum]

<400> SEQUENCE: 83

Asp Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Leu Gly Ile Thr Leu Val Ala Gly Val Glu Trp
                85                  90                  95

Gly Thr Asn Ser Cys Ala Leu Pro Gly Ser Tyr Ala Ala Cys Gly Asp
            100                 105                 110

Gly Thr Ala Val Thr Val Asn Pro Gly Ile Pro Pro Ser Pro Pro Ile
        115                 120                 125

Val Ser Leu Leu His Ser Ala Thr Glu Glu Gln Arg Ala Asn Gly Phe
    130                 135                 140

Val
145

<210> SEQ ID NO 84
<211> LENGTH: 113
<212> TYPE: PRT
<213> ORGANISM: Ginglymostoma cirratum
<220> FEATURE:
<223> OTHER INFORMATION: >gi| 25987449| gb| AAN75851.1+51
      AF447095_1 novel antigen receptor [Ginglymostoma cirratum]

<400> SEQUENCE: 84

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
```

```
                65                  70                  75                  80
Tyr Arg Cys Gly Leu Gly Val Ala Gly Gly Tyr Cys Asp Tyr Ala Leu
                    85                  90                  95
Cys Ser Ser Arg Tyr Ala Glu Cys Gly Asp Gly Thr Ala Val Thr Val
                100                 105                 110
Asn

<210> SEQ ID NO 85
<211> LENGTH: 118
<212> TYPE: PRT
<213> ORGANISM: Ginglymostoma cirratum
<220> FEATURE:
<223> OTHER INFORMATION: >gi| 21748017| gb| AAM76262.1+51  antigen
      receptor [Ginglymostoma cirratum]

<400> SEQUENCE: 85

Val Leu Leu Ala Leu Leu Pro Tyr Val Leu Thr Val Arg Val Asp Gln
1               5                   10                  15
Thr Pro Arg Ser Val Thr Lys Glu Thr Gly Glu Ser Leu Thr Ile Asn
                20                  25                  30
Cys Val Leu Arg Asp Ala Asn Tyr Ala Leu Gly Ser Thr Cys Trp Tyr
                35                  40                  45
Arg Lys Lys Ser Gly Ser Thr Asn Glu Glu Ser Ile Ser Lys Gly Gly
            50                  55                  60
Arg Tyr Val Glu Thr Val Asn Ser Gly Ser Lys Ser Phe Ser Leu Arg
65                  70                  75                  80
Ile Asn Asp Leu Thr Val Glu Asp Gly Gly Thr Tyr Arg Cys Gly Arg
                85                  90                  95
Gly Tyr Gly Cys Ser Lys Leu Cys Ser Tyr Ala Ala Cys Gly Asp Gly
                100                 105                 110
Thr Ala Val Thr Val Asn
            115

<210> SEQ ID NO 86
<211> LENGTH: 120
<212> TYPE: PRT
<213> ORGANISM: Ginglymostoma cirratum
<220> FEATURE:
<223> OTHER INFORMATION: >gi| 21885448| gb| AAM76965.1+51  antigen
      receptor [Ginglymostoma cirratum]

<400> SEQUENCE: 86

Val Leu Leu Ala Leu Leu Pro Asn Val Phe Pro Ala Arg Val Asp Gln
1               5                   10                  15
Thr Pro Lys Thr Ile Thr Lys Glu Thr Gly Glu Ser Leu Thr Ile Asn
                20                  25                  30
Cys Val Leu Ser Asp Thr Ser Cys Ala Trp Asp Ser Thr Tyr Trp Tyr
                35                  40                  45
Arg Lys Lys Leu Asp Ser Thr Asn Glu Glu Ser Thr Ser Lys Gly Gly
            50                  55                  60
Arg Tyr Val Glu Thr Val Asn Ser Glu Ser Thr Ser Phe Ser Leu Arg
65                  70                  75                  80
Ile Asn Asp Leu Thr Val Glu Asp Ser Gly Thr Tyr Arg Cys Arg Ala
                85                  90                  95
Glu Leu Tyr Cys Gly Ser Glu Leu Tyr Ser Phe Asp Glu Tyr Gly Gly
                100                 105                 110
Gly Thr Ile Val Thr Val Asn Pro
            115                 120
```

<210> SEQ ID NO 87
<211> LENGTH: 114
<212> TYPE: PRT
<213> ORGANISM: Ginglymostoma cirratum
<220> FEATURE:
<223> OTHER INFORMATION: >gi| 25987493| gb| AAN75873.1+51
    AF447117_1 novel antigen receptor [Ginglymostoma cirratum]

<400> SEQUENCE: 87

```
Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Ser Leu Gly Ala Arg Tyr Ser Cys Asp Tyr Asn
                85                  90                  95

Pro Cys Ser Ser Gly Tyr Ala Ala Cys Gly Gly Thr Val Val Thr
            100                 105                 110

Val Asn
```

<210> SEQ ID NO 88
<211> LENGTH: 126
<212> TYPE: PRT
<213> ORGANISM: Ginglymostoma cirratum
<220> FEATURE:
<223> OTHER INFORMATION: >gi| 21885434| gb| AAM76959.1+51  antigen
    receptor [Ginglymostoma cirratum]

<400> SEQUENCE: 88

```
Val Leu Leu Ala Leu Leu Pro Tyr Val Phe Thr Ala Arg Val Asp Gln
1               5                   10                  15

Thr Pro Arg Ser Val Thr Lys Glu Thr Gly Glu Ser Leu Thr Ile Asn
            20                  25                  30

Cys Val Leu Arg Asp Ala Ser Tyr Ala Leu Gly Ser Thr Cys Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Gly Thr Tyr Arg Cys Gly Gly
                85                  90                  95

Val Pro Ser Trp Ser Gly Val Thr Thr Pro Val Cys Ser Cys Gly Ile
            100                 105                 110

Tyr Ala Ala Cys Gly Asp Gly Thr Ala Val Thr Val Asn Pro
        115                 120                 125
```

<210> SEQ ID NO 89
<211> LENGTH: 120
<212> TYPE: PRT
<213> ORGANISM: Ginglymostoma cirratum
<220> FEATURE:
<223> OTHER INFORMATION: >gi| 21885378| gb| AAM76934.1+51  antigen
    receptor [Ginglymostoma cirratum]

<400> SEQUENCE: 89

Val Leu Leu Ala Leu Leu Pro Asn Val Phe Thr Ala Arg Val Asp Gln
1               5                   10                  15

Thr Pro Arg Ser Val Ile Lys Glu Thr Gly Glu Ser Leu Thr Ile Asn
            20                  25                  30

Cys Val Leu Arg Asp Ala Ser Tyr Ala Leu Gly Ser Thr Cys Trp Tyr
        35                  40                  45

Arg Lys Lys Ser Gly Ser Thr Asn Glu Glu Ser Ile Ser Lys Gly Gly
50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Gly Thr Tyr Arg Cys Gly Val
                85                  90                  95

Leu Val Arg Tyr Val Thr Arg Ala Leu Pro Tyr Ala Ala Cys Gly Asp
            100                 105                 110

Gly Thr Ala Val Thr Val Asn Pro
            115                 120

<210> SEQ ID NO 90
<211> LENGTH: 156
<212> TYPE: PRT
<213> ORGANISM: Ginglymostoma cirratum
<220> FEATURE:
<223> OTHER INFORMATION: >gi| 3983005| gb| AAC83753.1+51  antigen
    receptor [Ginglymostoma cirratum]

<400> SEQUENCE: 90

Leu Ala Leu Leu Pro Tyr Val Phe Thr Ala Arg Val Asp Gln Thr Pro
1               5                   10                  15

Gln Thr Ile Thr Lys Glu Thr Gly Glu Ser Leu Thr Ile Asn Cys Val
            20                  25                  30

Leu Arg Asp Ser Asn Cys Ala Leu Ser Ser Thr Tyr Trp Tyr Arg Lys
        35                  40                  45

Lys Ser Gly Ser Thr Asn Glu Glu Gly Ile Ser Lys Gly Gly Arg Tyr
50                  55                  60

Val Glu Thr Val Asn Gly Gly Ser Lys Ser Phe Ser Leu Arg Ile Asn
65                  70                  75                  80

Asp Leu Thr Val Glu Asp Ser Gly Thr Tyr Arg Cys Lys Ser His Ile
                85                  90                  95

Ala Gly Ser Thr Leu Glu Leu Thr Gly Leu Gly Tyr Asp Val Tyr Gly
            100                 105                 110

Gly Gly Thr Val Gly Thr Val Asn Pro Gly Ile Pro Leu Ser Pro Pro
        115                 120                 125

Ile Val Ser Leu Leu His Ser Ala Thr Glu Glu Gln Arg Ala Asn Gly
    130                 135                 140

Phe Val Gln Leu Val Cys Leu Ile Ser Gly Tyr Tyr
145                 150                 155

<210> SEQ ID NO 91
<211> LENGTH: 90
<212> TYPE: PRT
<213> ORGANISM: Ginglymostoma cirratum
<220> FEATURE:
<223> OTHER INFORMATION: >gi| 3982975| gb| AAC83738.1+51  antigen
    receptor [Ginglymostoma cirratum]

<400> SEQUENCE: 91

Gln Thr Ile Thr Lys Glu Thr Gly Glu Ser Leu Thr Ile Asn Cys Val

```
                1               5                   10                  15
Leu Arg Asp Ala Thr Tyr Ala Leu Gly Ser Thr Cys Trp Tyr Arg Lys
            20                  25                  30

Lys Ser Gly Ser Thr Asn Glu Glu Ser Ile Ser Lys Gly Gly Arg Tyr
            35                  40                  45

Val Glu Thr Val Asn Ser Gly Ser Lys Ser Phe Ser Met Arg Ile Asn
            50                  55                  60

Asp Leu Thr Val Glu Asp Ser Gly Thr Tyr Arg Cys Arg Ala Ser Gly
65                  70                  75                  80

Thr Leu Leu Trp Ile Gly Gly Gly Gly
                            85                  90

<210> SEQ ID NO 92
<211> LENGTH: 119
<212> TYPE: PRT
<213> ORGANISM: Ginglymostoma cirratum
<220> FEATURE:
<223> OTHER INFORMATION: >gi| 21885440| gb| AAM76961.1+51  antigen
      receptor [Ginglymostoma cirratum]

<400> SEQUENCE: 92

Val Leu Ala Leu Leu Pro Asn Val Phe Thr Ala Arg Val Asp Gln Thr
1               5                   10                  15

Pro Arg Ser Val Thr Lys Glu Thr Gly Glu Ser Leu Thr Ile Asn Cys
            20                  25                  30

Val Leu Arg Asp Ala Ser Tyr Ala Leu Gly Ser Thr Cys Trp Tyr Arg
            35                  40                  45

Lys Lys Ser Gly Ser Thr Asn Glu Glu Ser Ile Ser Lys Gly Gly Arg
            50                  55                  60

Tyr Val Glu Thr Val Asn Ser Gly Ser Lys Ser Phe Ser Leu Arg Ile
65                  70                  75                  80

Asn Asp Leu Thr Val Glu Asp Gly Gly Thr Tyr Arg Cys Gly Val Leu
                    85                  90                  95

Val Arg Tyr Val Thr Arg Ala Leu Pro Tyr Ala Ala Cys Gly Asp Gly
                100                 105                 110

Thr Ala Val Thr Val Asn Pro
            115

<210> SEQ ID NO 93
<211> LENGTH: 142
<212> TYPE: PRT
<213> ORGANISM: Ginglymostoma cirratum
<220> FEATURE:
<223> OTHER INFORMATION: >gi| 3986588| gb| AAC84088.1+51  antigen
      receptor [Ginglymostoma cirratum]

<400> SEQUENCE: 93

Asp Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
            50                  55                  60

Ser Phe Ser Leu Arg Ile Asn Asp Leu Thr Val Glu Asp Gly Gly Thr
65                  70                  75                  80

Tyr Arg Cys Gly Ala Pro Gly Gly Pro Ser Cys Asp Tyr Gly Pro Cys
```

```
                    85                  90                  95
Ala Leu Gly Asp Tyr Ala Ala Cys Gly Asp Gly Thr Ala Val Thr Val
                100                 105                 110

Asn Pro Gly Ile Pro Pro Ser Pro Pro Ile Val Ser Leu Leu His Ser
        115                 120                 125

Ala Thr Glu Glu Gln Arg Ala Asn Arg Phe Val Gln Leu Val
        130                 135                 140
```

<210> SEQ ID NO 94
<211> LENGTH: 117
<212> TYPE: PRT
<213> ORGANISM: Ginglymostoma cirratum
<220> FEATURE:
<223> OTHER INFORMATION: >gi| 21885395| gb| AAM76942.1+51  antigen receptor [Ginglymostoma cirratum]

<400> SEQUENCE: 94

```
Val Leu Leu Ala Leu Leu Pro Tyr Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Ala Ser Tyr Ala Leu Gly Ser Thr Cys Trp Tyr
        35                  40                  45

Arg Lys Lys Ser Gly Ser Thr Asn Glu Glu Ser Ile Ser Lys Gly Gly
50                  55                  60

Arg Tyr Val Glu Thr Val Asn Ser Gly Ser Lys Ser Phe Ser Met Arg
65                  70                  75                  80

Ile Asn Asp Leu Thr Val Glu Asp Ser Gly Thr Phe Arg Cys Gly Val
                85                  90                  95

Ser Trp Cys Gly Ser Gly Cys Asp Tyr Val Leu Ser Thr Leu Leu Pro
                100                 105                 110

Ala Glu Val Ala Leu
        115
```

<210> SEQ ID NO 95
<211> LENGTH: 118
<212> TYPE: PRT
<213> ORGANISM: Ginglymostoma cirratum
<220> FEATURE:
<223> OTHER INFORMATION: >gi| 21539954| gb| AAM52962.1+51  antigen receptor [Ginglymostoma cirratum]

<400> SEQUENCE: 95

```
Val Leu Leu Ala Leu Leu Pro Tyr Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Ser Asn Cys Ala Leu Ser Ser Thr Tyr Trp Tyr
        35                  40                  45

Arg Lys Lys Ser Gly Ser Thr Asn Glu Glu Ser Ile Ser Lys Gly Gly
50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Ser Gly Thr Tyr Arg Cys Asn Val
                85                  90                  95

Tyr Ser Trp Tyr Gly Tyr Asp Cys Ala Glu Leu Asp Val Tyr Gly Gly
                100                 105                 110

Gly Thr Val Val Thr Val
```

-continued

115

<210> SEQ ID NO 96
<211> LENGTH: 122
<212> TYPE: PRT
<213> ORGANISM: Ginglymostoma cirratum
<220> FEATURE:
<223> OTHER INFORMATION: >gi| 21805808| gb| AAM76810.1+51 antigen
      receptor [Ginglymostoma cirratum]

<400> SEQUENCE: 96

Val Leu Leu Ala Leu Leu Pro Tyr Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Thr Asn Cys Ala Leu Ser Ser Thr Tyr Trp Tyr
        35                  40                  45

His Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Ser Gly Thr Tyr Arg Cys Ile Val
                85                  90                  95

Tyr Gly Trp Tyr Asp Cys Val Glu Leu Asp Arg Asn Tyr Asp Val Tyr
            100                 105                 110

Gly Gly Gly Thr Val Val Thr Val Asn Pro
        115                 120

<210> SEQ ID NO 97
<211> LENGTH: 158
<212> TYPE: PRT
<213> ORGANISM: Ginglymostoma cirratum
<220> FEATURE:
<223> OTHER INFORMATION: >gi| 699417| gb| AAB48359.1| novel
      antigen receptor, partial [Ginglymostoma cirratum]

<400> SEQUENCE: 97

Met Asn Ile Phe Leu Leu Ser Val Leu Leu Ala Leu Leu Pro Tyr Val
1               5                   10                  15

Phe Thr Val Arg Val Asp Gln Thr Pro Gln Thr Ile Thr Lys Glu Thr
            20                  25                  30

Gly Glu Ser Leu Thr Ile Asn Cys Val Leu Arg Asp Ser Asn Cys Ala
        35                  40                  45

Leu Ser Ser Thr Tyr Trp Tyr Arg Lys Lys Ser Gly Ser Thr Asn Glu
    50                  55                  60

Glu Lys Val Ser Lys Gly Gly Arg Tyr Val Glu Thr Val Asn Ser Gly
65                  70                  75                  80

Ser Lys Ser Phe Ser Leu Arg Ile Asn Asp Leu Thr Val Glu Asp Ser
                85                  90                  95

Gly Thr Tyr Arg Cys Lys Thr Gly Met Leu His Asp Cys Asp Trp Ser
            100                 105                 110

Asp Tyr Asp Val Tyr Gly Gly Gly Thr Val Val Thr Val Asn Pro Gly
        115                 120                 125

Ile Pro Leu Ser Pro Pro Ile Val Ser Leu Leu His Ser Ala Thr Glu
    130                 135                 140

Glu Gln Arg Ala Asn Gly Phe Val Gln Leu Val Cys Leu Ile
145                 150                 155

```
<210> SEQ ID NO 98
<211> LENGTH: 108
<212> TYPE: PRT
<213> ORGANISM: Ginglymostoma cirratum
<220> FEATURE:
<223> OTHER INFORMATION: >gi| 21898842| gb| AAM77142.1+51  antigen
      receptor [Ginglymostoma cirratum]

<400> SEQUENCE: 98

Val Leu Leu Ala Leu Leu Pro Tyr Val Phe Thr Ala Arg Val Asp Gln
1               5                   10                  15

Thr Pro Arg Ser Val Thr Lys Glu Thr Gly Glu Ser Leu Thr Ile Asn
            20                  25                  30

Cys Val Leu Arg Asp Ala Ser Tyr Ala Leu Gly Ser Thr Cys Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Gly Thr Tyr Arg Cys Gly Val
                85                  90                  95

Ala Gly Val Arg Cys Asp Tyr Val Leu Tyr Ala Ala
            100                 105

<210> SEQ ID NO 99
<211> LENGTH: 107
<212> TYPE: PRT
<213> ORGANISM: Ginglymostoma cirratum
<220> FEATURE:
<223> OTHER INFORMATION: >gi| 21805883| gb| AAM76843.1+51  antigen
      receptor [Ginglymostoma cirratum]

<400> SEQUENCE: 99

Val Leu Leu Ala Leu Leu Pro Tyr Val Phe Thr Ala Arg Val Asp Gln
1               5                   10                  15

Thr Pro Gln Thr Ile Thr Lys Glu Thr Gly Glu Ser Leu Thr Ile Asn
            20                  25                  30

Cys Val Leu Arg Asp Ser Asn Cys Ala Leu Ser Ser Thr Tyr Trp Tyr
        35                  40                  45

Arg Lys Lys Ser Gly Ser Thr Asn Glu Glu Ser Ile Ser Lys Gly Gly
    50                  55                  60

Arg Tyr Val Glu Thr Val Asn Ser Gly Ser Lys Ser Phe Ser Leu Arg
65                  70                  75                  80

Ile Asn Asp Leu Thr Val Glu Asp Ser Gly Thr Tyr Arg Cys Asn Val
                85                  90                  95

Ser Leu Arg Glu Cys Trp Gly Tyr Asp Val Tyr
            100                 105

<210> SEQ ID NO 100
<211> LENGTH: 115
<212> TYPE: PRT
<213> ORGANISM: Ginglymostoma cirratum
<220> FEATURE:
<223> OTHER INFORMATION: >gi| 21539947| gb| AAM52959.1+51  antigen
      receptor [Ginglymostoma cirratum]

<400> SEQUENCE: 100

Leu Leu Ala Leu Leu Pro Tyr Val Phe Thr Ala Arg Val Asp Gln Thr
1               5                   10                  15

Pro Gln Thr Ile Thr Lys Glu Thr Gly Glu Ser Leu Thr Ile Asn Cys
            20                  25                  30
```

Val Leu Arg Asp Ala Ser Tyr Ala Leu Gly Ser Thr Cys Trp Tyr Arg
              35                  40                  45

Lys Lys Ser Gly Ser Thr Asn Glu Glu Ser Ile Ser Lys Gly Gly Arg
 50                  55                  60

Tyr Val Glu Thr Val Asn Ser Gly Ser Lys Ser Phe Ser Met Arg Ile
 65                  70                  75                  80

Asn Asp Leu Thr Val Glu Asp Ser Gly Thr Phe Arg Cys Gly Val Trp
                 85                  90                  95

Cys Gly Ser Gly Asp Tyr Pro Cys Ala Leu Asp Ser Ala Ala Cys Gly
                100                 105                 110

Gly Gly Thr
        115

<210> SEQ ID NO 101
<211> LENGTH: 113
<212> TYPE: PRT
<213> ORGANISM: artificial sequence
<220> FEATURE:
<223> OTHER INFORMATION: >1SQ2:N| PDBID| CHAIN| SEQUENCE (5A7)

<400> SEQUENCE: 101

Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
                 20                  25                  30

Ser Thr Cys Trp Tyr Arg Lys Lys Ser Gly Glu Gly Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Gly Gly Thr
 65                  70                  75                  80

Tyr Arg Cys Gly Leu Gly Val Ala Gly Gly Tyr Cys Asp Tyr Ala Leu
                 85                  90                  95

Cys Ser Ser Arg Tyr Ala Glu Cys Gly Asp Gly Thr Ala Val Thr Val
                100                 105                 110

Asn

<210> SEQ ID NO 102
<211> LENGTH: 167
<212> TYPE: PRT
<213> ORGANISM: artificial sequence
<220> FEATURE:
<223> OTHER INFORMATION: New antigen receptor (Orectolobus) Q90XW8_
      9CHON aminoacid sequence (Orectolobus maculatus clone 7E-80
      new antigen receptor)

<400> SEQUENCE: 102

Met Asn Ile Phe Leu Leu Ser Val Leu Leu Ala Leu Leu Pro Asn Val
 1               5                  10                  15

Phe Thr Ala Arg Val Asp Gln Thr Pro Arg Thr Ala Thr Lys Glu Thr
                 20                  25                  30

Gly Glu Ser Leu Thr Ile Asn Cys Val Leu Arg Asp Thr Ser Cys Ala
             35                  40                  45

Phe Ser Ser Thr Gly Trp Tyr Arg Thr Lys Leu Gly Ser Thr Asn Glu
         50                  55                  60

Gln Ser Ile Ser Ile Gly Gly Arg Tyr Val Glu Thr Val Asn Lys Gly
 65                  70                  75                  80

Ser Lys Ser Phe Ser Leu Arg Ile Ser Asp Leu Arg Val Glu Asp Ser
            85                  90                  95

Gly Thr Tyr Lys Cys Gln Ala Tyr Val Ile Ala Thr Met Ala Pro Leu
            100                 105                 110

Cys Tyr Ala Ser Tyr Ser Trp Asn Glu Lys Gly Ala Gly Thr Val Leu
        115                 120                 125

Thr Val Lys Pro Gly Val Gln Pro Ser Pro Pro Val Ile Ser Leu Leu
    130                 135                 140

Tyr Ser Ala Thr Glu Glu Gln Arg Gly Asn Gly Phe Val Gln Leu Ile
145                 150                 155                 160

Cys Leu Ile Ser Gly Tyr Tyr
                165

<210> SEQ ID NO 103
<211> LENGTH: 25
<212> TYPE: PRT
<213> ORGANISM: artificial sequence
<220> FEATURE:
<223> OTHER INFORMATION: Alpha-Signal-peptide(from pCLS22370) aminoacid
      sequence

<400> SEQUENCE: 103

Met Ala Pro Ala Met Glu Ser Pro Thr Leu Leu Cys Val Ala Leu Leu
1               5                   10                  15

Phe Phe Ala Pro Asp Gly Val Leu Ala
            20                  25

<210> SEQ ID NO 104
<211> LENGTH: 18
<212> TYPE: PRT
<213> ORGANISM: artificial sequence
<220> FEATURE:
<223> OTHER INFORMATION: Signal-peptide(from Q90XW8_9CHON) aminoacid
      sequence

<400> SEQUENCE: 104

Met Asn Ile Phe Leu Leu Ser Val Leu Leu Ala Leu Leu Pro Asn Val
1               5                   10                  15

Phe Thr

<210> SEQ ID NO 105
<211> LENGTH: 719
<212> TYPE: PRT
<213> ORGANISM: artificial sequence
<220> FEATURE:
<223> OTHER INFORMATION: Chimeric VNAR-CAR2

<400> SEQUENCE: 105

Met Ala Pro Ala Met Glu Ser Pro Thr Leu Leu Cys Val Ala Leu Leu
1               5                   10                  15

Phe Phe Ala Pro Asp Gly Val Leu Ala Met Asn Ile Phe Leu Leu Ser
            20                  25                  30

Val Leu Leu Ala Leu Leu Pro Asn Val Phe Thr Ala Arg Val Asp Gln
        35                  40                  45

Thr Pro Arg Thr Ala Thr Lys Glu Thr Gly Glu Ser Leu Thr Ile Asn
    50                  55                  60

Cys Val Leu Arg Asp Thr Ser Cys Ala Phe Ser Ser Thr Gly Trp Tyr
65              70                  75                  80

Arg Thr Lys Leu Gly Ser Thr Asn Glu Gln Ser Ile Ser Ile Gly Gly
                85                  90                  95

```
Arg Tyr Val Glu Thr Val Asn Lys Gly Ser Lys Ser Phe Ser Leu Arg
                100                 105                 110
Ile Ser Asp Leu Arg Val Glu Asp Ser Gly Thr Tyr Lys Cys Gln Ala
            115                 120                 125
Tyr Val Ile Ala Thr Met Ala Pro Leu Cys Tyr Ala Ser Tyr Ser Trp
        130                 135                 140
Asn Glu Lys Gly Ala Gly Thr Val Leu Thr Val Lys Pro Gly Val Gln
145                 150                 155                 160
Pro Ser Pro Pro Val Ile Ser Leu Leu Tyr Ser Ala Thr Glu Glu Gln
                165                 170                 175
Arg Gly Asn Gly Phe Val Gln Leu Ile Cys Leu Ile Ser Gly Tyr Tyr
            180                 185                 190
Phe Phe Ile Pro Leu Leu Val Val Ile Leu Phe Ala Val Asp Thr Gly
        195                 200                 205
Leu Phe Ile Ser Thr Gln Gln Gln Val Thr Phe Leu Leu Lys Ile Lys
        210                 215                 220
Arg Thr Arg Lys Gly Phe Arg Leu Leu Asn Pro His Pro Lys Pro Asn
225                 230                 235                 240
Pro Lys Asn Asn Arg Ala Glu Gly Arg Gly Ser Leu Leu Thr Cys Gly
                245                 250                 255
Asp Val Glu Glu Asn Pro Gly Pro Met Asp Thr Glu Ser Asn Arg Arg
            260                 265                 270
Ala Asn Leu Ala Leu Pro Gln Glu Pro Ser Ser Val Pro Ala Phe Glu
        275                 280                 285
Val Leu Glu Ile Ser Pro Gln Glu Val Ser Ser Gly Arg Leu Leu Lys
        290                 295                 300
Ser Ala Ser Ser Pro Pro Leu His Thr Trp Leu Thr Val Leu Lys Lys
305                 310                 315                 320
Glu Gln Glu Phe Leu Gly Val Thr Gln Ile Leu Thr Ala Met Ile Cys
                325                 330                 335
Leu Cys Phe Gly Thr Val Val Cys Ser Val Leu Asp Ile Ser His Ile
            340                 345                 350
Glu Gly Asp Ile Phe Ser Ser Phe Lys Ala Gly Tyr Pro Phe Trp Gly
        355                 360                 365
Ala Ile Phe Phe Ser Ile Ser Gly Met Leu Ser Ile Ile Ser Glu Arg
        370                 375                 380
Arg Asn Ala Thr Tyr Leu Val Arg Gly Ser Leu Gly Ala Asn Thr Ala
385                 390                 395                 400
Ser Ser Ile Ala Gly Gly Thr Gly Ile Thr Ile Leu Ile Ile Asn Leu
                405                 410                 415
Lys Lys Ser Leu Ala Tyr Ile His Ile His Ser Cys Gln Lys Phe Phe
            420                 425                 430
Glu Thr Lys Cys Phe Met Ala Ser Phe Ser Thr Glu Ile Val Val Met
        435                 440                 445
Met Leu Phe Leu Thr Ile Leu Gly Leu Gly Ser Ala Val Ser Leu Thr
        450                 455                 460
Ile Cys Gly Ala Gly Glu Glu Leu Lys Gly Asn Lys Val Pro Glu Lys
465                 470                 475                 480
Arg Gly Arg Lys Lys Leu Leu Tyr Ile Phe Lys Gln Pro Phe Met Arg
                485                 490                 495
Pro Val Gln Thr Thr Gln Glu Glu Asp Gly Cys Ser Cys Arg Phe Pro
            500                 505                 510
Glu Glu Glu Glu Gly Gly Cys Glu Leu Gly Ser Gly Val Lys Gln Thr
```

```
                515                 520                 525
Leu Asn Phe Asp Leu Leu Lys Leu Ala Gly Asp Val Glu Ser Asn Pro
        530                 535                 540

Gly Pro Met Ile Pro Ala Val Val Leu Leu Leu Leu Leu Leu Val Glu
545                 550                 555                 560

Gln Ala Ala Ala Leu Gly Glu Pro Gln Leu Cys Tyr Ile Leu Asp Ala
                565                 570                 575

Ile Leu Phe Leu Tyr Gly Ile Val Leu Thr Leu Leu Tyr Cys Arg Leu
            580                 585                 590

Lys Ile Gln Val Arg Lys Ala Ala Ile Thr Ser Tyr Glu Lys Ser Arg
        595                 600                 605

Val Lys Phe Ser Arg Ser Ala Asp Ala Pro Ala Tyr Gln Gln Gly Gln
    610                 615                 620

Asn Gln Leu Tyr Asn Glu Leu Asn Leu Gly Arg Arg Glu Glu Tyr Asp
625                 630                 635                 640

Val Leu Asp Lys Arg Arg Gly Arg Asp Pro Glu Met Gly Gly Lys Pro
                645                 650                 655

Arg Arg Lys Asn Pro Gln Glu Gly Leu Tyr Asn Glu Leu Gln Lys Asp
            660                 665                 670

Lys Met Ala Glu Ala Tyr Ser Glu Ile Gly Met Lys Gly Glu Arg Arg
        675                 680                 685

Arg Gly Lys Gly His Asp Gly Leu Tyr Gln Gly Leu Ser Thr Ala Thr
    690                 695                 700

Lys Asp Thr Tyr Asp Ala Leu His Met Gln Ala Leu Pro Pro Arg
705                 710                 715

<210> SEQ ID NO 106
<211> LENGTH: 918
<212> TYPE: PRT
<213> ORGANISM: artificial sequence
<220> FEATURE:
<223> OTHER INFORMATION: Chimeric VNAR-CAR3

<400> SEQUENCE: 106

Met Ala Pro Ala Met Glu Ser Pro Thr Leu Leu Cys Val Ala Leu Leu
1               5                   10                  15

Phe Phe Ala Pro Asp Gly Val Leu Ala Met Asn Ile Phe Leu Leu Ser
                20                  25                  30

Val Leu Leu Ala Leu Leu Pro Asn Val Phe Thr Ala Arg Val Asp Gln
            35                  40                  45

Thr Pro Arg Thr Ala Thr Lys Glu Thr Gly Glu Ser Leu Thr Ile Asn
        50                  55                  60

Cys Val Leu Arg Asp Thr Ser Cys Ala Phe Ser Ser Thr Gly Trp Tyr
65                  70                  75                  80

Arg Thr Lys Leu Gly Ser Thr Asn Glu Gln Ser Ile Ser Ile Gly Gly
                85                  90                  95

Arg Tyr Val Glu Thr Val Asn Lys Gly Ser Lys Ser Phe Ser Leu Arg
                100                 105                 110

Ile Ser Asp Leu Arg Val Glu Asp Ser Gly Thr Tyr Lys Cys Gln Ala
            115                 120                 125

Tyr Val Ile Ala Thr Met Ala Pro Leu Cys Tyr Ala Ser Tyr Ser Trp
        130                 135                 140

Asn Glu Lys Gly Ala Gly Thr Val Leu Thr Val Lys Glu Pro Lys Ser
145                 150                 155                 160

Pro Asp Lys Thr His Thr Cys Pro Pro Cys Pro Ala Pro Pro Val Ala
```

```
                165                 170                 175
Gly Pro Ser Val Phe Leu Phe Pro Pro Lys Pro Lys Asp Thr Leu Met
                    180                 185                 190
Ile Ala Arg Thr Pro Glu Val Thr Cys Val Val Val Asp Val Ser His
                    195                 200                 205
Glu Asp Pro Glu Val Lys Phe Asn Trp Tyr Val Asp Gly Val Glu Val
                    210                 215                 220
His Asn Ala Lys Thr Lys Pro Arg Glu Glu Gln Tyr Asn Ser Thr Tyr
225                 230                 235                 240
Arg Val Val Ser Val Leu Thr Val Leu His Gln Asp Trp Leu Asn Gly
                    245                 250                 255
Lys Glu Tyr Lys Cys Lys Val Ser Asn Lys Ala Leu Pro Ala Pro Ile
                    260                 265                 270
Glu Lys Thr Ile Ser Lys Ala Lys Gly Gln Pro Arg Glu Pro Gln Val
                    275                 280                 285
Tyr Thr Leu Pro Pro Ser Arg Asp Glu Leu Thr Lys Asn Gln Val Ser
                    290                 295                 300
Leu Thr Cys Leu Val Lys Gly Phe Tyr Pro Ser Asp Ile Ala Val Glu
305                 310                 315                 320
Trp Glu Ser Asn Gly Gln Pro Glu Asn Asn Tyr Lys Thr Thr Pro Pro
                    325                 330                 335
Val Leu Asp Ser Asp Gly Ser Phe Phe Leu Tyr Ser Lys Leu Thr Val
                    340                 345                 350
Asp Lys Ser Arg Trp Gln Gln Gly Asn Val Phe Ser Cys Ser Val Met
                    355                 360                 365
His Glu Ala Leu His Asn His Tyr Thr Gln Lys Ser Leu Ser Leu Ser
                    370                 375                 380
Pro Gly Lys Lys Asp Pro Lys Phe Phe Ile Pro Leu Leu Val Val Ile
385                 390                 395                 400
Leu Phe Ala Val Asp Thr Gly Leu Phe Ile Ser Thr Gln Gln Gln Val
                    405                 410                 415
Thr Phe Leu Leu Lys Ile Lys Arg Thr Arg Lys Gly Phe Arg Leu Leu
                    420                 425                 430
Asn Pro His Pro Lys Pro Asn Pro Lys Asn Asn Arg Ala Glu Gly Arg
                    435                 440                 445
Gly Ser Leu Leu Thr Cys Gly Asp Val Glu Glu Asn Pro Gly Pro Met
                    450                 455                 460
Asp Thr Glu Ser Asn Arg Arg Ala Asn Leu Ala Leu Pro Gln Glu Pro
465                 470                 475                 480
Ser Ser Val Pro Ala Phe Glu Val Leu Glu Ile Ser Pro Gln Glu Val
                    485                 490                 495
Ser Ser Gly Arg Leu Leu Lys Ser Ala Ser Ser Pro Pro Leu His Thr
                    500                 505                 510
Trp Leu Thr Val Leu Lys Lys Glu Gln Glu Phe Leu Gly Val Thr Gln
                    515                 520                 525
Ile Leu Thr Ala Met Ile Cys Leu Cys Phe Gly Thr Val Val Cys Ser
                    530                 535                 540
Val Leu Asp Ile Ser His Ile Glu Gly Asp Ile Phe Ser Ser Phe Lys
545                 550                 555                 560
Ala Gly Tyr Pro Phe Trp Gly Ala Ile Phe Phe Ser Ile Ser Gly Met
                    565                 570                 575
Leu Ser Ile Ile Ser Glu Arg Arg Asn Ala Thr Tyr Leu Val Arg Gly
                    580                 585                 590
```

-continued

Ser Leu Gly Ala Asn Thr Ala Ser Ile Ala Gly Gly Thr Gly Ile
            595                 600                 605

Thr Ile Leu Ile Ile Asn Leu Lys Lys Ser Leu Ala Tyr Ile His Ile
610                 615                 620

His Ser Cys Gln Lys Phe Phe Glu Thr Lys Cys Phe Met Ala Ser Phe
625                 630                 635                 640

Ser Thr Glu Ile Val Val Met Met Leu Phe Leu Thr Ile Leu Gly Leu
            645                 650                 655

Gly Ser Ala Val Ser Leu Thr Ile Cys Gly Ala Gly Glu Glu Leu Lys
            660                 665                 670

Gly Asn Lys Val Pro Glu Lys Arg Gly Lys Lys Leu Leu Tyr Ile
            675                 680                 685

Phe Lys Gln Pro Phe Met Arg Pro Val Gln Thr Thr Gln Glu Asp
            690                 695                 700

Gly Cys Ser Cys Arg Phe Pro Glu Glu Glu Gly Gly Cys Glu Leu
705                 710                 715                 720

Gly Ser Gly Val Lys Gln Thr Leu Asn Phe Asp Leu Leu Lys Leu Ala
            725                 730                 735

Gly Asp Val Glu Ser Asn Pro Gly Pro Met Ile Pro Ala Val Val Leu
            740                 745                 750

Leu Leu Leu Leu Leu Val Glu Gln Ala Ala Ala Leu Gly Glu Pro Gln
            755                 760                 765

Leu Cys Tyr Ile Leu Asp Ala Ile Leu Phe Leu Tyr Gly Ile Val Leu
            770                 775                 780

Thr Leu Leu Tyr Cys Arg Leu Lys Ile Gln Val Arg Lys Ala Ala Ile
785                 790                 795                 800

Thr Ser Tyr Glu Lys Ser Arg Val Lys Phe Ser Arg Ser Ala Asp Ala
            805                 810                 815

Pro Ala Tyr Gln Gln Gly Gln Asn Gln Leu Tyr Asn Glu Leu Asn Leu
            820                 825                 830

Gly Arg Arg Glu Glu Tyr Asp Val Leu Asp Lys Arg Gly Arg Asp
            835                 840                 845

Pro Glu Met Gly Gly Lys Pro Arg Arg Lys Asn Pro Gln Glu Gly Leu
            850                 855                 860

Tyr Asn Glu Leu Gln Lys Asp Lys Met Ala Glu Ala Tyr Ser Glu Ile
865                 870                 875                 880

Gly Met Lys Gly Glu Arg Arg Arg Gly Lys Gly His Asp Gly Leu Tyr
            885                 890                 895

Gln Gly Leu Ser Thr Ala Thr Lys Asp Thr Tyr Asp Ala Leu His Met
            900                 905                 910

Gln Ala Leu Pro Pro Arg
            915

<210> SEQ ID NO 107
<211> LENGTH: 728
<212> TYPE: PRT
<213> ORGANISM: artificial sequence
<220> FEATURE:
<223> OTHER INFORMATION: Chimeric VNAR-CAR4

<400> SEQUENCE: 107

Met Ala Pro Ala Met Glu Ser Pro Thr Leu Leu Cys Val Ala Leu Leu
1               5                   10                  15

Phe Phe Ala Pro Asp Gly Val Leu Ala Met Asn Ile Phe Leu Leu Ser
            20                  25                  30

```
Val Leu Leu Ala Leu Leu Pro Asn Val Phe Thr Ala Arg Val Asp Gln
            35                  40                  45

Thr Pro Arg Thr Ala Thr Lys Glu Thr Gly Glu Ser Leu Thr Ile Asn
50                  55                  60

Cys Val Leu Arg Asp Thr Ser Cys Ala Phe Ser Ser Thr Gly Trp Tyr
65                  70                  75                  80

Arg Thr Lys Leu Gly Ser Thr Asn Glu Gln Ser Ile Ser Ile Gly Gly
                85                  90                  95

Arg Tyr Val Glu Thr Val Asn Lys Gly Ser Lys Ser Phe Ser Leu Arg
                100                 105                 110

Ile Ser Asp Leu Arg Val Glu Asp Ser Gly Thr Tyr Lys Cys Gln Ala
                115                 120                 125

Tyr Val Ile Ala Thr Met Ala Pro Leu Cys Tyr Ala Ser Tyr Ser Trp
                130                 135                 140

Asn Glu Lys Gly Ala Gly Thr Val Leu Thr Val Lys Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
                180                 185                 190

Thr Arg Gly Leu Asp Phe Ala Cys Asp Phe Phe Ile Pro Leu Leu Val
                195                 200                 205

Val Ile Leu Phe Ala Val Asp Thr Gly Leu Phe Ile Ser Thr Gln Gln
                210                 215                 220

Gln Val Thr Phe Leu Leu Lys Ile Lys Arg Thr Arg Lys Gly Phe Arg
225                 230                 235                 240

Leu Leu Asn Pro His Pro Lys Pro Asn Pro Lys Asn Asn Arg Ala Glu
                245                 250                 255

Gly Arg Gly Ser Leu Leu Thr Cys Gly Asp Val Glu Glu Asn Pro Gly
                260                 265                 270

Pro Met Asp Thr Glu Ser Asn Arg Arg Ala Asn Leu Ala Leu Pro Gln
                275                 280                 285

Glu Pro Ser Ser Val Pro Ala Phe Glu Val Leu Glu Ile Ser Pro Gln
                290                 295                 300

Glu Val Ser Ser Gly Arg Leu Leu Lys Ser Ala Ser Ser Pro Pro Leu
305                 310                 315                 320

His Thr Trp Leu Thr Val Leu Lys Lys Glu Gln Glu Phe Leu Gly Val
                325                 330                 335

Thr Gln Ile Leu Thr Ala Met Ile Cys Leu Cys Phe Gly Thr Val Val
                340                 345                 350

Cys Ser Val Leu Asp Ile Ser His Ile Glu Gly Asp Ile Phe Ser Ser
                355                 360                 365

Phe Lys Ala Gly Tyr Pro Phe Trp Gly Ala Ile Phe Phe Ser Ile Ser
370                 375                 380

Gly Met Leu Ser Ile Ile Ser Glu Arg Arg Asn Ala Thr Tyr Leu Val
385                 390                 395                 400

Arg Gly Ser Leu Gly Ala Asn Thr Ala Ser Ser Ile Ala Gly Gly Thr
                405                 410                 415

Gly Ile Thr Ile Leu Ile Ile Asn Leu Lys Lys Ser Leu Ala Tyr Ile
                420                 425                 430

His Ile His Ser Cys Gln Lys Phe Phe Glu Thr Lys Cys Phe Met Ala
                435                 440                 445
```

```
Ser Phe Ser Thr Glu Ile Val Val Met Met Leu Phe Leu Thr Ile Leu
    450                 455                 460

Gly Leu Gly Ser Ala Val Ser Leu Thr Ile Cys Gly Ala Gly Glu Glu
465                 470                 475                 480

Leu Lys Gly Asn Lys Val Pro Glu Lys Arg Gly Arg Lys Lys Leu Leu
                485                 490                 495

Tyr Ile Phe Lys Gln Pro Phe Met Arg Pro Val Gln Thr Thr Gln Glu
                500                 505                 510

Glu Asp Gly Cys Ser Cys Arg Phe Pro Glu Glu Glu Gly Gly Cys
                515                 520                 525

Glu Leu Gly Ser Gly Val Lys Gln Thr Leu Asn Phe Asp Leu Leu Lys
530                 535                 540

Leu Ala Gly Asp Val Glu Ser Asn Pro Gly Pro Met Ile Pro Ala Val
545                 550                 555                 560

Val Leu Leu Leu Leu Leu Val Glu Gln Ala Ala Ala Leu Gly Glu
                565                 570                 575

Pro Gln Leu Cys Tyr Ile Leu Asp Ala Ile Leu Phe Leu Tyr Gly Ile
                580                 585                 590

Val Leu Thr Leu Leu Tyr Cys Arg Leu Lys Ile Gln Val Arg Lys Ala
                595                 600                 605

Ala Ile Thr Ser Tyr Glu Lys Ser Arg Val Lys Phe Ser Arg Ser Ala
610                 615                 620

Asp Ala Pro Ala Tyr Gln Gln Gly Gln Asn Gln Leu Tyr Asn Glu Leu
625                 630                 635                 640

Asn Leu Gly Arg Arg Glu Glu Tyr Asp Val Leu Asp Lys Arg Arg Gly
                645                 650                 655

Arg Asp Pro Glu Met Gly Gly Lys Pro Arg Arg Lys Asn Pro Gln Glu
                660                 665                 670

Gly Leu Tyr Asn Glu Leu Gln Lys Asp Lys Met Ala Glu Ala Tyr Ser
                675                 680                 685

Glu Ile Gly Met Lys Gly Glu Arg Arg Arg Gly Lys Gly His Asp Gly
                690                 695                 700

Leu Tyr Gln Gly Leu Ser Thr Ala Thr Lys Asp Thr Tyr Asp Ala Leu
705                 710                 715                 720

His Met Gln Ala Leu Pro Pro Arg
                725

<210> SEQ ID NO 108
<211> LENGTH: 370
<212> TYPE: PRT
<213> ORGANISM: artificial sequence
<220> FEATURE:
<223> OTHER INFORMATION: Chimeric VNAR-CAR5

<400> SEQUENCE: 108

Met Ala Pro Ala Met Glu Ser Pro Thr Leu Leu Cys Val Ala Leu Leu
1               5                   10                  15

Phe Phe Ala Pro Asp Gly Val Leu Ala Met Asn Ile Phe Leu Leu Ser
                20                  25                  30

Val Leu Leu Ala Leu Leu Pro Asn Val Phe Thr Ala Arg Val Asp Gln
            35                  40                  45

Thr Pro Arg Thr Ala Thr Lys Glu Thr Gly Glu Ser Leu Thr Ile Asn
        50                  55                  60

Cys Val Leu Arg Asp Thr Ser Cys Ala Phe Ser Ser Thr Gly Trp Tyr
65                  70                  75                  80
```

```
Arg Thr Lys Leu Gly Ser Thr Asn Glu Gln Ser Ile Ser Ile Gly Gly
                85                  90                  95

Arg Tyr Val Glu Thr Val Asn Lys Gly Ser Lys Ser Phe Ser Leu Arg
            100                 105                 110

Ile Ser Asp Leu Arg Val Glu Asp Ser Gly Thr Tyr Lys Cys Gln Ala
            115                 120                 125

Tyr Val Ile Ala Thr Met Ala Pro Leu Cys Tyr Ala Ser Tyr Ser Trp
        130                 135                 140

Asn Glu Lys Gly Ala Gly Thr Val Leu Thr Val Lys Pro Gly Val Gln
145                 150                 155                 160

Pro Ser Pro Pro Val Ile Ser Leu Leu Tyr Ser Ala Thr Glu Glu Gln
                165                 170                 175

Arg Gly Asn Gly Phe Val Gln Leu Ile Cys Leu Ile Ser Gly Tyr Tyr
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Gln
            260                 265                 270

Gln Gly Gln Asn Gln Leu Tyr Asn Glu Leu Asn Leu Gly Arg Arg Glu
        275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
        355                 360                 365

Pro Arg
    370

<210> SEQ ID NO 109
<211> LENGTH: 569
<212> TYPE: PRT
<213> ORGANISM: artificial sequence
<220> FEATURE:
<223> OTHER INFORMATION: Chimeric VNAR-CAR6

<400> SEQUENCE: 109

Met Ala Pro Ala Met Glu Ser Pro Thr Leu Leu Cys Val Ala Leu Leu
1               5                   10                  15

Phe Phe Ala Pro Asp Gly Val Leu Ala Met Asn Ile Phe Leu Leu Ser
            20                  25                  30

Val Leu Leu Ala Leu Leu Pro Asn Val Phe Thr Ala Arg Val Asp Gln
        35                  40                  45

Thr Pro Arg Thr Ala Thr Lys Glu Thr Gly Glu Ser Leu Thr Ile Asn
    50                  55                  60
```

```
Cys Val Leu Arg Asp Thr Ser Cys Ala Phe Ser Ser Thr Gly Trp Tyr
 65                  70                  75                  80

Arg Thr Lys Leu Gly Ser Thr Asn Glu Gln Ser Ile Ser Ile Gly Gly
                 85                  90                  95

Arg Tyr Val Glu Thr Val Asn Lys Gly Ser Lys Ser Phe Ser Leu Arg
            100                 105                 110

Ile Ser Asp Leu Arg Val Glu Asp Ser Gly Thr Tyr Lys Cys Gln Ala
        115                 120                 125

Tyr Val Ile Ala Thr Met Ala Pro Leu Cys Tyr Ala Ser Tyr Ser Trp
    130                 135                 140

Asn Glu Lys Gly Ala Gly Thr Val Leu Thr Val Lys Glu Pro Lys Ser
145                 150                 155                 160

Pro Asp Lys Thr His Thr Cys Pro Pro Cys Pro Ala Pro Pro Val Ala
                165                 170                 175

Gly Pro Ser Val Phe Leu Phe Pro Pro Lys Pro Lys Asp Thr Leu Met
            180                 185                 190

Ile Ala Arg Thr Pro Glu Val Thr Cys Val Val Val Asp Val Ser His
        195                 200                 205

Glu Asp Pro Glu Val Lys Phe Asn Trp Tyr Val Asp Gly Val Glu Val
    210                 215                 220

His Asn Ala Lys Thr Lys Pro Arg Glu Glu Gln Tyr Asn Ser Thr Tyr
225                 230                 235                 240

Arg Val Val Ser Val Leu Thr Val Leu His Gln Asp Trp Leu Asn Gly
                245                 250                 255

Lys Glu Tyr Lys Cys Lys Val Ser Asn Lys Ala Leu Pro Ala Pro Ile
            260                 265                 270

Glu Lys Thr Ile Ser Lys Ala Lys Gly Gln Pro Arg Glu Pro Gln Val
        275                 280                 285

Tyr Thr Leu Pro Pro Ser Arg Asp Glu Leu Thr Lys Asn Gln Val Ser
    290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
                325                 330                 335

Val Leu Asp Ser Asp Gly Ser Phe Phe Leu Tyr Ser Lys Leu Thr Val
            340                 345                 350

Asp Lys Ser Arg Trp Gln Gln Gly Asn Val Phe Ser Cys Ser Val Met
        355                 360                 365

His Glu Ala Leu His Asn His Tyr Thr Gln Lys Ser Leu Ser Leu Ser
    370                 375                 380

Pro Gly Lys Lys Asp Pro Lys Ile Tyr Ile Trp Ala Pro Leu Ala Gly
385                 390                 395                 400

Thr Cys Gly Val Leu Leu Leu Ser Leu Val Ile Thr Leu Tyr Cys Lys
                405                 410                 415

Arg Gly Arg Lys Lys Leu Leu Tyr Ile Phe Lys Gln Pro Phe Met Arg
            420                 425                 430

Pro Val Gln Thr Thr Gln Glu Glu Asp Gly Cys Ser Cys Arg Phe Pro
        435                 440                 445

Glu Glu Glu Glu Gly Gly Cys Glu Leu Arg Val Lys Phe Ser Arg Ser
    450                 455                 460

Ala Asp Ala Pro Ala Tyr Gln Gln Gly Gln Asn Gln Leu Tyr Asn Glu
465                 470                 475                 480

Leu Asn Leu Gly Arg Arg Glu Glu Tyr Asp Val Leu Asp Lys Arg Arg
```

```
                    485                 490                 495
Gly Arg Asp Pro Glu Met Gly Lys Pro Arg Lys Asn Pro Gln
            500                 505                 510

Glu Gly Leu Tyr Asn Glu Leu Gln Lys Asp Lys Met Ala Glu Ala Tyr
            515                 520                 525

Ser Glu Ile Gly Met Lys Gly Glu Arg Arg Arg Gly Lys Gly His Asp
            530                 535                 540

Gly Leu Tyr Gln Gly Leu Ser Thr Ala Thr Lys Asp Thr Tyr Asp Ala
545                 550                 555                 560

Leu His Met Gln Ala Leu Pro Pro Arg
                565

<210> SEQ ID NO 110
<211> LENGTH: 379
<212> TYPE: PRT
<213> ORGANISM: artificial sequence
<220> FEATURE:
<223> OTHER INFORMATION: Chimeric VNAR-CAR7

<400> SEQUENCE: 110

Met Ala Pro Ala Met Glu Ser Pro Thr Leu Leu Cys Val Ala Leu Leu
1               5                   10                  15

Phe Phe Ala Pro Asp Gly Val Leu Ala Met Asn Ile Phe Leu Leu Ser
            20                  25                  30

Val Leu Leu Ala Leu Leu Pro Asn Val Phe Thr Ala Arg Val Asp Gln
            35                  40                  45

Thr Pro Arg Thr Ala Thr Lys Glu Thr Gly Glu Ser Leu Thr Ile Asn
        50                  55                  60

Cys Val Leu Arg Asp Thr Ser Cys Ala Phe Ser Ser Thr Gly Trp Tyr
65                  70                  75                  80

Arg Thr Lys Leu Gly Ser Thr Asn Glu Gln Ser Ile Ser Ile Gly Gly
                85                  90                  95

Arg Tyr Val Glu Thr Val Asn Lys Gly Ser Lys Ser Phe Ser Leu Arg
            100                 105                 110

Ile Ser Asp Leu Arg Val Glu Asp Ser Gly Thr Tyr Lys Cys Gln Ala
            115                 120                 125

Tyr Val Ile Ala Thr Met Ala Pro Leu Cys Tyr Ala Ser Tyr Ser Trp
        130                 135                 140

Asn Glu Lys Gly Ala Gly Thr Val Leu Thr Val Lys Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Lys Arg Gly Arg Lys Lys Leu Leu Tyr Ile Phe Lys Gln Pro Phe
225                 230                 235                 240

Met Arg Pro Val Gln Thr Thr Gln Glu Glu Asp Gly Cys Ser Cys Arg
                245                 250                 255

Phe Pro Glu Glu Glu Glu Gly Gly Cys Glu Leu Arg Val Lys Phe Ser
            260                 265                 270

Arg Ser Ala Asp Ala Pro Ala Tyr Gln Gln Gly Gln Asn Gln Leu Tyr
```

```
                    275                 280                 285
Asn Glu Leu Asn Leu Gly Arg Arg Glu Glu Tyr Asp Val Leu Asp Lys
    290                 295                 300

Arg Arg Gly Arg Asp Pro Glu Met Gly Gly Lys Pro Arg Arg Lys Asn
305                 310                 315                 320

Pro Gln Glu Gly Leu Tyr Asn Glu Leu Gln Lys Asp Lys Met Ala Glu
                325                 330                 335

Ala Tyr Ser Glu Ile Gly Met Lys Gly Glu Arg Arg Arg Gly Lys Gly
            340                 345                 350

His Asp Gly Leu Tyr Gln Gly Leu Ser Thr Ala Thr Lys Asp Thr Tyr
        355                 360                 365

Asp Ala Leu His Met Gln Ala Leu Pro Pro Arg
    370                 375

<210> SEQ ID NO 111
<211> LENGTH: 235
<212> TYPE: PRT
<213> ORGANISM: artificial sequence
<220> FEATURE:
<223> OTHER INFORMATION: IgG1 hinge CH2 CH3

<400> SEQUENCE: 111

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
    115                 120                 125

Glu Pro Gln Val Tyr Thr Leu Pro Pro Ser Arg Asp Glu Leu Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
    195                 200                 205

Cys Ser Val Met His Glu Ala Leu His Asn His Tyr Thr Gln Lys Ser
210                 215                 220

Leu Ser Leu Ser Pro Gly Lys Lys Asp Pro Lys
225                 230                 235

<210> SEQ ID NO 112
<211> LENGTH: 45
<212> TYPE: PRT
```

```
<213> ORGANISM: artificial sequence
<220> FEATURE:
<223> OTHER INFORMATION: CD8 alpha hinge

<400> SEQUENCE: 112

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 113
<211> LENGTH: 672
<212> TYPE: PRT
<213> ORGANISM: artificial sequence
<220> FEATURE:
<223> OTHER INFORMATION: >sp| P02786| 89-760 TFR1_HUMAN aminoacid
      sequenceof the extracellular region

<400> SEQUENCE: 113

Cys Lys Gly Val Glu Pro Lys Thr Glu Cys Glu Arg Leu Ala Gly Thr
1               5                   10                  15

Glu Ser Pro Val Arg Glu Pro Gly Glu Asp Phe Pro Ala Ala Arg
            20                  25                  30

Arg Leu Tyr Trp Asp Asp Leu Lys Arg Lys Leu Ser Glu Lys Leu Asp
            35                  40                  45

Ser Thr Asp Phe Thr Gly Thr Ile Lys Leu Leu Asn Glu Asn Ser Tyr
        50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95

Gln His Phe Val Lys Ile Gln Val Lys Asp Ser Ala Gln Asn Ser Val
            100                 105                 110

Ile Ile Val Asp Lys Asn Gly Arg Leu Val Tyr Leu Val Glu Asn Pro
        115                 120                 125

Gly Gly Tyr Val Ala Tyr Ser Lys Ala Ala Thr Val Thr Gly Lys Leu
    130                 135                 140

Val His Ala Asn Phe Gly Thr Lys Lys Asp Phe Glu Asp Leu Tyr Thr
145                 150                 155                 160

Pro Val Asn Gly Ser Ile Val Ile Val Arg Ala Gly Lys Ile Thr Phe
                165                 170                 175

Ala Glu Lys Val Ala Asn Ala Glu Ser Leu Asn Ala Ile Gly Val Leu
            180                 185                 190

Ile Tyr Met Asp Gln Thr Lys Phe Pro Ile Val Asn Ala Glu Leu Ser
        195                 200                 205

Phe Phe Gly His Ala His Leu Gly Thr Gly Asp Pro Tyr Thr Pro Gly
    210                 215                 220

Phe Pro Ser Phe Asn His Thr Gln Phe Pro Pro Ser Arg Ser Ser Gly
225                 230                 235                 240

Leu Pro Asn Ile Pro Val Gln Thr Ile Ser Arg Ala Ala Ala Glu Lys
                245                 250                 255

Leu Phe Gly Asn Met Glu Gly Asp Cys Pro Ser Asp Trp Lys Thr Asp
            260                 265                 270

Ser Thr Cys Arg Met Val Thr Ser Glu Ser Lys Asn Val Lys Leu Thr
        275                 280                 285
```

Val Ser Asn Val Leu Lys Glu Ile Lys Ile Leu Asn Ile Phe Gly Val
    290                 295                 300

Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
                325                 330                 335

Leu Leu Leu Lys Leu Ala Gln Met Phe Ser Asp Met Val Leu Lys Asp
            340                 345                 350

Gly Phe Gln Pro Ser Arg Ser Ile Ile Phe Ala Ser Trp Ser Ala Gly
        355                 360                 365

Asp Phe Gly Ser Val Gly Ala Thr Glu Trp Leu Glu Gly Tyr Leu Ser
    370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Pro Leu Leu Tyr Thr
                405                 410                 415

Leu Ile Glu Lys Thr Met Gln Asn Val Lys His Pro Val Thr Gly Gln
            420                 425                 430

Phe Leu Tyr Gln Asp Ser Asn Trp Ala Ser Lys Val Glu Lys Leu Thr
        435                 440                 445

Leu Asp Asn Ala Ala Phe Pro Phe Leu Ala Tyr Ser Gly Ile Pro Ala
    450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
                485                 490                 495

Lys Val Ala Arg Ala Ala Ala Glu Val Ala Gly Gln Phe Val Ile Lys
            500                 505                 510

Leu Thr His Asp Val Glu Leu Asn Leu Asp Tyr Glu Arg Tyr Asn Ser
        515                 520                 525

Gln Leu Leu Ser Phe Val Arg Asp Leu Asn Gln Tyr Arg Ala Asp Ile
    530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
                565                 570                 575

Lys Thr Asp Arg Phe Val Met Lys Lys Leu Asn Asp Arg Val Met Arg
            580                 585                 590

Val Glu Tyr His Phe Leu Ser Pro Tyr Val Ser Pro Lys Glu Ser Pro
        595                 600                 605

Phe Arg His Val Phe Trp Gly Ser Gly Ser His Thr Leu Pro Ala Leu
    610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
                645                 650                 655

Ala Ala Asn Ala Leu Ser Gly Asp Val Trp Asp Ile Asp Asn Glu Phe
            660                 665                 670

<210> SEQ ID NO 114
<211> LENGTH: 697
<212> TYPE: PRT
<213> ORGANISM: artificial sequence
<220> FEATURE:

<223> OTHER INFORMATION: >sp|Q9UP52|105-801 TFR2_HUMAN aminoacid
      sequence of the extracellular region

<400> SEQUENCE: 114

```
Arg Gly Ser Cys Gln Ala Cys Gly Asp Ser Val Leu Val Val Ser Glu
1               5                   10                  15

Asp Val Asn Tyr Glu Pro Asp Leu Asp Phe His Gln Gly Arg Leu Tyr
                20                  25                  30

Trp Ser Asp Leu Gln Ala Met Phe Leu Gln Phe Leu Gly Glu Gly Arg
            35                  40                  45

Leu Glu Asp Thr Ile Arg Gln Thr Ser Leu Arg Glu Arg Val Ala Gly
        50                  55                  60

Ser Ala Gly Met Ala Ala Leu Thr Gln Asp Ile Arg Ala Ala Leu Ser
65                  70                  75                  80

Arg Gln Lys Leu Asp His Val Trp Thr Asp Thr His Tyr Val Gly Leu
                85                  90                  95

Gln Phe Pro Asp Pro Ala His Pro Asn Thr Leu His Trp Val Asp Glu
                100                 105                 110

Ala Gly Lys Val Gly Glu Gln Leu Pro Leu Glu Asp Pro Asp Val Tyr
            115                 120                 125

Cys Pro Tyr Ser Ala Ile Gly Asn Val Thr Gly Glu Leu Val Tyr Ala
    130                 135                 140

His Tyr Gly Arg Pro Glu Asp Leu Gln Asp Leu Arg Ala Arg Gly Val
145                 150                 155                 160

Asp Pro Val Gly Arg Leu Leu Leu Val Arg Val Gly Val Ile Ser Phe
                165                 170                 175

Ala Gln Lys Val Thr Asn Ala Gln Asp Phe Gly Ala Gln Gly Val Leu
            180                 185                 190

Ile Tyr Pro Glu Pro Ala Asp Phe Ser Gln Asp Pro Pro Lys Pro Ser
        195                 200                 205

Leu Ser Ser Gln Gln Ala Val Tyr Gly His Val His Leu Gly Thr Gly
    210                 215                 220

Asp Pro Tyr Thr Pro Gly Phe Pro Ser Phe Asn Gln Thr Gln Phe Pro
225                 230                 235                 240

Pro Val Ala Ser Ser Gly Leu Pro Ser Ile Pro Ala Gln Pro Ile Ser
                245                 250                 255

Ala Asp Ile Ala Ser Arg Leu Leu Arg Lys Leu Lys Gly Pro Val Ala
            260                 265                 270

Pro Gln Glu Trp Gln Gly Ser Leu Leu Gly Ser Pro Tyr His Leu Gly
        275                 280                 285

Pro Gly Pro Arg Leu Arg Leu Val Val Asn Asn His Arg Thr Ser Thr
    290                 295                 300

Pro Ile Asn Asn Ile Phe Gly Cys Ile Glu Gly Arg Ser Glu Pro Asp
305                 310                 315                 320

His Tyr Val Val Ile Gly Ala Gln Arg Asp Ala Trp Gly Pro Gly Ala
                325                 330                 335

Ala Lys Ser Ala Val Gly Thr Ala Ile Leu Leu Glu Leu Val Arg Thr
            340                 345                 350

Phe Ser Ser Met Val Ser Asn Gly Phe Arg Pro Arg Arg Ser Leu Leu
        355                 360                 365

Phe Ile Ser Trp Asp Gly Gly Asp Phe Gly Ser Val Gly Ser Thr Glu
    370                 375                 380

Trp Leu Glu Gly Tyr Leu Ser Val Leu His Leu Lys Ala Val Val Tyr
385                 390                 395                 400
```

```
Val Ser Leu Asp Asn Ala Val Leu Gly Asp Asp Lys Phe His Ala Lys
            405                 410                 415

Thr Ser Pro Leu Leu Thr Ser Leu Ile Glu Ser Val Leu Lys Gln Val
            420                 425                 430

Asp Ser Pro Asn His Ser Gly Gln Thr Leu Tyr Glu Gln Val Val Phe
            435                 440                 445

Thr Asn Pro Ser Trp Asp Ala Glu Val Ile Arg Pro Leu Pro Met Asp
450                 455                 460

Ser Ser Ala Tyr Ser Phe Thr Ala Phe Val Gly Val Pro Ala Val Glu
465                 470                 475                 480

Phe Ser Phe Met Glu Asp Gln Ala Tyr Pro Phe Leu His Thr Lys
                485                 490                 495

Glu Asp Thr Tyr Glu Asn Leu His Lys Val Leu Gln Gly Arg Leu Pro
                500                 505                 510

Ala Val Ala Gln Ala Val Ala Gln Leu Ala Gly Gln Leu Leu Ile Arg
                515                 520                 525

Leu Ser His Asp Arg Leu Leu Pro Leu Asp Phe Gly Arg Tyr Gly Asp
            530                 535                 540

Val Val Leu Arg His Ile Gly Asn Leu Asn Glu Phe Ser Gly Asp Leu
545                 550                 555                 560

Lys Ala Arg Gly Leu Thr Leu Gln Trp Val Tyr Ser Ala Arg Gly Asp
                565                 570                 575

Tyr Ile Arg Ala Ala Glu Lys Leu Arg Gln Glu Ile Tyr Ser Ser Glu
                580                 585                 590

Glu Arg Asp Glu Arg Leu Thr Arg Met Tyr Asn Val Arg Ile Met Arg
            595                 600                 605

Val Glu Phe Tyr Phe Leu Ser Gln Tyr Val Ser Pro Ala Asp Ser Pro
            610                 615                 620

Phe Arg His Ile Phe Met Gly Arg Gly Asp His Thr Leu Gly Ala Leu
625                 630                 635                 640

Leu Asp His Leu Arg Leu Leu Arg Ser Asn Ser Ser Gly Thr Pro Gly
                645                 650                 655

Ala Thr Ser Ser Thr Gly Phe Gln Glu Ser Arg Phe Arg Arg Gln Leu
                660                 665                 670

Ala Leu Leu Thr Trp Thr Leu Gln Gly Ala Ala Asn Ala Leu Ser Gly
                675                 680                 685

Asp Val Trp Asn Ile Asp Asn Asn Phe
            690                 695

<210> SEQ ID NO 115
<211> LENGTH: 108
<212> TYPE: PRT
<213> ORGANISM: artificial sequence
<220> FEATURE:
<223> OTHER INFORMATION: 12A9 VNAR polypeptide

<400> SEQUENCE: 115

Ala Arg Val Asp Gln Thr Pro Arg Ile Ala Thr Lys Glu Thr Gly Glu
1               5                   10                  15

Ser Leu Thr Ile Asn Cys Val Arg Asp Thr Ala Cys Ala Leu Asp
                20                  25                  30

Ser Thr Asn Trp Tyr Arg Thr Lys Leu Gly Ser Thr Lys Glu Gln Thr
            35                  40                  45

Ile Ser Ile Gly Gly Arg Tyr Ser Glu Thr Val Asp Glu Gly Ser Asn
        50                  55                  60
```

```
Ser Ala Ser Leu Thr Ile Arg Asp Leu Arg Val Glu Asp Ser Gly Thr
 65                  70                  75                  80

Tyr Lys Cys Lys Ala Tyr Arg Arg Cys Ala Phe Asn Thr Gly Val Gly
                 85                  90                  95

Tyr Lys Glu Gly Ala Gly Thr Val Leu Thr Val Lys
            100                 105
```

CHIMERIC ANTIGEN RECEPTOR USING ANTIGEN RECOGNITION DOMAINS DERIVED FROM CARTILAGINOUS FISH

CROSS REFERENCE TO RELATED APPLICATION

This application is a 35 U.S.C. 371 National Phase of PCT Application No. PCT/EP2015/050581, filed Jan. 14, 2015, which claims priority to Danish Patent Application No. PA201470016, filed Jan. 14, 2014. The disclosure of these prior applications are hereby incorporated in their entirety by reference.

FIELD OF THE INVENTION

The present invention relates to the field of cell immunotherapy and more particularly to a new generation of chimeric antigen receptors (CAR), the specificity of which is conferred by VNAR polypeptides derived from monomeric antibodies of cartilaginous fish. The CAR of the invention can be expressed at the surface of immune cells to redirect their specificity toward specific antigens, in particular hollow antigens, such as components of ion channels and efflux pumps conferring drug resistance to malignant cells. The invention opens the way to efficient adoptive immunotherapy strategies, especially for the treatment of refractory cancer forms.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and heavy variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), ICOS and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010). However, for example, some surface antigens will be difficult to target efficiently with classical antibodies as mAbs are not able to access epitopes embedded in the protein structures (e.g. numerous surface receptor may contain the ligand binding pocket). Moreover, single-chain antibody (scFv), CAR comprising the light and heavy variable fragments of a monoclonal antibody joined by a flexible linker have limitations due to their size and structural complexity that renders them problematic to manufacture and to predict their efficacy.

Here, the inventors have alleviated these limitations by creating new Chimeric Antigen Receptors in which antigen specificity is mediated through variable antigen receptors (VNAR) derived from cartilaginous fish.

SUMMARY OF THE INVENTION

Despite their success, IgG molecules have shown practical limitations as part of current CAR constructs. In particular they are large (~150 kDa) tetrameric structures prone to elicit immune reactions and expensive to develop.

VNAR (variable domain of the IgNAR, or Novel Antigen Receptor) forms a unique class of protein that have been identified in the serum of cartilaginous fish. The VNAR can be isolated as a monomeric binding domain of 12-15 kDa in size, i.e a much smaller size than IgG.

VNARs have been identified for several years as possible biotherapeutics based on their robustness and solubility, propensity to bind to antigen clefts and block active sites of enzymes, and high binding affinities for a range of antigens. However, they remain much less well understood structurally and biophysically than other types of antigen receptors. The VNAR domain shares structural features with the T-cell receptor Va and the IgG Vk-chain, but sequence homology with these domains is low (~35%). By contrast to scFv, VNAR polypeptides have the common feature of lacking CDR2 (CDR=Complementarity Determining Region). They usually contain a shorter CDR1 loop but a longer CDR3 loop, which create the main binding surface of the domain.

Given these features, it was not predictable that VNAR would be suitable for the construction of efficient chimeric receptors. Indeed, it had been so far considered that CAR architectures required rather extensive extracellular antigen recognition domains to reach antigens present at the surface of malignant or infected cells.

The invention relates to such new chimeric antigen receptor that includes VNAR polypeptides as antigen recognition domains.

The present invention also relates to the polypeptides encoding these new CARs referred to as "VNAR-CARs" and to methods of engineering immune cells, in particular T-cells, by expression of said cell polypeptides. The immune cells obtainable by these methods should be better tolerated by patient's organism and more slowly destroyed by the immune system.

In more specific embodiments, different architectures are proposed for the VNAR-CARs of the invention depending on their single or multi-chain structure, allowing modulation of the interaction and/or activation of the immune cell upon antigen recognition. The VNAR may also be humanized in order contain less immunogenic sequences, such that T-cells expressing CAR would not trigger immune response from the receiver organism (e.g. human). The T-cells expressing the VNAR CARs can also be genetically engineered for allogeneic therapeutic use, for instance, by disruption of the genes encoding T-cell receptors (ΔTCR).

BRIEF DESCRIPTION OF THE FIGURES

FIG. 1: General structure of VNAR polypeptides used as antigen recognition domains.

FIG. 2: Sequence alignment of four representative exemplary VNAR Scaffolds from Shark corresponding to SEQ ID NO.1 (E06), SEQ ID NO.101 (5A7), SEQ ID NO.102 (7e80) and SEQ ID NO.115 (12A9).

FIGS. 5 and 6: Schematic representations of different exemplary versions of the multi-chain CARs of the present invention (csml to csm10) comprising an extracellular VNAR polypeptide fused to a CD8 stalk/hinge region fused to the transmembrane domain of FcεRI alpha chain, whereas at least one co-strimulatory 41 BB, CD28 and/or CD3 zeta domains are fused to either FcεRI alpha, beta and/or gamma chains.

DETAILED DESCRIPTION OF THE INVENTION

Figures 3, 4:
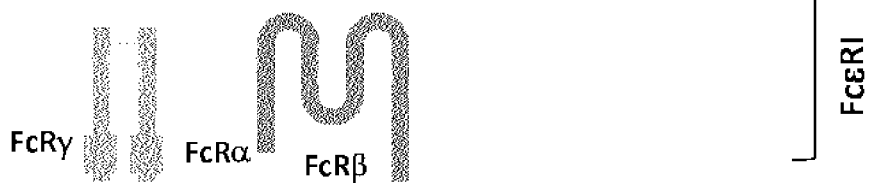
FIG. 3: schematic representation of an exemplary single-chain VNAR-CAR according to the invention comprising (1) an extracellular domain composed of a VNAR polypeptide comprising a CDR3 acting as the main antigen recognition domain and a hinge from CD8, (2) a transmembrane polypeptide comprising 4-1 BB (co-stimulatory domain) and CD3zeta (signaling domain).
FIG. 4: Schematic representation of an exemplary multi-chain VNAR-CARs according to the present invention based on the structure of the FcεRI receptor. The VNAR polypeptide is fused to FcεRI alpha chain, whereas the co-stimulatory domain is fused to FcεRI gamma chain and the signaling domain to the FcεRI beta chain.

Unless specifically defined herein, all technical and scientific terms used have the same meaning as commonly understood by a skilled artisan in the fields of gene therapy, biochemistry, genetics, and molecular biology.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

The present invention primary focuses on a chimeric antigen receptor (CAR) characterized in that it comprises:
 i) one extracellular antigen recognition domain comprising a VNAR polypeptide; and
 ii) one transmembrane polypeptide comprising at least one signal-transducing domain;

VNAR polypeptides are distinct from typical Ig VH and VL domains, as well as from camelid VHH domains, in particular by sharing higher structural homology to immunoglobulin VL and T-cell receptor (TCR) V domains than with immunoglobulin VH.

The most unique feature of VNAR polypeptides is the absence of a CDR2 loop and of two β-strands, C' and C", associated with it. Instead, a distinct "belt" is formed round the middle of the β-sandwich structure (Kovalenko et al., 2013). This region shows an elevated rate of somatic mutations and has thus been termed hypervariable region 2, HV2). Another region of increased mutation frequency is located between HV2 and CDR3, comprising a loop that links β-strands D and E similar to that in TCR V chains; thus, this region was termed HV4. Structurally, HV2 is most proximal to CDR3, whereas HV4 is in proximity to CDR1. Several structural types of IgNAR variable domains have been classified based on the number and position of extra cysteine residues in CDRs and frameworks (FW) in addition to the canonical cysteine pair (Cys-23/Cys-88 for VL, Kabat nomenclature) of the Ig fold. Type I V-NAR, found in nurse sharks, has 2 cysteines in CDR3 and 2 more in frameworks (FW2 and FW4). The more common type II has one extra cysteine pair that links CDR1 and CDR3. Type III, detected primarily in neonatal shark development, is similar to type II but has a conserved Trp residue in CDR1 and limited CDR3 diversity. Another structural type of V-NAR, which we have termed type IV, has 3 only two canonical cysteine residues. So far, this type has been found primarily in dogfish sharks, and was also isolated from semi-synthetic V-NAR libraries derived from wobbegong sharks. The single-domain nature and the lack of CDR2 in V-NARs heighten the requirement for CDR1 and CDR3 to provide specific and high-affinity binding to prospective antigens. CDR3, being more variable in terms of sequence, length and conformation, plays the key role in antigen recognition.

Also, the antigen recognition domain of the CAR according to the invention preferably comprises only two Complementary Determining Regions (CDRs) referred to as CDR1 and CDR3, and more preferably, said antigen recognition domain has only one Complementary Determining Regions (CDR3).

In general, the specificity of recognition of the CAR for said antigen is determined by said CDR3. Most of the time, CDR3 accounts by more than 50%, and more generally by more than 70% in the T-cell activation (i.e. affinity is only reduced by 50 or 30% when CDR1 is modified or removed). T-cell activation can be measured by different means, in particular by using the method described by Betts et al. (2003).

VNAR polypeptides having the advantage of being relatively small polypeptides (12-13 kDa), they demonstrate the advantage of high biophysical stability, solubility and ability to bind to a variety of antigens, including epitopes located in clefts on protein surfaces (e.g. enzyme active sites) that are non-accessible by traditional antibody variable domains.

According to a preferred embodiment of the invention, the CDR3 region, which is often long between 10 to 25 residues, but preferably between 15 to 20, protrudes from the VNAR surface. This CD3 region preferably comprises at least two cysteine residues creating disulfide bounds with residues from the VNAR polypeptide to obtain a more protruding recognition surface.

The term "extracellular antigen recognition domain" as used herein is defined as an oligo- or polypeptide that is capable of binding a ligand, more specifically an antigen. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells. In particular, the extracellular ligand-binding domain can comprise an antigen binding domain derived from an antibody against an antigen of the target.

As non-limiting examples, the antigen of the target can be any cluster of differentiation molecules (e.g. CD16, CD64, CD78, CD96, CLL1, CD116, CD117, CD71, CD45, CD71, CD123 and CD138), a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), GM-CSF, cytokine receptors, a major histocompatibility complex (MHC) molecule, BCMA (CD269, TNFRSF 17), or a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface markers. Antigens are not necessarily surface marker antigens but can be also endogenous small antigens presented by HLA class I at the surface of the cells.

The extracellular ligand-binding domain can also comprise a peptide binding an antigen of the target, a peptide or a protein binding an antibody that binds an antigen of the target, a peptide or a protein ligand such as a growth factor, a cytokine or a hormone as non-limiting examples binding a receptor on the target, or a domain derived from a receptor such as a growth factor receptor, a cytokine receptor or a hormone receptor as non-limiting examples, binding a peptide or a protein ligand on the target. Preferably the target is a cell, but can also be a virus or a microorganism. According to another aspect of the invention, the CARs according to the invention can be directed against antibodies or against other CARs comprising Fc immunoglobulin chains.

The chimeric antigen receptors according to the present invention display the advantage of having an extracellular domain smaller than other types of ligand binding domains. In general the VNAR polypeptide which forms this extracellular domain is shorter than 150 amino acids, preferably shorter than 140, more preferably shorter than 130, even more preferably shorter than 120 amino acids. In some instances, the VNAR polypeptide can be of less than 110 amino acids and sometimes less than 100 amino acids.

The inventors have established that the CARs of smaller extracellular domains according to the present invention could be particularly efficient to target antigens with a hollow structure present at the surface of cells, such as polypeptides involved into transport function. Indeed, Leukemias, as other cancers, bear several genetic alterations of tumor-related genes, such as point mutations, translocations, epigenetic modifications, often accompanied by gene amplification or inactivation. The identification of tumor-related genes provides considerable insight into the biology of leukemias and opens the way to more specific pharmacological treatments. These genes comprise several ion channels and pumps, as the transport mechanisms associated with volume control, proliferation and apoptosis are often altered in cancers. In leukemic cells, such changes are observed as early as the stem cell stage. Ion channels can regulate other malignant features, such as lack of differentiation, increased migratory and invasive phenotype and chemoresistance. Multidrug resistance (MDR), mediated by multiple drug efflux ATP-binding cassette (ABC) transporters, is a critical issue, particularly in the treatment of acute leukemia, with permeability (P)-glycoprotein (P-gp), multidrug resistance-associated protein 1 (MRP1), and breast cancer resistance protein (BCRP, or ABCG2) consistently shown to be the key effectors of MDR in cell line studies. Studies have demonstrated that intrinsic MDR can arise due to specific gene expression profiles, and that drug-induced overexpression of P-gp and other MDR proteins can result in acquired resistance, with multiple ABC transporters having been shown to be overexpressed in cell lines selected for resistance to multiple drugs for acute leukemia. Other receptors such as sigma receptors (sigmaR)(S), namely sigmaR(1) and sigmaR(2), have been found to be overexpressed in breast cancer cells.

Thus because of their involvement in the genesis of cancer and their overexpression in this pathology, one aspect of the present invention would be to target such type of membrane pores or pumps using the CAR of the present invention for immunoadoptive therapy of cancer.

Table 1 below provides examples of ABC transporters, which could be targeted with the VNAR-CAR of the present invention for the treatment of malignant cells resistant to chemotherapy.

TABLE 1

ABC transporters involved into cell resistance to chemotherapy

| ABC family | Chemotherapy substrates | Related cancer |
| --- | --- | --- |
| ABCA | | |
| ABCA2 | Estramustine and mitoxantrone | Lung cancer cell lines and AML |
| ABCA3 | Anthracyclines | Neuroblastoma |
| ABCB | | |
| ABCB1 | Colchicine, Anthracyclines, epipodophyllotoxins, vinca alkaloids, | AML and Lung cancer cell lines |

TABLE 1-continued

ABC transporters involved into cell resistance to chemotherapy

| ABC family | Chemotherapy substrates | Related cancer |
|---|---|---|
| | taxanes, camptothecins, bisantrene, imatinib, mitoxantrone, saquinivir, methotrexate and actinomycin D | |
| ABCB4 | Anthracyclines, vinca alkaloids, taxanes, mitoxantrone, epipodophyllotoxins | |
| ABCB5 | Anthracyclines, camptothecins et thiopurines | Melanoma |
| ABCB11 | Taxanes | |
| ABCC | | |
| ABCC1 | Anthracyclines, mitoxantrone, vinca alkaloids, imatinib, epipodophyllotoxins, camptothecins, mitoxantrone and saquinivir, Methotrexate | Squamous cell carcinoma lines, lung cancer lines, glioma and AML |
| ABCC2 | Methotrexate, epipodophyllotoxins, vinca alkaloids, ciplatin, taxanes, anthracyclines, mitoxantrone, saquinivir, camptotechins | |
| ABCC3 | Methotrexate, epipodophyllotoxins, | |
| ABCC4 | Thiopurines, PMEA, methotrexate, AZT, camptotechins | |
| ABCC5 | Thiopurines, PMEA, methotrexate, AZT, cisplatin | |
| ABCC6 | anthracyclines, cisplatin, epipodophyllotoxins, | |
| ABCC10 | Vinca alkaloids, ciplatin | |
| ABCC11 | Thiopurines | |
| ABCG | | |
| ABCG2 | Mitoxantrone, camptotechins, anthracyclines, bisantrene imitaninib, methotrexate, flavopiridol, epipodophyllotoxins, | Lung cancer, AML, oesophageal carcinoma, glioma, neuroblastoma, squamous cell, carcinoma cell lines, melanoma, ovarian cancer and nasopharyngeal carcinoma cell lines |

According to a particular embodiment of the invention, several VNAR polypeptides can be linked in tandem to provide multi-specificity, the increase size of the extracellular domain or in vivo half-life of molecule.

According to a further aspect of the invention, the VNAR polypeptide involved into the CAR construction can be humanized in order to reduce immunogenicity and/or improve thermodynamic stability, folding and expression properties. Considerable expertise has been accumulated in this subject area, particularly with rodent mAbs. Typically, CDRs of a murine antibody of interest are grafted onto an appropriate human germline framework (selected for sequence similarity, expression properties, or both) and then back-mutations are introduced at key positions responsible for particular CDR conformation and thus antigen binding. This approach has yielded many humanized Abs, with a number of them making it into the clinic. Although shark VNARs represent more challenge for humanization due to the structural differences (e.g., lack of CDR2) and low overall sequence identity (generally ~30%) to human VH/VL sequences, available crystal structures of VNAR domains demonstrate similar organization of key framework regions to human Ig variable domains, thus making an attempt at humanization possible (Kovelenko et al. 2013). Such humanization may lead to the replacement of up to 50% of the initial overall amino acid sequence of the initial VNAR scaffold used as VNAR polypeptide. Accordingly, the present invention encompass the use of VNAR polypeptides having relatively low amino acid identity with any reported VNAR polypeptides originating from cartilaginous fish, although displaying preferably at least 50%, more preferably at least 75%, even more preferably at least 80%, most preferably at least 90% amino acid sequence identity with the polypeptide sequences referred to as SEQ ID NO. 1 to 100 (Table 2). These sequences are provided as non-limiting examples of VNAR scaffold that can be used and humanized according to the invention.

The Chimeric Antigen Receptors according to the present invention generally further comprise a hinge (stalk) region between their transmembrane region and extracellular antigen recognition domain.

The term "hinge region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence. In a preferred embodiment said stalk region is a part of human CD8 alpha chain (e.g. NP_001139345.1).

Multi-Chain VNAR-CARs

Figure 7:
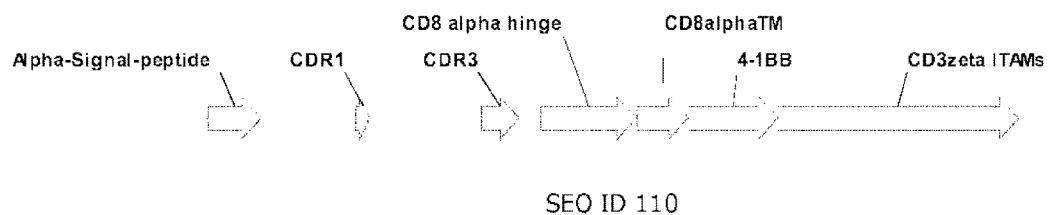
FIG. 7: schematic representation of the structure of the single-chain CAR according to the invention (SEQ ID NO.110) as described in example 1.

Example 1 and FIGS. 3 and 7 of the present specification illustrate Chimeric Antigen Receptors according to the invention based on a single-chain CAR, corresponding to the classical architecture of CARs, in which all relevant domains are contained within a single polypeptide as described in U.S. Pat. No. 7,741,465.

Figure 5:
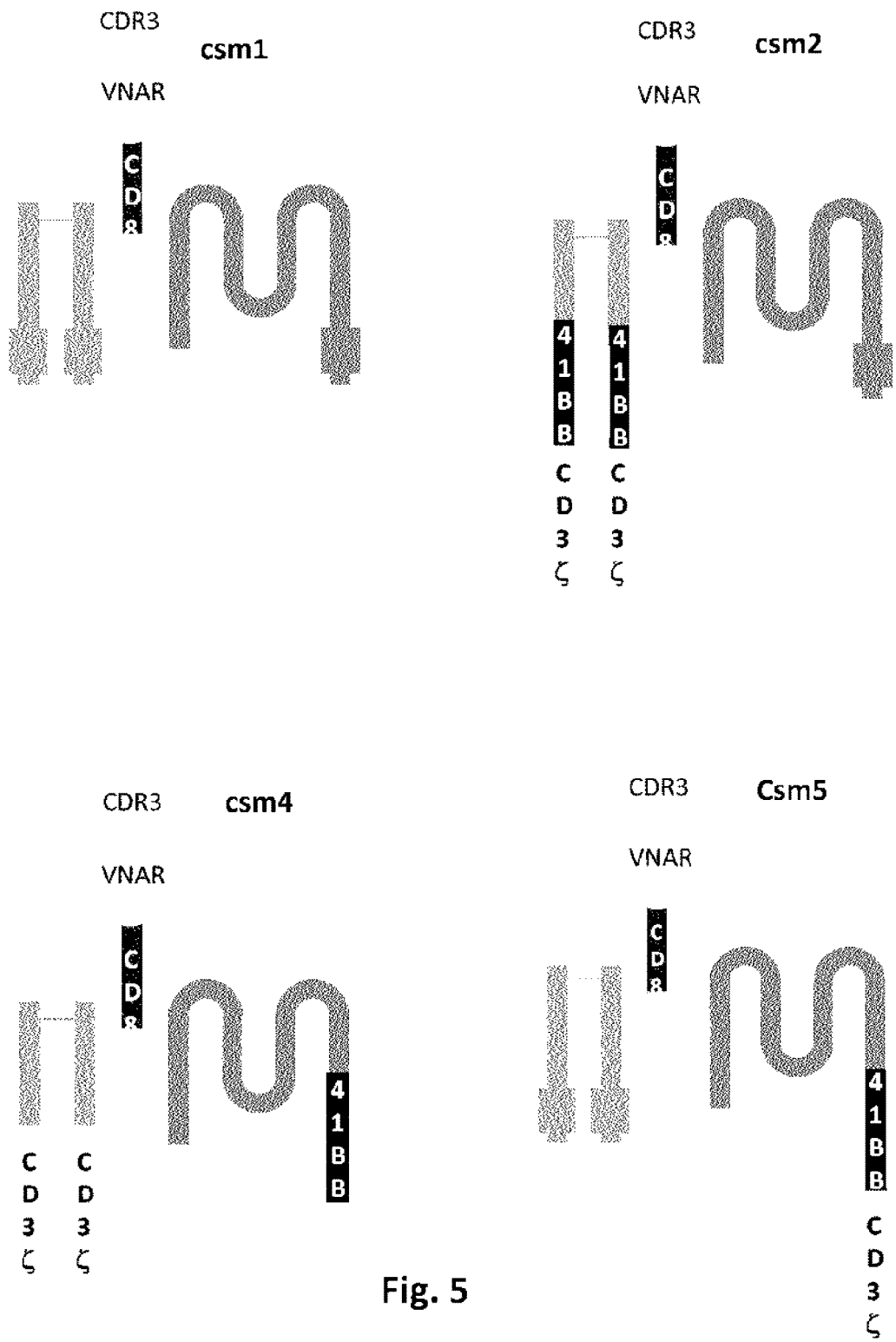
Figure 8:
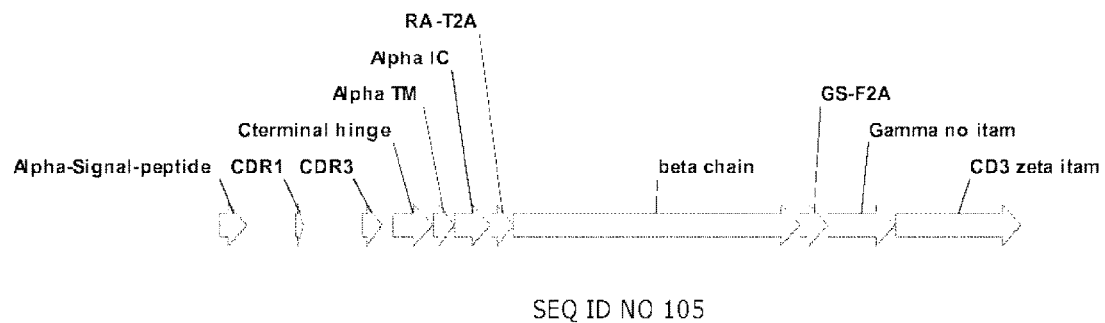
FIG. 8: schematic representation of the structure of a multi-chain CAR according to the invention (SEQ ID NO.105) as described in example 1.

However, the present invention encompasses also multi-chain architectures as shown in Example 2 and FIGS. 4, 5 and 8. According to such architectures, ligands binding domains and signaling domains are born on separate polypeptides. The different polypeptides are anchored into the membrane in a close proximity allowing interactions with each other. In such architectures, the signaling and co-stimulatory domains can be in juxtamembrane positions (i.e. adjacent to the cell membrane on the internal side of it), which is deemed to allow improved function of co-stimulatory domains. The multi-subunit architecture also offers more flexibility and possibilities of designing CARs with more control on T-cell activation. For instance, it is possible to include several extracellular antigen recognition domains having different specificity to obtain a multi-specific CAR architecture. It is also possible to control the relative ratio between the different subunits into the multi-chain CAR. This type of architecture has been recently described by the applicant in PCT/US2013/058005.

The assembly of the different chains as part of a single multi-chain CAR is made possible, for instance, by using the different alpha, beta and gamma chains of the high affinity receptor for IgE (FcεRI) (Metzger, Alcaraz et al. 1986) to which are fused the signaling and co-stimulatory domains. The gamma chain comprises a transmembrane region and cytoplasmic tail containing one immunoreceptor tyrosine-based activation motif (ITAM) (Cambier 1995).

The multi-chain CAR can comprise several extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the multichain CAR. In another embodiment, the present invention relates to a population of multi-chain CARs comprising each one different extracellular ligand binding domains. In a particular, the present invention relates to a method of engineering immune cells comprising providing an immune cell and expressing at the surface of said cell a population of multi-chain CAR each one comprising different extracellular ligand binding domains. In another particular embodiment, the present invention relates to a method of engineering an immune cell comprising providing an immune cell and introducing into said cell polynucleotides encoding polypeptides composing a population of multi-chain CAR each one comprising different extracellular ligand binding domains. In a particular embodiment the method of engineering an immune cell comprises expressing at the surface of the cell at least a part of FcεRI beta and/or gamma chain fused to a signal-transducing domain and several part of FcεRI alpha chains fused to different extracellular ligand binding domains. In a more particular embodiment, said method comprises introducing into said cell at least one polynucleotide which encodes a part of FcεRI beta and/or gamma chain fused to a signal-transducing domain and several FcεRI alpha chains fused to different extracellular ligand binining domains. By population of multi-chain CARs, it is meant at least two, three, four, five, six or more multi-chain CARs each one comprising different extracellular ligand binding domains. The different extracellular ligand binding domains according to the present invention can preferably simultaneously bind different elements in target thereby augmenting immune cell activation and function.

The present invention also relates to an isolated immune cell which comprises a population of multi-chain CARs each one comprising different extracellular ligand binding domains.

The signal transducing domain or intracellular signaling domain of the multi-chain CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the multi-chain CAR is expressed. For example, the effector function of a T cell can be a cytolytic activity or helper activity including the secretion of cytokines.

In the present application, the term "signal transducing domain" refers to the portion of a protein which transduces the effector signal function signal and directs the cell to perform a specialized function.

Preferred examples of signal transducing domain for use in single or multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the multi-chain CAR can comprise the CD3zeta signaling domain, or the intracytoplasmic domain of the FcεRI beta or gamma chains.

In particular embodiment the signal transduction domain of the multi-chain CAR of the present invention comprises a co-stimulatory signal molecule. A co-stimulatory molecule is a cell surface molecule other than an antigen receptor or their ligands that is required for an efficient immune response.

"Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

A "co-stimulatory signal" as used herein refers to a signal, which in combination with primary signal, such as TCR/CD3 ligation, leads to T cell proliferation and/or upregulation or downregulation of key molecules.

In another particular embodiment, said signal transducing domain is a TNFR-associated Factor 2 (TRAF2) binding motifs, intracytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization. In a preferred embodiment, the signal transduction domain of the multi-chain CAR of the present invention comprises a part of co-stimulatory signal molecule selected from the group consisting of 4-1BB (GenBank: AAA53133.) and CD28 (NP_006130.1).

The distinguishing features of appropriate transmembrane polypeptides comprise the ability to be expressed at the surface of an immune cell, in particular lymphocyte cells or Natural killer (NK) cells, and to interact together for directing cellular response of immune cell against a predefined target cell. The different transmembrane polypeptides of the multi-chain CAR of the present invention comprising an extracellular ligand-biding domain and/or a signal transducing domain interact together to take part in signal transduction following the binding with a target ligand and induce an immune response. The transmembrane domain can be derived either from a natural or from a synthetic source. The transmembrane domain can be derived from any membrane-bound or transmembrane protein. As non-limiting examples, the transmembrane polypeptide can be a subunit of the T cell receptor such as α, β, γ or □, polypeptide constituting CD3 complex, IL2 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine.

In a preferred embodiment, the transmembrane polypeptide derived from the Fcε receptor chains or variant thereof, in particular comprises the FcεRI α, β and/or γ chains or a functional fragment or variant thereof. The term "derived from" means a polypeptide having an amino acid sequence which is equivalent to that an Fcε receptor which include one or more amino acid modification(s) of the sequence of the Fcε receptor. Such amino acid modification(s) may include amino acid substitution(s), deletion(s), addition(s) or a combination of any of those modifications, and may alter the biological activity of the Fc binding region relative to that of an Fc receptor. On the other hand, Fc binding regions derived from a particular Fc receptor may include one or more amino acid modification(s) which do not substantially alter the biological activity of the Fc binding region relative to that of an Fc receptor. Amino acid modification(s) of this kind will typically comprise conservative amino acid substitution(s).

In more particular embodiment, said multi-chain CAR can comprise a part of FcεRI alpha chain and a part of FcεRI beta chain or variant thereof such that said FcεRI chains spontaneously dimerize together to form a dimeric Chimeric Antigen Receptor. In another embodiment, the multi-chain Chimeric Antigen can comprise a part of FcεRI alpha chain and a part of a FcεRI gamma chain or variant thereof such that said FcεRI chains spontaneously trimerize together to form a trimeric Chimeric Antigen Receptor, and in another embodiment the multi-chain Chimeric Antigen Receptor can comprise a part of FcεRI alpha chain, a part of FcεRI beta chain and a part of FcεRI gamma chain or variants thereof such that said FcεRI chains spontaneously tetramerize together to form a tetrameric Chimeric Antigen Receptor.

In other words, the multi-chain CAR comprising at least two of the following components:
 a) one polypeptide comprising a part of FcεRI alpha chain and an extracellular ligand-binding domain,
 b) one polypeptide comprising a part of FcεRI beta chain and/or
 c) one polypeptide comprising a part FcεRI gamma chain, whereby different polypeptides multimerize together spontaneously to form dimeric, trimeric or tetrameric CAR.

The term "functional fragment" used herein refers to any subset of a protein, retaining at least 50% of the activity of the whole protein. Alternatively, the term "functional variants" refers to a polypeptide that can include, for example, deletions, or insertions or substitutions of amino acids with respect to an initial protein, while retaining at least 50% of the activity of said initial protein. Such functional variants can be prepared by mutations in the DNA which encodes the polypeptide.

The functionality of the CARs of the invention with respect to a desired antigen can be assayed upon binding to Daudi cells expressing said antigen on their surface as described in the experimental part. Other assays known in the art are available involving measurement of the increase of calcium ion release, intracellular tyrosine phosphorylation, inositol phosphate turnover, or interleukin (IL) 2, interferon γ, GM-CSF, IL-3, IL-4 production by the targeted cells.

Polynucleotides, Vectors:

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the different polypeptides of the multi-chain CAR.

To direct, transmembrane polypeptide such as FcεR into the secretory pathway of a host cell, a secretory signal sequence (also known as a leader sequence, prepro sequence or pre sequence) is provided in polynucleotide sequence or vector sequence. The secretory signal sequence may be that of FcεR, or may be derived from another secreted protein (e.g., t-PA) or synthesized de novo. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In a preferred embodiment the signal peptide comprises the residues 1 to 25 of the FcεRI alpha chain (NP_001992.1).

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into animal cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Modified and Engineered T-Cells

The present invention also relates to isolated cells or cell lines susceptible to be obtained by said method to engineer cells. In particular said isolated cell comprises at least one multi-chain CAR as described above. In another embodiment, said isolated cell comprises a population of multi-chain CARs each one comprising different extracellular ligand binding domains. In particular, said isolated cell comprises exogenous polynucleotide sequences encoding polypeptides composing at least one multi-chain CAR. Said cells can also further comprise at least one inactivated gene selected from the group consisting of CD52, GR, TCR alpha, TCR beta, HLA gene, immune check point genes such as PD1 and CTLA-4, or can express a pTalpha transgene.

In the scope of the present invention is also encompassed an isolated immune cell, preferably a T-cell obtained according to any one of the methods previously described. Said immune cell refers to a cell of hematopoietic origin functionally involved in the initiation and/or execution of innate and/or adaptative immune response. Said immune cell according to the present invention can be derived from a stem cell. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

In another embodiment, said isolated cell according to the present invention comprises one inactivated gene selected from the group consisting of CD52, GR, PD1, CTLA-4, LAG3, Tim3, BTLA, BY55, TIGIT, B7H5, LAIR1, SIGLEC10, 2B4, HLA, TCR alpha and TCR beta and/or expresses a CAR, a multi-chain CAR and/or a pTalpha transgene. In another particular embodiment, said isolated cell comprises polynucleotides encoding said polypeptides composing the CAR of the invention as previously described.

In another embodiment, said isolated cell according to the present invention comprises two inactivated genes selected from the group consisting of CD52 and GR, CD52 and TCR alpha, CD52 and TCR beta, GR and TCR alpha, GR and TCR beta, TCR alpha and TCR beta, PD1 and TCR alpha, PD1 and TCR beta, CTLA-4 and TCR alpha, CTLA-4 and TCR beta, LAG3 and TCR alpha, LAG3 and TCR beta, Tim3 and TCR alpha, Tim3 and TCR beta, BTLA and TCR alpha, BTLA and TCR beta, BY55 and TCR alpha, BY55 and TCR beta, TIGIT and TCR alpha, TIGIT and TCR beta, B7H5 and TCR alpha, B7H5 and TCR beta, LAIR1 and TCR alpha, LAIR1 and TCR beta, SIGLEC10 and TCR alpha, SIGLEC10 and TCR beta, 2B4 and TCR alpha, 2B4 and TCR beta and/or expresses a CAR, a multi-chain CAR and/or a pTalpha transgene.

In a further embodiment, TCR is rendered not functional in the cells according to the invention by inactivating TCR alpha gene and/or TCR beta gene(s). The above strategies are used more particularly to avoid GvHD. In a particular aspect of the present invention is a method to obtain modified cells derived from an individual, wherein said cells can proliferate independently of the Major Histocompatibility Complex signaling pathway. Said method comprises the following steps:
(a) Recovering cells from said individual;
(b) Genetically modifying said cells ex-vivo by inactivating TCR alpha or TCR beta genes;
(c) Cultivating genetically modified T-cells in vitro in appropriate conditions to amplify said cells.

Modified cells, which can proliferate independently of the Major Histocompatibility Complex signaling pathway, susceptible to be obtained by this method are encompassed in the scope of the present invention. Said modified cells can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

Immunosuppressive resistant T cells:
In a particular aspect, one of the steps of genetically modifying cells can be a method comprising:
(a) modifying T-cells by inactivating at least one gene expressing a target for an immunosuppressive agent, and (b) Expanding said cells, optionally in presence of said immunosuppressive agent.

An immunosuppressive agent is an agent that suppresses immune function by one of several mechanisms of action. In other words, an immunosuppressive agent is a role played by a compound which is exhibited by a capability to diminish the extent and/or voracity of an immune response. As non-limiting example, an immunosuppressive agent can be a calcineurin inhibitor, a target of rapamycin, an interleukin-2 α-chain blocker, an inhibitor of inosine monophosphate dehydrogenase, an inhibitor of dihydrofolic acid reductase, a corticosteroid or an immunosuppressive antimetabolite. Classical cytotoxic immunosuppressants act by inhibiting DNA synthesis. Others may act through activation of T-cells or by inhibiting the activation of helper cells. The method according to the invention allows conferring immunosuppressive resistance to T cells for immunotherapy by inactivating the target of the immunosuppressive agent in T cells. As non-limiting examples, targets for immunosuppressive agent can be a receptor for an immunosuppressive agent such as: CD52, glucocorticoid receptor (GR), a FKBP family gene member and a cyclophilin family gene member.

By inactivating a gene it is intended that the gene of interest is not expressed in a functional protein form. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. In a particular embodiment, said method to engineer cells comprises at least one of the following steps:
(a) Providing a T-cell, preferably from a cell culture or from a blood sample;
(b) Selecting a gene in said T-cell expressing a target for an immunosuppressive agent;
(c) Introducing into said T-cell a rare-cutting endonuclease able to selectively inactivate by DNA cleavage, preferably by double-strand break said gene encoding a target for said immunosuppressive agent, and
(d) Expanding said cells, optionally in presence of said immunosuppressive agent.

In a more preferred embodiment, said method comprises:
(a) Providing a T-cell, preferably from a cell culture or from a blood sample;
(b) Selecting a gene in said T-cell expressing a target for an immunosuppressive agent;
(c) Transforming said T cell with nucleic acid encoding a rare-cutting endonuclease able to selectively inactivate by DNA cleavage, preferably by double-strand break said gene encoding a target for said immunosuppressive agent, and
(d) Expressing said rare-cutting endonucleases into said T-cells;
(e) Expanding said cells, optionally in presence of said immunosuppressive agent.

In particular embodiment, said rare-cutting endonuclease specifically targets one gene selected from the group consisting of CD52, GR. In another embodiment, said gene of step (b), specific for an immunosuppressive treatment, is CD52 and the immunosuppressive treatment of step (d) or (e) comprises a humanized antibody targeting CD52 antigen.

In another embodiment, said gene of step (b), specific for an immunosuppressive treatment, is a glucocorticoid receptor (GR) and the immunosuppressive treatment of step d) or (e) comprises a corticosteroid such as dexamethasone.

In another embodiment, said target gene of step (b), specific for an immunosuppressive treatment, is a FKBP family gene member or a variant thereof and the immunosuppressive treatment of step (d) or (e) comprises FK506 also known as Tacrolimus or fujimycin. In another embodiment, said FKBP family gene member is FKBP12 or a variant thereof.

In another embodiment, said gene of step (b), specific for an immunosuppressive treatment, is a cyclophilin family gene member or a variant thereof and the immunosuppressive treatment of step (d) or (e) comprises cyclosporine.

Highly active T cells for immunotherapy

In a particular aspect, one particular step of genetically modifying cell can be a method comprising:
(a) modifying T-cells by inactivating at least one immune checkpoint gene; and
(b) expanding said cells.

T cell-mediated immunity includes multiple sequential steps involving the clonal selection of antigen specific cells, their activation and proliferation in secondary lymphoid tissue, their trafficking to sites of antigen and inflammation, the execution of direct effector function and the provision of help (through cytokines and membrane ligands) for a multitude of effector immune cells. Each of these steps is regulated by counterbalancing stimulatory and inhibitory signal that fine-tune the response. It will be understood by those of ordinary skill in the art, that the term "immune checkpoints" means a group of molecules expressed by T cells. These molecules effectively serve as "brakes" to down-modulate or inhibit an immune response. Immune checkpoint molecules include, but are not limited to Programmed Death 1 (PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as VSTM3, accession number: NM_173799), B7H5 (also known as C10orf54, homolog of mouse vista gene, accession number: NM_022153.1), LAIR1 (also known as CD305, GenBank accession number: CR542051.1), SIGLEC10 (GeneBank accession number: AY358337.1), 2B4 (also known as CD244, accession number: NM_001166664.1), which directly inhibit immune cells. For example, CTLA-4 is a cell-surface protein expressed on certain CD4 and CD8 T cells; when engaged by its ligands (B7-1 and B7-2) on antigen presenting cells, T-cell activation and effector function are inhibited. Thus the present invention relates to a method of engineering T-cells, especially for immunotherapy, comprising genetically modifying T-cells by inactivating at least one protein involved in the immune check-point, in particular PD1 and/or CTLA-4.

In a particular embodiment, said method to engineer cells comprises at least one of the following steps:
(a) providing a T-cell, preferably from a cell culture or from a blood sample;
(b) introducing into said T-cell a rare-cutting endonuclease able to selectively inactivate by DNA cleavage, preferably by double-strand break one gene encoding a immune checkpoint protein,
(c) expanding said cells.

In a more preferred embodiment, said method comprises:
(a) providing a T-cell, preferably from a cell culture or from a blood sample;

(b) transforming said T cell with nucleic acid encoding a rare-cutting endonuclease able to selectively inactivate by DNA cleavage, preferably by double-strand break a gene encoding a immune checkpoint protein;
(c) expressing said rare-cutting endonucleases into said T-cells;
(d) expanding said cells.

In particular embodiment, said rare-cutting endonuclease specifically targets one gene selected from the group consisting of: PD1, CTLA-4, LAG3, Tim3, BTLA, BY55, TIGIT, B7H5, LAIR1, SIGLEC10, 2B4, TCR alpha and TCR beta. In another embodiment, said rare-cutting endonuclease can be a meganuclease, a Zinc finger nuclease, a TALE-nuclease or CAS9/CRISPR endonuclease complex. In a preferred embodiment, said rare-cutting endonuclease is a TALE-nuclease. By TALE-nuclease is intended a fusion protein consisting of a DNA-binding domain derived from a Transcription Activator Like Effector (TALE) and one nuclease catalytic domain to cleave a nucleic acid target sequence. (Boch, Scholze et al. 2009; Moscou and Bogdanove 2009; Christian, Cermak et al. 2010; Cermak, Doyle et al. 2011; Geissler, Scholze et al. 2011; Huang, Xiao et al. 2011; Li, Huang et al. 2011; Mahfouz, Li et al. 2011; Miller, Tan et al. 2011; Morbitzer, Romer et al. 2011; Mussolino, Morbitzer et al. 2011; Sander, Cade et al. 2011; Tesson, Usal et al. 2011; Weber, Gruetzner et al. 2011; Zhang, Cong et al. 2011; Deng, Yan et al. 2012; Li, Piatek et al. 2012; Mahfouz, Li et al. 2012; Mak, Bradley et al. 2012).

Non alloreactive T cells:

In another embodiment, the present invention can be particularly suitable for allogeneic immunotherapy. In this case, one of the steps of genetically modifying cells can be a method comprising:
(a) modifying T-cells by inactivating at least one gene encoding a component of the T-cell receptor (TCR)
(b) Expanding said cells.

In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. In a particular embodiment, said method to engineer cells comprises at least one of the following steps:
(a) Providing a T-cell, preferably from a cell culture or from a blood sample;
Introducing into said T-cell a rare-cutting endonuclease able to selectively inactivate by DNA cleavage, preferably by double-strand break at least one gene encoding a component of the T-cell receptor (TCR).
(b) Expanding said cells.

In a more preferred embodiment, said method comprises:
(a) Providing a T-cell, preferably from a cell culture or from a blood sample;
(b) Transforming said T cell with nucleic acid encoding a rare-cutting endonuclease able to selectively inactivate by DNA cleavage, preferably by double-strand break at least one gene encoding a component of the T-cell receptor (TCR);
(c) Expressing said rare-cutting endonucleases into said T-cells;
(d) Sorting the transformed T-cells, which do not express TCR on their cell surface;
(e) Expanding said cells.

In order to engineer genetically highly active modified immune cells, the invention also provides methods where immune checkpoints are blocked by lack of expression of genes such as PD1 and CTLA-4.

The present application further discloses engineered immune cells in particular T cells to be used as medicament, more particularly, for treating or preventing cancer by administrating such immune cells to a living organism.

The T cells used for adoptive immunotherapy according to the present invention can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Activation and Expansion of T Cells

T-cells can be activated prior to or after genetic modification and expanded in vitro or in vivo generally according to the methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. In general, they are expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell. As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell. In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO2$). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Applications

The engineered isolated immune cell as previously described can be used as a medicament, in particular for the treatment of cancers or infections in a patient in need thereof. The present invention more particularly to methods for treating patients comprising at least one of the following steps:
  (a) providing an immune-cell obtainable by any one of the methods previously described;
  (b) Administrating said transformed immune cells to said patient, Prior to administrating the T cells of the invention, the cells can undergo robust in vivo T cell expansion to obtain persistance for an extended amount of time.

Said treatment can be ameliorating, curative or prophylactic. It may be either part of an autologous immunotherapy or part of an allogenic immunotherapy treatment.

By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of T-cells, typically obtained from donors, into non-alloreactive cells. This may be done under standard protocols and reproduced as many times as needed. The resulted modified T cells may be pooled and administrated to one or several patients, being made available as an "off the shelf" therapeutic product.

Cells that can be used with the disclosed methods are described in the previous section. Said treatment can be used to treat patients diagnosed with cancer, viral infection, autoimmune disorders or Graft versus Host Disease (GvHD). Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the multi-chain CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

The treatment may be administered to patients in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment or chemotherapy since the present invention preferably provides cells or population of cells, which have been made resistant to at least one immunosuppressive and/or chemotherapy agent due to the inactivation of a gene encoding a receptor for such immunosuppressive agent or making it resistant to the chemotherapy treatment. In this aspect, the immunosuppressive or chemotherapy treatment can help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. Said modified cells obtained by any one of the methods described here can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. In the prior art, CAR consisted of single-chain polypeptides comprising an extracellular single chain antibody (scFvFc) fused to the intracellular signaling domain of the T cell antigen receptor complex zeta chain (scFvFc:ζ) and have the ability, when expressed in T cells, to redirect antigen recognition based on the monoclonal antibody's specificity. One example of CAR used in the prior art are CARs directed against CD19 antigen ( ). The CARs according to the present invention are present under single-chain or multi-chain architectures. The extracellular domain(s) thereof consist of single-chain antigen recognition domain comprising a VNAR polypeptide as previously defined. This extracellular domain is anchored to the cell membrane by fusion with a transmembrane domain. The CAR can adopt a single or multi-chain architecture. when the CAR is under a single-chain, said transmembrane domain is fused or includes the signaling domain to form a unique polypeptide. When the CAR is a multi-chain CAR, the signaling domain may be present on another polypeptide that will assemble with the fusion polypeptide comprising the VNAR polypeptide.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, fourty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"similarity" describes the relationship between the amino acid sequences of two or more polypeptides. BLASTP may also be used to identify an amino acid sequence having at least 70%, 75%, 80%, 85%, 87.5%, 90%, 92.5%, 95%, 97.5%, 98%, 99% sequence similarity to a reference amino acid sequence using a similarity matrix such as BLOSUM45, BLOSUM62 or BLOSUM80. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other.

Amino acid sequences having these degrees of identity or similarity or any intermediate degree of identity of similarity to the amino acid sequences disclosed herein are contemplated and encompassed by this disclosure.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1 CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

"bispecific antibody" refers to an antibody that has binding sites for two different antigens within a single antibody molecule. It will be appreciated by those skilled in the art that other molecules in addition to the canonical antibody structure may be constructed with two binding specificities. It will further be appreciated that antigen binding by bispecific antibodies may be simultaneous or sequential. Bispecific antibodies can be produced by chemical techniques (see e.g., Kranz et al. (1981) Proc. Natl. Acad. Sci. USA 78, 5807), by "polydoma" techniques (See U.S. Pat. No. 4,474,893) or by recombinant DNA techniques, which all are known per se. As a non-limiting example, each binding domain comprises at least one variable region from an antibody heavy chain ("VH or H region"), wherein the VH region of the first binding domain specifically binds to the lymphocyte marker such as CD3, and the VH region of the second binding domain specifically binds to tumor antigen.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

Where a numerical limit or range is stated herein, the endpoints are included. Also, all values and subranges within a numerical limit or range are specifically included as if explicitly written out.

The following examples are provided herein for purposes of illustration only, and are not intended to limit the scope of the invention.

EXAMPLES

Electroporation of T Cells with mRNA Encoding Respectively for an Anti-CD19 Single-Chain and Multi-Chain Chimeric Antigen Receptor (CAR):

The same protocol was followed with the following transcripts respectively illustrated in FIGS. 6 and 7:

Monocistronic transcript of SEQ ID NO.110 encoding a VNAR-CAR single chain polypeptide directed against CD19 antigen. This transcripts encodes a single chain polypeptide comprising a VNAR polypeptide anti-CD19 derived from the scaffold SEQ ID NO.1 fused to a transmembrane domain from CD8 alpha, itself fused to the co-stimulatory domain 4-1 BB and the signaling domain CD3zeta comprising an ITAM.

Polycistronic transcript of SEQ ID NO.105 encoding a multi subunit CAR directed against CD19 antigen.T2A and F2A sequences are introduced to split the translated sequences into the different chains. The first chain encode the external VNAR polypeptide anti-CD19 (the same as for the single chain CAR) linked to the transmembrane domain of the FcεRI alpha chain.

In both architectures, the hinge region of CD8 alpha chain was used because it is detectable through PE-conjugated goat antibody staining at the surface of the transformed T-cells.

The transcripts also contained a T cell specific Alpha Signal peptide sequence to enable an efficient addressing to the plasma membrane.

Humanization of the VNAR polypeptide use for targeting CD19 could be done by replacing different structural element of the VNAR primary structure (i.e mostly located outside of CDR3 and CDR1 regions) by amino acid sequence found in structurally similar human antibodies. As an example, such approach has been successfully used to humanize 5A7 VNAR using the human antibody DPK9, a member of variable kappa subgroup 1 (Vk1) as a framework $5 \times 10^6$ T cells preactivated several days (3-5) with anti-CD3/CD28 coated beads and IL2 were resuspended in cytoporation buffer T, and electroporated in 0.4 cm cuvettes without mRNA or with 10 µg of mRNA respectively encoding the single chain VNAR-CAR (SEQ ID NO: 110) and the multi-chain VNAR-CAR (SEQ ID NO.105).

24 hours post electroporation, cells were stained with a fixable viability dye eFluor-780 and a PE-conjugated goat anti-CD8 to assess the cell surface expression of the CAR on the live cells.

24 hours post electroporation, T cells were cocultured with Daudi (CD19+) cells for 6 hours and analyzed by flow cytometry to detect the expression of the degranulation marker CD107a at their surface (Betts, Brenchley et al. 2003).

The results showed that the majority of the cells electroporated, either with the monocistronic mRNA or the polycistronic mRNA as described above degranulated in the presence of target cells expressing CD19. These results clearly demonstrate that the VNAR-CAR expressed at the surface of electroporated T cells were active under both single-chain and multi-chain architectures.

TABLE 2

| Sequences listed in the present specification | |
|---|---|
| Sequence Description | SEQ_ID_NO |
| >gi|491668396|pdb|4HGK|D Chain D, Shark Ignar Variable Domain (E06) | SEQ_ID NO 1 |
| >gi|491668397|pdb|4HGM|A Chain A, Shark Ignar Variable Domain | SEQ_ID NO 2 |
| >gi|59892033|gb|AAX10148.1| immunoglobulin NAR variable region, partial [*Heterodontus francisci*] | SEQ_ID NO 3 |
| >gi|59892031|gb|AAX10147.1| immunoglobulin NAR variable region, partial [*Heterodontus francisci*] | SEQ_ID NO 4 |
| >gi|355525308|gb|AES92986.1| IgNAR immunoglobulin heavy chain secretory form, partial [*Squalus acanthias*] | SEQ_ID NO 5 |
| >gi|355525312|gb|AES92988.1| IgNAR immunoglobulin heavy chain secretory form, partial [*Squalus acanthias*] | SEQ_ID NO 6 |
| >gi|355525306|gb|AES92985.1| IgNAR immunoglobulin heavy chain secretory form, partial [*Squalus acanthias*] | SEQ_ID NO 7 |
| >gi|59892021|gb|AAX10142.1| immunoglobulin NAR variable region, partial [*Heterodontus francisci*] | SEQ_ID NO 8 |
| >gi|59892019|gb|AAX10141.1| immunoglobulin NAR variable region, partial [*Heterodontus francisci*] | SEQ_ID NO 9 |
| >gi|59892017|gb|AAX10140.1| immunoglobulin NAR variable region, partial [*Heterodontus francisci*] | SEQ_ID NO 10 |
| >gi|21539972|gb|AAM52970.1| antigen receptor [*Ginglymostoma cirratum*] | SEQ_ID NO 11 |
| >gi|355525310|gb|AES92987.1| IgNAR immunoglobulin heavy chain secretory form, partial [*Squalus acanthias*] | SEQ_ID NO 12 |
| >gi|25987499|gb|AAN75876.1|AF447120_1 novel antigen receptor [*Ginglymostoma cirratum*] | SEQ_ID NO 13 |
| >gi|21805812|gb|AAM76812.1| antigen receptor [*Ginglymostoma cirratum*] | SEQ_ID NO 14 |
| >gi|25987497|gb|AAN75875.1|AF447119_1 novel antigen receptor [*Ginglymostoma cirratum*] | SEQ_ID NO 15 |
| >gi|307685087|dbj|BAJ20185.1| immunoglobulin NAR [*Triakis scyllium*] | SEQ_ID NO 16 |
| >gi|59892015|gb|AAX10139.1| immunoglobulin NAR variable region, partial [*Heterodontus francisci*] | SEQ_ID NO 17 |
| >gi|3982965|gb|AAC83733.1| antigen receptor [*Ginglymostoma cirratum*] | SEQ_ID NO 18 |
| >gi|21747962|gb|AAM76235.1| antigen receptor [*Ginglymostoma cirratum*] | SEQ_ID NO 19 |
| >gi|21898882|gb|AAM77162.1| antigen receptor [*Ginglymostoma cirratum*] | SEQ_ID NO 20 |
| >gi|21805800|gb|AAM76806.1| antigen receptor [*Ginglymostoma cirratum*] | SEQ_ID NO 21 |
| >gi|59892023|gb|AAX10143.1| immunoglobulin NAR variable region, partial [*Heterodontus francisci*] | SEQ_ID NO 22 |
| >gi|21805822|gb|AAM76817.1| antigen receptor [*Ginglymostoma cirratum*] | SEQ_ID NO 23 |
| >gi|21898926|gb|AAM77183.1| antigen receptor [*Ginglymostoma cirratum*] | SEQ_ID NO 24 |
| >gi|21655108|gb|AAL58520.1| new antigen receptor variable domain [*Orectolobus maculatus*] | SEQ_ID NO 25 |
| >gi|52696108|pdb|1VER|A Chain A, Structure Of New Antigen Receptor Variable Domain From Sharks >gi|32709090|gb|AAP86761.1| new antigen receptor variable domain [*Orectolobus maculatus*] | SEQ_ID NO 26 |
| >gi|3986584|gb|AAC84086.1| antigen receptor [*Ginglymostoma cirratum*] | SEQ_ID NO 27 |
| >gi|3983003|gb|AAC83752.1| antigen receptor [*Ginglymostoma cirratum*] | SEQ_ID NO 28 |
| >gi|15420366|gb|AAK97360.1| new antigen receptor [*Orectolobus maculatus*] | SEQ_ID NO 29 |
| >gi|59892029|gb|AAX10146.1| immunoglobulin NAR variable region [*Heterodontus francisci*] | SEQ_ID NO 30 |
| >gi|59892025|gb|AAX10144.1| immunoglobulin NAR variable region, partial [*Heterodontus francisci*] | SEQ_ID NO 31 |
| >gi|25987461|gb|AAN75857.1|AF447101_1 novel antigen receptor [*Ginglymostoma cirratum*] | SEQ_ID NO 32 |
| >gi|21898887|gb|AAM77164.1| antigen receptor [*Ginglymostoma cirratum*] | SEQ_ID NO 33 |
| >gi|21898924|gb|AAM77182.1| antigen receptor [*Ginglymostoma cirratum*] | SEQ_ID NO 34 |
| >gi|3983053|gb|AAC83777.1| antigen receptor [*Ginglymostoma cirratum*] | SEQ_ID NO 35 |
| >gi|21539902|gb|AAM52938.1| antigen receptor [*Ginglymostoma cirratum*] | SEQ_ID NO 36 |
| >gi|307685089|dbj|BAJ20186.1| immunoglobulin NAR [*Triakis scyllium*] | SEQ_ID NO 37 |
| >gi|3986580|gb|AAC84084.1| antigen receptor [*Ginglymostoma cirratum*] | SEQ_ID NO 38 |
| >gi|126009471|gb|ABN64030.1| antigen receptor variable domain [*Orectolobus maculatus*] | SEQ_ID NO 39 |
| >gi|25987459|gb|AAN75856.1|AF447100_1 novel antigen receptor [*Ginglymostoma cirratum*] | SEQ_ID NO 40 |
| >gi|307685093|dbj|BAJ20188.1| immunoglobulin NAR [*Triakis scyllium*] | SEQ_ID NO 41 |
| >gi|21748031|gb|AAM76269.1| antigen receptor [*Ginglymostoma cirratum*] | SEQ_ID NO 42 |
| >gi|3986664|gb|AAC84126.1| antigen receptor [*Ginglymostoma cirratum*] | SEQ_ID NO 43 |
| >gi|3982949|gb|AAC83725.1| antigen receptor [*Ginglymostoma cirratum*] | SEQ_ID NO 44 |
| >gi|21885446|gb|AAM76964.1| antigen receptor [*Ginglymostoma cirratum*] | SEQ_ID NO 45 |
| >gi|21069163|gb|AAM33846.1|AF466396_1 new antigen receptor variable domain [*Orectolobus maculatus*] | SEQ_ID NO 46 |
| >gi|21898928|gb|AAM77184.1| antigen receptor [*Ginglymostoma cirratum*] | SEQ_ID NO 47 |
| >gi|21885420|gb|AAM76954.1| antigen receptor [*Ginglymostoma cirratum*] | SEQ_ID NO 48 |
| >gi|21748025|gb|AAM76266.1| antigen receptor [*Ginglymostoma cirratum*] | SEQ_ID NO 49 |
| >gi|21748015|gb|AAM76261.1| antigen receptor [*Ginglymostoma cirratum*] | SEQ_ID NO 50 |
| >gi|21539976|gb|AAM52972.1| antigen receptor [*Ginglymostoma cirratum*] | SEQ_ID NO 51 |
| >gi|21747995|gb|AAM76251.1| antigen receptor [*Ginglymostoma cirratum*] | SEQ_ID NO 52 |
| >gi|21805816|gb|AAM76814.1| antigen receptor [*Ginglymostoma cirratum*] | SEQ_ID NO 53 |
| >gi|21747977|gb|AAM76242.1| antigen receptor [*Ginglymostoma cirratum*] | SEQ_ID NO 54 |

TABLE 2-continued

Sequences listed in the present specification

| Sequence Description | SEQ_ID_NO |
|---|---|
| >gi\|21539983\|gb\|AAM52975.1\| antigen receptor [*Ginglymostoma cirratum*] | SEQ_ID NO 55 |
| >gi\|21885436\|gb\|AAM76960.1\| antigen receptor [*Ginglymostoma cirratum*] | SEQ_ID NO 56 |
| >gi\|25987495\|gb\|AAN75874.1\|AF447118_1 novel antigen receptor [*Ginglymostoma cirratum*] | SEQ_ID NO 57 |
| >gi\|21885442\|gb\|AAM76962.1\| antigen receptor [*Ginglymostoma cirratum*] | SEQ_ID NO 58 |
| >gi\|21885444\|gb\|AAM76963.1\| antigen receptor [*Ginglymostoma cirratum*] | SEQ_ID NO 59 |
| >gi\|21748009\|gb\|AAM76258.1\| antigen receptor [*Ginglymostoma cirratum*] | SEQ_ID NO 60 |
| >gi\|21539988\|gb\|AAM52977.1\| antigen receptor [*Ginglymostoma cirratum*] | SEQ_ID NO 61 |
| >gi\|21748029\|gb\|AAM76268.1\| antigen receptor [*Ginglymostoma cirratum*] | SEQ_ID NO 62 |
| >gi\|3986602\|gb\|AAC84095.1\| antigen receptor [*Ginglymostoma cirratum*] | SEQ_ID NO 63 |
| >gi\|699465\|gb\|AAB48206.1\| novel antigen receptor, partial [*Ginglymostoma cirratum*] | SEQ_ID NO 64 |
| >gi\|21539974\|gb\|AAM52971.1\| antigen receptor [*Ginglymostoma cirratum*] | SEQ_ID NO 65 |
| >gi\|161172318\|pdb\|2Z8W\|C Chain C, Structure Of An Ignar-Ama1 Complex | SEQ_ID NO 66 |
| >gi\|161172319\|pdb\|2Z8W\|D Chain D, Structure Of An Ignar-Ama1 Complex | |
| >gi\|21747979\|gb\|AAM76243.1\| antigen receptor [*Ginglymostoma cirratum*] | SEQ_ID NO 67 |
| >gi\|21747983\|gb\|AAM76245.1\| antigen receptor [*Ginglymostoma cirratum*] | SEQ_ID NO 68 |
| >gi\|21898862\|gb\|AAM77152.1\| antigen receptor [*Ginglymostoma cirratum*] | SEQ_ID NO 69 |
| >gi\|25987501\|gb\|AAN75877.1\|AF447121_1 novel antigen receptor [*Ginglymostoma cirratum*] | SEQ_ID NO 70 |
| >gi\|52696109\|pdb\|1VES\|A Chain A, Structure Of New Antigen Receptor Variable Domain From Sharks | SEQ_ID NO 71 |
| >gi\|21898858\|gb\|AAM77150.1\| antigen receptor [*Ginglymostoma cirratum*] | SEQ_ID NO 72 |
| >gi\|3986668\|gb\|AAC84128.1\| antigen receptor [*Ginglymostoma cirratum*] | SEQ_ID NO 73 |
| >gi\|21747989\|gb\|AAM76248.1\| antigen receptor [*Ginglymostoma cirratum*] | SEQ_ID NO 74 |
| >gi\|21747970\|gb\|AAM76239.1\| antigen receptor [*Ginglymostoma cirratum*] | SEQ_ID NO 75 |
| >gi\|3982935\|gb\|AAC83718.1\| antigen receptor [*Ginglymostoma cirratum*] | SEQ_ID NO 76 |
| >gi\|134104489\|pdb\|2I26\|N Chain N, Crystal Structure Analysis Of The Nurse Shark New Antigen Receptor Ancestral Variable Domain In Complex With Lysozyme | SEQ_ID NO 77 |
| >gi\|3982937\|gb\|AAC83719.1\| antigen receptor [*Ginglymostoma cirratum*] | SEQ_ID NO 78 |
| >gi\|3982933\|gb\|AAC83717.1\| antigen receptor [*Ginglymostoma cirratum*] | SEQ_ID NO 79 |
| >gi\|3982955\|gb\|AAC83728.1\| antigen receptor [*Ginglymostoma cirratum*] | SEQ_ID NO 80 |
| >gi\|307685091\|dbj\|BAJ20187.1\| immunoglobulin NAR [*Triakis scyllium*] | SEQ_ID NO 81 |
| >gi\|3982959\|gb\|AAC83730.1\| antigen receptor [*Ginglymostoma cirratum*] | SEQ_ID NO 82 |
| >gi\|3986596\|gb\|AAC84092.1\| antigen receptor [*Ginglymostoma cirratum*] | SEQ_ID NO 83 |
| >gi\|25987449\|gb\|AAN75851.1\|AF447095_1 novel antigen receptor [*Ginglymostoma cirratum*] | SEQ_ID NO 84 |
| >gi\|21748017\|gb\|AAM76262.1\| antigen receptor [*Ginglymostoma cirratum*] | SEQ_ID NO 85 |
| >gi\|21885448\|gb\|AAM76965.1\| antigen receptor [*Ginglymostoma cirratum*] | SEQ_ID NO 86 |
| >gi\|25987493\|gb\|AAN75873.1\|AF447117_1 novel antigen receptor [*Ginglymostoma cirratum*] | SEQ_ID NO 87 |
| >gi\|21885434\|gb\|AAM76959.1\| antigen receptor [*Ginglymostoma cirratum*] | SEQ_ID NO 88 |
| >gi\|21885454\|gb\|AAM76968.1\| antigen receptor [*Ginglymostoma cirratum*] | |
| >gi\|21885378\|gb\|AAM76934.1\| antigen receptor [*Ginglymostoma cirratum*] | SEQ_ID NO 89 |
| >gi\|3983005\|gb\|AAC83753.1\| antigen receptor [*Ginglymostoma cirratum*] | SEQ_ID NO 90 |
| >gi\|3982975\|gb\|AAC83738.1\| antigen receptor [*Ginglymostoma cirratum*] | SEQ_ID NO 91 |
| >gi\|21885440\|gb\|AAM76961.1\| antigen receptor [*Ginglymostoma cirratum*] | SEQ_ID NO 92 |
| >gi\|3986588\|gb\|AAC84088.1\| antigen receptor [*Ginglymostoma cirratum*] | SEQ_ID NO 93 |
| >gi\|21885395\|gb\|AAM76942.1\| antigen receptor [*Ginglymostoma cirratum*] | SEQ_ID NO 94 |
| >gi\|21539954\|gb\|AAM52962.1\| antigen receptor [*Ginglymostoma cirratum*] | SEQ_ID NO 95 |
| >gi\|21805808\|gb\|AAM76810.1\| antigen receptor [*Ginglymostoma cirratum*] | SEQ_ID NO 96 |
| >gi\|699417\|gb\|AAB48359.1\| novel antigen receptor, partial [*Ginglymostoma cirratum*] | SEQ_ID NO 97 |
| >gi\|21898842\|gb\|AAM77142.1\| antigen receptor [*Ginglymostoma cirratum*] | SEQ_ID NO 98 |
| >gi\|21805883\|gb\|AAM76843.1\| antigen receptor [*Ginglymostoma cirratum*] | SEQ_ID NO 99 |
| >gi\|21539947\|gb\|AAM52959.1\| antigen receptor [*Ginglymostoma cirratum*] | SEQ_ID NO 100 |
| >1SQ2:N\|PDBID\|CHAIN\|SEQUENCE (5A7) | SEQ_ID NO 101 |
| New antigen receptor (*Orectolobus*) Q90XW8_9CHON amino acid sequence (*Orectolobus maculatus* clone 7E-80 new antigen receptor) | SEQ_ID NO 102 |
| Alpha-Signal-peptide(from pCLS22370) amino acid sequence | SEQ_ID NO 103 |
| Signal-peptide(from Q90XW8_9CHON) amino acid sequence | SEQ_ID NO 104 |
| Chimeric VNAR-CAR2(multi-chain + endogeneous hinge domain) | SEQ_ID NO 105 |
| Chimeric VNAR-CAR3 (multi-chain + IgG1 hinge domain) | SEQ_ID NO 106 |
| Chimeric VNAR-CAR4 (multi-chain + CD8 hinge domain) | SEQ_ID NO 107 |
| Chimeric VNAR-CAR5 (single chain + endogenous hinge domain) | SEQ_ID NO 108 |
| Chimeric VNAR-CAR6 (single chain + IgG1 hinge domain) | SEQ_ID NO 109 |
| Chimeric VNAR-CAR7 (single chain + CD8 hinge domain) | SEQ_ID NO 110 |
| IgG1 hinge CH2 CH3 | SEQ_ID NO 111 |
| CD8 alpha hinge | SEQ_ID NO 112 |
| >sp\|P02786\|89-760 TFR1_HUMAN amino acid sequence of the extracellular region | SEQ_ID NO 113 |
| >sp\|Q9UP52\|105-801 TFR2_HUMAN amino acid sequence of the extracellular region | SEQ_ID NO 114 |
| 12A9 | SEQ_ID NO 115 |

LIST OF REFERENCES

Ashwell, J. D. and R. D. Klusner (1990). "Genetic and mutational analysis of the T-cell antigen receptor." *Annu Rev Immunol* 8: 139-67.

Betts, M. R., J. M. Brenchley, et al. (2003). "Sensitive and viable identification of antigen-specific CD8+ T cells by a flow cytometric assay for degranulation." *J Immunol Methods* 281(1-2): 65-78.

Boch, J., H. Scholze, et al. (2009). "Breaking the code of DNA binding specificity of TAL-type III effectors." *Science* 326(5959): 1509-12.

Cambier, J. C. (1995). "Antigen and Fc receptor signaling. The awesome power of the immunoreceptor tyrosine-based activation motif (ITAM)." *J Immunol* 155(7): 3281-5.

Cermak, T., E. L. Doyle, et al. (2011). "Efficient design and assembly of custom TALEN and other TAL effector-based constructs for DNA targeting." *Nucleic Acids Res* 39(12): e82.

Christian, M., T. Cermak, et al. (2010). "Targeting DNA double-strand breaks with TAL effector nucleases." *Genetics* 186(2): 757-61.

Deng, D., C. Yan, et al. (2012). "Structural basis for sequence-specific recognition of DNA by TAL effectors." *Science* 335(6069): 720-3.

Geissler, R., H. Scholze, et al. (2011). "Transcriptional activators of human genes with programmable DNA-specificity." *PLoS One* 6(5): e19509.

Huang, P., A. Xiao, et al. (2011). "Heritable gene targeting in zebrafish using customized TALENs." *Nat Biotechnol* 29(8): 699-700.

Jena, B., G. Dotti, et al. (2010). "Redirecting T-cell specificity by introducing a tumor-specific chimeric antigen receptor." *Blood* 116(7): 1035-44.

Kovalenko, O. V., et al. (2013). "Atypical antigen recognition mode of a shark IgNAR variable domain characterized by humanization and structural analysis". *J. Biol. Chem.* 288: 17408-17419.

Li, L., M. J. Piatek, et al. (2012). "Rapid and highly efficient construction of TALE-based transcriptional regulators and nucleases for genome modification." *Plant Mol Biol* 78(4-5): 407-16.

Li, T., S. Huang, et al. (2011). "TAL nucleases (TALNs): hybrid proteins composed of TAL effectors and FokI DNA-cleavage domain." *Nucleic Acids Res* 39(1): 359-72.

Li, T., S. Huang, et al. (2011). "Modularly assembled designer TAL effector nucleases for targeted gene knockout and gene replacement in eukaryotes." *Nucleic Acids Res* 39(14): 6315-25.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mahfouz, M. M., L. Li, et al. (2011). "De novo-engineered transcription activator-like effector (TALE) hybrid nuclease with novel DNA binding specificity creates double-strand breaks." *Proc Natl Acad Sci USA* 108(6): 2623-8.

Mak, A. N., P. Bradley, et al. (2012). "The crystal structure of TAL effector PthXo1 bound to its DNA target." *Science* 335(6069): 716-9.

Metzger, H., G. Alcaraz, et al. (1986). "The receptor with high affinity for immunoglobulin E." *Annu Rev Immunol* 4: 419-70.

Miller, J. C., S. Tan, et al. (2011). "A TALE nuclease architecture for efficient genome editing." *Nat Biotechnol* 29(2): 143-8.

Morbitzer, R., P. Romer, et al. (2011). "Regulation of selected genome loci using de novo-engineered transcription activator-like effector (TALE)-type transcription factors." *Proc Natl Acad Sci USA* 107(50): 21617-22.

Moscou, M. J. and A. J. Bogdanove (2009). "A simple cipher governs DNA recognition by TAL effectors." *Science* 326(5959): 1501.

Mussolino, C., R. Morbitzer, et al. (2011). "A novel TALE nuclease scaffold enables high genome editing activity in combination with low toxicity." *Nucleic Acids Res* 39(21): 9283-93.

Park, T. S., S. A. Rosenberg, et al. (2011). "Treating cancer with genetically engineered T cells." *Trends Biotechnol* 29(11): 550-7.

Sander, J. D., L. Cade, et al. (2011). "Targeted gene disruption in somatic zebrafish cells using engineered TALENs." *Nat Biotechnol* 29(8): 697-8.

Tesson, L., C. Usal, et al. (2011). "Knockout rats generated by embryo microinjection of TALENs." *Nat Biotechnol* 29(8): 695-6.

Weber, E., R. Gruetzner, et al. (2011). "Assembly of designer TAL effectors by Golden Gate cloning." *PLoS One* 6(5): e19722.

Zhang, F., L. Cong, et al. (2011). "Efficient construction of sequence-specific TAL effectors for modulating mammalian transcription." *Nat Biotechnol* 29(2): 149-53.

---

The invention claimed is:

1. A chimeric antigen receptor (CAR) comprising:
   one extracellular antigen recognition domain comprising at least one Complementary Determining Region (CDR) of a variable new antigen receptor (VNAR) polypeptide,
   wherein the CAR is a multi-chain CAR, comprising a first transmembrane polypeptide and a second transmembrane polypeptide that are separate and different transmembrane polypeptides expressed on an immune cell,
   wherein the first transmembrane polypeptide is fused with the extracellular antigen recognition domain comprising at least one CDR that recognizes an antigen on a target cell and wherein the first transmembrane polypeptide does not contain a signal transducing domain,
   and wherein the first transmembrane polypeptide does not contain a signal transducing domain, and wherein the first transmembrane polypeptide does not contain a co-stimulatory domain, and
   wherein the first and the second transmembrane polypeptides multimerize to form a multi-chain CAR.

2. The CAR according to claim 1, wherein said first and second transmembrane polypeptides comprise a portion of a FcεRI alpha chain, FcεRI beta chain and/or FcεRI gamma chain or a variant thereof, such that said FcεRI chains dimerize, trimerize or tetramerize together to form a muitimeric CAR.

3. A method of treating cancer or an autoimmune disease comprising administering to a subject in need thereof an engineered immune cell comprising at least one CAR according to claim 1.

4. A method of treating cancer or an autoimmune disease comprising administering to a subject in need thereof an engineered immune cell comprising at least one CAR according to claim 2.

5. The CAR according to claim 1, wherein said VNAR polypeptide comprises an amino acid sequence identity of at least 50% to any of SEQ ID NO. 1 to 100.

6. The CAR according to claim 2, wherein said VNAR polypeptide comprises an amino acid sequence identity of at least 50% to any of SEQ ID NO. 1 to 100.

* * * * *

UNITED STATES PATENT AND TRADEMARK OFFICE
CERTIFICATE OF CORRECTION

PATENT NO. : 10,526,406 B2
APPLICATION NO. : 15/111441
DATED : January 7, 2020
INVENTOR(S) : Duchateau et al.

Page 1 of 1

It is certified that error appears in the above-identified patent and that said Letters Patent is hereby corrected as shown below:

In the Claims

Column 173
Lines 28-29, Claim 1, delete "and wherein the first transmembrane polypeptide does not contain a signal transducing domain,"

Signed and Sealed this
Seventh Day of April, 2020

Andrei Iancu
*Director of the United States Patent and Trademark Office*